US007605158B2

(12) United States Patent
Kawaguchi et al.

(10) Patent No.: US 7,605,158 B2
(45) Date of Patent: Oct. 20, 2009

(54) CARBAMOYL-TYPE BENZOFURAN DERIVATIVES

(75) Inventors: Takayuki Kawaguchi, Osaka (JP); Hidenori Akatsuka, Osaka (JP); Masamichi Morimoto, Osaka (JP); Tatsuya Watanabe, Osaka (JP); Toru Iijima, Osaka (JP); Jun Murakami, Osaka (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 658 days.

(21) Appl. No.: 10/571,904

(22) PCT Filed: Sep. 24, 2004

(86) PCT No.: PCT/JP2004/013891

§ 371 (c)(1), (2), (4) Date: Mar. 14, 2006

(87) PCT Pub. No.: WO2005/030759

PCT Pub. Date: Apr. 7, 2005

(65) Prior Publication Data

US 2006/0247273 A1 Nov. 2, 2006

(30) Foreign Application Priority Data

Sep. 26, 2003 (JP) ............................ 2003-334597

(51) Int. Cl.
*A61K 31/5355* (2006.01)
*A61K 31/443* (2006.01)
*C07D 413/04* (2006.01)
*C07D 401/12* (2006.01)
*C07D 307/85* (2006.01)

(52) U.S. Cl. .................... 514/233.5; 514/337; 514/470; 544/124; 546/193; 546/279.1; 546/284.1; 549/467

(58) Field of Classification Search ................. 544/124; 546/193, 279.1, 284.1; 549/467; 514/233.5, 514/337, 470
See application file for complete search history.

(56) References Cited

U.S. PATENT DOCUMENTS

| | | | |
|---|---|---|---|
| 5,635,527 | A | 6/1997 | Ono et al. |
| 5,753,670 | A | 5/1998 | Ono et al. |
| 6,140,351 | A | 10/2000 | Amaiz et al. |
| 6,380,221 | B1 | 4/2002 | Amaiz et al. |
| 6,498,185 | B1 | 12/2002 | Amaiz et al. |
| 6,635,657 | B1 | 10/2003 | Beight et al. |
| 6,686,368 | B1 | 2/2004 | Zhu et al. |
| 6,759,414 | B2 | 7/2004 | Beight et al. |
| 2004/0029874 | A1 | 2/2004 | Beight et al. |

FOREIGN PATENT DOCUMENTS

| | | | |
|---|---|---|---|
| WO | WO-95/33720 | A1 | 12/1995 |
| WO | WO-99/32477 | | 7/1999 |
| WO | WO-99/32477 | A1 | 7/1999 |
| WO | WO-99/42439 | | 8/1999 |
| WO | WO-00/39118 | | 7/2000 |
| WO | WO-00/39118 | A | 7/2000 |
| WO | WO-01/19788 | A2 | 3/2001 |
| WO | WO-02/12189 | A1 | 2/2002 |
| WO | WO-02/079145 | A1 | 10/2002 |
| WO | WO-03/082847 | A1 | 10/2003 |
| WO | WO-2004/063202 | A1 | 7/2004 |

OTHER PUBLICATIONS

Roy, K et al., Drug Design and Discovery, 2002, 18, pp. 23 to 31.
Roy, K. et al., Drug and Design and Discovery, 2002, 18, pp. 33 to 43.

(Continued)

*Primary Examiner*—Bernard Dentz
(74) *Attorney, Agent, or Firm*—Birch, Stewart, Kolasch & Birch, LLP

(57) ABSTRACT

The present invention provides a carbamoyl-type benzofuran derivative of the formula [1]:

[1]

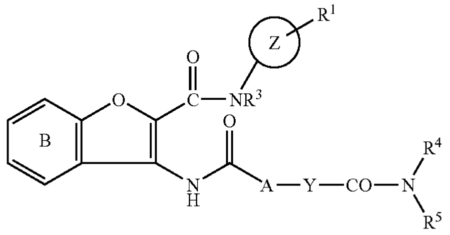

wherein Ring Z is a group of the formula:

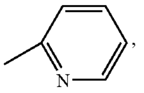

etc.; A is a single bond, and the like; Y is a cycloalkanediyl group, etc.; $R^4$ and $R^5$ are the same or different and each is an optionally substituted lower alkyl group, etc.; $R^1$ is a halogen atom, etc.; Ring B of the formula:

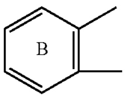

is an optionally substituted benzene ring; and $R^3$ is a hydrogen atom. etc., or a pharmaceutically acceptable salt thereof, which is useful as an FXa inhibitor.

19 Claims, No Drawings

OTHER PUBLICATIONS

Roy, K. et al., Drug Design and Discovery, 2002, 18, pp. 23 to 31.

Freedman, "Oral Anticoagulants: Pharmacodynamics, Clinical Indications and Adverse Effects", Journal of Clinical Pharmacology, vol. 32, pp. 196-209, 1992.

Hirsh, "Oral Antiocoagulant Drugs", The New England Journal of Medicine, vol. 324, No. 26, pp. 1865-1875, 1991.

Sixma, et al., "The Ideal Anti-Thrombotic Drug", Thrombosis Research, Erratum, vol. 68, No. 6, pp. 507-512, 1992.

Matsuo, "t-PA and Pro-UK", Gakusaikikaku, pp. 5-40, 1986.

Kaiser, et al., "Pharmacological Characterization of a New Highly Effective Synthetic Thrombin Inhibitor", Biomed Biochim Acta, vol. 44, 7/8, pp. 1201-1210, 1985.

Tidwell, et al., "Strategies for Anticoagulation with Synthetic Protease Inhibitors, Xa Inhibitors Versus Thrombin Inhibitors", Thrombosis Research, vol. 19, pp. 339-349, 1980.

Harwalkar, et al., "Synthesis and Reactions of 2-Substituted-4*H*-Benzofuro[3,2-d]-m-Oxazin-4-Ones", Indian Journal of Heterocyclic Chemistry, vol. 3, pp. 247-252, 1994.

Viti, et al., "Synthesis of New Arylbenzofurodiazepin-6-Ones", Journal of Heterocyclic Chemistry, 27(5), pp. 1369-1375, 1990.

CARBAMOYL-TYPE BENZOFURAN DERIVATIVES

TECHNICAL FIELD

The present invention relates to carbamoyl-type benzofuran derivatives useful as a medicament, particularly as an inhibitor of activated blood coagulation factor X (hereinafter, referred to as "FXa"), or pharmaceutically acceptable salt thereof.

BACKGROUND ART

In late years, as the westernization of living habit and the aging of populations, thromboembolic diseases such as myocardial infarction, cerebral infarction and peripheral arterial thrombosis increase year by year, and social importance of treatment thereof has risen more and more.

Among therapies of thromboembolic diseases, anticoagulant therapy, as well as fibrinolytic therapy and antiplatelet therapy, takes part in medical therapy for treatment and prevention of thrombosis (Sogorinsho 41: 2141-2145, 1989). In particular, the safety sustainable to chronic administration and the reliable and appropriate expression of anticoagulant activity are essential in the prevention of thrombosis. A coumarin derivative, especially warfarin potassium, has often been used all over the world as an anticoagulant available orally. However, owing to the characteristics arisen from the mechanism of action, it requires long time until the drug efficacy manifests and has very long half-life in blood, although the concentration range for expression of drug efficacy is relatively narrow, and also shows significant differences in the effective dose among individuals. For these reasons, the anticoagulant ability can hardly be controlled (Journal of Clinical Pharmacology, 1992, vol. 32, pp. 196-209; NEW ENGLAND JOURNAL OF MEDICINE, 1991, vol. 324, no. 26, pp. 1865-1875). In addition, there may be adverse drug reactions such as risk of bleeding, nausea, vomiting, diarrhea, depilation, and the like, and therefore the clinical application thereof is very difficult and the development of anticoagulants that are useful and easy to handle has been demanded.

Furthermore, enhancement of blood clotting ability is one of significant causative factors of unstable angina, cerebral infarction, cerebral embolism, myocardial infarction, pulmonary infarction, pulmonary embolism, Buerger's disease, deep vein thrombosis, disseminated intravascular coagulation, thrombogenesis after artificial heart valve displacement, reocclusion after blood circulation reconstruction and thrombogenesis during extracorporeal circulation, and the like Therefore, a distinguished anticoagulant that shows good dose response and lower risk of hemorrhage with few side-effects, and can exert sufficient effects by oral administration has been desired (Thrombosis Research, 1992, vol. 68, pp. 507-512).

Thrombin participates not only in the conversion of fibrinogen to fibrin, which is the final stage of the coagulation cascade, but also deeply in the activation and aggregation of blood platelets (Matsuo, O., "t-PA and Pro-UK", Gakusaikikaku, 1986, pp. 5-40), and an inhibitor thereof has long been the center of the research in anticoagulants as a target of development of new drugs. However, a thrombin inhibitor shows low bioavailability upon oral administration and also has drawbacks in regard to safety such as bleeding tendency as one of side effects (Biomedica Biochimica Acta, 1985, Vol. 44, p. 1201-1210).

FXa is a key enzyme located in the position of the common pathway of both extrinsic and intrinsic coagulation cascade reactions. FXa is located upstream from thrombin in the coagulation cascade. Therefore, the inhibition of FXa is possibly more effective and specific in the inhibition of coagulation system compared to the inhibition of thrombin (Thrombosis Research, 1980, Vol. 19, pp. 339-349).

Thus, a substance which inhibits FXa and shows distinguished enzyme selectivity and high bioavailability is expected to undergo control of its anticoagulant activity for a long period of time and can express superior therapeutic effect upon oral administration compared to the existing anticoagulants. Accordingly, the development of a novel FXa inhibitor adapted to oral administration has been earnestly demanded.

Examples of known compounds having inhibitory effect on FXa include thiobenzamide compounds that are useful in prevention or treatment of thrombosis (WO99/42439).

The following benzofuran compounds have also been known (Indian Journal of Hetero Cyclic Chemistry, 1994, Vol. 3, pp. 3247-3252), but said literature does not mention about the inhibitory effect of the compounds on FXa.

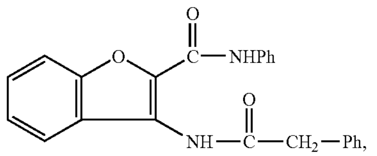

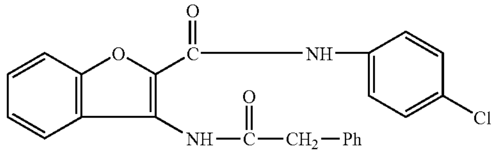

Condensed bicyclic amide compounds of the formula:

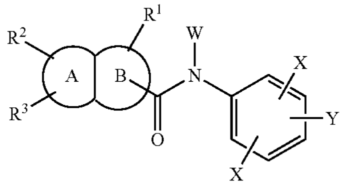

which has an activity of suppressing the growth of activated lymphocytes and are useful as a drug for preventing or treating autoimmune diseases are also known (WO02/12189). The WO02/12189 does not mention about the inhibitory effect on FXa either. In the pamphlet, compounds having a condensed ring of pyridine and furan to which ring an amide and a carbamoyl groups are di-substituted are disclosed; however, said compounds all have a benzene ring on the nitrogen atom of the carbamoyl group, said benzene ring being substituted by X and Y simultaneously.

DISCLOSURE OF INVENTION

The present invention provides a novel carbamoyl-type benzofuran derivative having excellent inhibitory effect on FXa, or pharmaceutically acceptable salts thereof.

The present inventors have intensively studied and have found that a carbamoyl-type benzofuran derivative of the formula below has an excellent FXa-inhibiting activity and advantageous features that enable controlling anticoagulant activity for a long period of time upon oral administration, and established the present invention.

That is, the present invention is as follows:

1. A carbamoyl-type benzofuran derivative of the formula [1]:

[1]

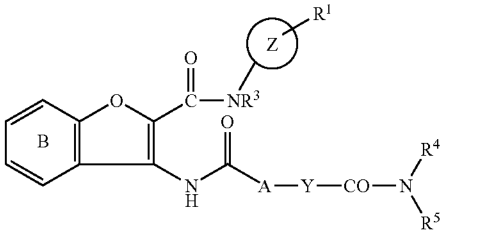

wherein Ring Z is a group of the formula:

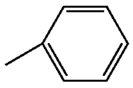 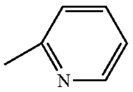 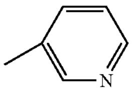 or 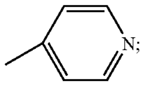

A is a single bond or a group of the formula: —NH—;

Y is a lower alkylene group, a cycloalkanediyl group, a phenyl group or a saturated heterocyclic group;

$R^4$ and $R^5$ are the same or different and each is a hydrogen atom, an optionally substituted lower alkyl group or an optionally substituted saturated heterocyclic group, or $R^4$ and $R^5$ combine together at the ends to form an optionally substituted nitrogen-containing saturated heterocyclic group along with the adjacent nitrogen atom;

$R^1$ is a hydrogen atom, a halogen atom, a lower alkyl group, a lower alkoxy group, a cyano group, or an amino group optionally substituted by 1 to 2 lower alkyl groups;

Ring B of the formula:

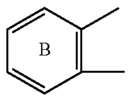

is an optionally substituted benzene ring; and $R^3$ is a hydrogen atom or a lower alkyl group, or a pharmaceutically acceptable salt thereof.

2. The compound according to 1 above, wherein Ring Z is a group of the formula:

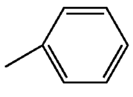 or 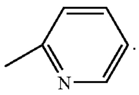.

3. The compound according to 2 above, wherein the "optionally substituted lower alkyl group" for $R^4$ or $R^5$ is an unsubstituted lower alkyl group, a lower alkyl group substituted by an amino group optionally substituted by 1 to 2 lower alkyl groups, a lower alkyl group substituted by a hydroxyl group, a lower alkyl group substituted by a lower alkoxy group or a lower alkyl group substituted by a pyridyl group;

the "optionally substituted saturated heterocyclic group" for $R^4$ or $R^5$ is tetrahydropyranyl;

the "optionally substituted nitrogen-containing saturated heterocyclic group" formed from $R^4$, $R^5$ and the adjacent nitrogen atom, when $R^4$ and $R^5$ combine together at the ends, is a pyrrolidinyl group, a morpholinyl group, a pyrrolidinyl group substituted by a hydroxy-lower alkyl group, a pyrrolidinyl group substituted by a hydroxyl group, a thiomorpholinyl group, a piperidyl group, a piperidyl group substituted by a hydroxyl group, a piperazinyl group substituted by a hydroxy-lower alkyl group, a piperidyl group substituted by a hydroxy-lower alkyl group, a piperazinyl group substituted by a lower alkyl group, a pyrrolidinyl group substituted by a lower alkoxycarbonylamino group, a piperidyl group substituted by an amino group optionally substituted by 1 to 2 lower alkyl groups, an oxopyrrolidinyl group, an oxomorpholinyl group, an oxothiomorpholinyl group, an oxopiperidyl group, an oxopiperazinyl group, or a piperidyl group substituted by a lower alkoxycarbonyl group; and the "saturated heterocyclic group" for Y is a piperidyl group.

4. The compound according to 3 above, wherein Ring B is a benzene ring optionally substituted by one or two groups selected independently from a halogen atom, an optionally substituted lower alkyl group, a hydroxy group, an optionally substituted lower alkoxy group, an oxy group substituted by an optionally substituted saturated heterocyclic group, a substituted carbonyl group, an optionally substituted amino group, a nitro group, a cyano group, a 4,5-dihydroxazolyl group and a group of the formula:

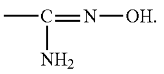

5. The compound according to 4 above, wherein the "optionally substituted lower alkyl group" as a substituent for Ring B is a lower alkyl group optionally substituted by a group selected from the followings:

(1) a lower alkoxycarbonyl group, (2) a carboxyl group, (3) a carbamoyl group optionally substituted by 1 to 2 groups selected from (a) a lower alkyl group, (b) a lower alkoxy-lower alkyl group, (c) a hydroxy-lower alkyl group, (d) an aminoalkyl group optionally substituted by 1 to 2 lower alkyl groups, and (e) a lower alkoxy group, (4) a carbonyl group substituted by a morpholinyl group, (5) a piperidylcarbonyl group substituted by a hydroxy-lower alkyl group, (6) a pyrrolidinylcarbonyl group substituted by a hydroxy-lower alkyl group, (7) a carbonyl group substituted by a hydroxyl group-substituted piperidyl group, (8) a hydroxyl group, and (9) a pyrrolidinylcarbonyl group;

the "optionally substituted lower alkoxy group" as a substituent for Ring B is a lower alkoxy group optionally substituted by a group selected from the followings:

(1) a carboxyl group, (2) a lower alkoxycarbonyl group, (3) a lower alkoxy group, (4) a hydroxyl group, (5) an aminooxy group optionally substituted by 1 to 2 lower alkoxycarbonyl groups,
(6) a lower alkoxy group substituted by a lower alkoxy group,
(7) a carbonyl group substituted by a group selected from morpholinyl group, a piperidyl group or a pyrrolidinyl group,
(8) a carbonyl group substituted by a hydroxypiperidyl group,
(9) a piperidylcarbonyl group substituted by a hydroxy-lower alkyl group,
(10) a pyrrolidinylcarbonyl group substituted by a hydroxy-lower alkyl group,
(11) a carbonyl group substituted by a lower alkyl-piperazinyl group,
(12) an amino group optionally substituted by 1 to 2 groups selected from (a) a lower alkyl group, (b) a lower alkoxy-carbonyl group, and (c) a lower alkanoyl group,
(13) a carbamoyl group optionally substituted by 1 to 2 groups selected from (a) a lower alkyl group, (b) a lower alkoxy-lower alkyl group, (c) a hydroxy-lower alkyl group, and (d) a lower alkyl group substituted by an amino group optionally substituted by 1 to 2 lower alkyl groups; and
(14) a group of the formula: —O—NH—C(=NH)$NH_2$;

the "oxy group substituted by an optionally substituted saturated heterocyclic group" as a substituent for Ring B is an oxy group substituted by a saturated heterocyclic group optionally substituted by an aromatic hydrocarbon group;

the "substituted carbonyl group" as a substituent for Ring B is a carbonyl group substituted by a group selected from the followings:
(1) a lower alkoxy group,
(2) a hydroxyl group,
(3) an amino group optionally substituted by 1 to 2 groups selected from (a) a lower alkyl group, (b) a lower alkoxy group, (c) a lower alkoxy-lower alkyl group, (d) a hydroxy-lower alkyl group, (e) a lower alkyl group substituted by an amino group optionally substituted by 1 to 2 lower alkyl groups, (f) a lower alkyl group substituted by an aromatic hydrocarbon group, and (g) a lower alkyl group substituted by a pyridyl group,
(4) a morpholinyl group, a pyrrolidinyl group, a piperidyl group or a thiomorpholinyl group,
(5) a hydroxypiperidyl group,
(6) a piperidyl group substituted by a hydroxy-lower alkyl group,
(7) a pyrrolidinyl group substituted by a hydroxy-lower alkyl group, and
(8) a lower alkyl-piperazinyl group;

the "optionally substituted amino group" as a substituent for Ring B is an amino group optionally substituted by 1 to 2 groups selected from the followings:
(1) a lower alkyl group,
(2) a lower alkoxy-lower alkyl group,
(3) a hydroxy-lower alkyl group,
(4) a lower alkanoyl group,
(5) a lower alkoxy-lower alkanoyl group,
(6) a hydroxy-lower alkanoyl group,
(7) a lower alkanoyl group substituted by a lower alkanoyloxy group,
(8) a lower alkanoyl group substituted by an amino group optionally substituted by 1 to 2 groups selected from (a) a lower alkyl group and (b) a lower alkanoyl group,
(9) a lower alkoxycarbonyl group,
(10) a lower alkoxycarbonyl group substituted by an aromatic hydrocarbon group,
(11) a carbamoyl group substituted by 1 to 2 lower alkyl groups,
(12) a lower alkylsulfonyl group, and
(13) a lower alkylsulfonyl group substituted by a morpholinyl group.

6. The compound according to 5 above, wherein Ring B is an unsubstituted benzene ring.

7. The compound according to 5 above, wherein Ring Z is a group of the formula:

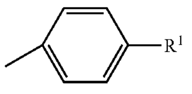

or

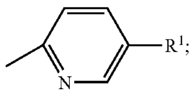

;

the formula:

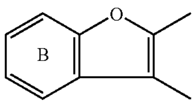

is

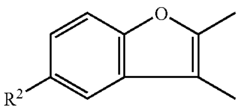

or

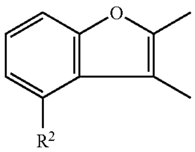

;

$R^1$ is a halogen atom or a lower alkyl group;

$R^2$ is a group selected from the followings:

A) a hydrogen atom, a cyano group, an amino group optionally substituted by 1 to 2 lower alkyl groups, a hydroxy group;

B) a lower alkyl group optionally substituted by a group selected from the followings:
(1) a lower alkoxycarbonyl group,
(2) a carboxyl group,
(3) a carbamoyl group optionally substituted by 1 to 2 groups selected from (a) a lower alkyl group, (b) a lower alkoxy-lower alkyl group, (c) a lower alkyl group substituted by a hydroxyl group, (d) a lower alkyl group substituted by an amino group optionally substituted by 1 to 2 lower alkyl groups, and (e) a lower alkoxy group,
(4) a carbonyl group substituted by a morpholinyl group,
(5) a piperidylcarbonyl group substituted by a hydroxy-lower alkyl group,
(6) a pyrrolidinylcarbonyl group substituted by a hydroxy-lower alkyl group,
(7) a carbonyl group substituted by a hydroxyl group-substituted piperidyl group,
(8) a hydroxyl group; and
(9) a pyrrolidinylcarbonyl group;

C) a lower alkoxy group optionally substituted by a group selected from the followings:
(1) a carboxyl group,
(2) a lower alkoxycarbonyl group,
(3) a lower alkoxy group,
(4) a hydroxyl group,
(5) an aminooxy group optionally substituted by 1 to 2 lower alkoxycarbonyl groups,
(6) a lower alkoxy group substituted by a lower alkoxy group,
(7) a carbonyl group substituted by a group selected from a morpholinyl group, a piperidyl group or a pyrrolidinyl group,
(8) a carbonyl group substituted by a hydroxypiperidyl group,
(9) a piperidylcarbonyl group substituted by a hydroxy-lower alkyl group,

(10) a pyrrolidinylcarbonyl group substituted by a hydroxy-lower alkyl group,
(11) a carbonyl group substituted by a lower alkyl-piperazinyl group,
(12) an amino group optionally substituted by 1 to 2 groups selected from (a) a lower alkyl group, (b) a lower alkoxy-carbonyl group, and(c) a lower alkanoyl group,
(13) a carbamoyl group optionally substituted by 1 to 2 groups selected from (a) a lower alkyl group, (b) a lower alkoxy-lower alkyl group, (c) a lower alkyl group substituted by a hydroxyl group, and (d) a lower alkyl group substituted by an amino group optionally substituted by 1 to 2 lower alkyl groups, and
(14) a group of the formula: —O—NH—C(=NH)$NH_2$; or
D) a carbonyl group substituted by a group selected from the followings:
(1) a lower alkoxy group,
(2) a hydroxyl group,
(3) an amino group optionally substituted by 1 to 2 groups selected from (a) a lower alkyl group, (b) a lower alkoxy group, (c) a lower alkoxy-lower alkyl group, (d) a hydroxy-lower alkyl group, (e) a lower alkyl group substituted by an amino group optionally substituted by 1 to 2 lower alkyl groups, (f) a lower alkyl group substituted by an aromatic hydrocarbon group, and (g) a lower alkyl group substituted by a pyridyl group,
(4) a morpholinyl group, a pyrrolidinyl group, a piperidyl group or a thiomorpholinyl group,
(5) a hydroxypiperidyl group,
(6) a piperidyl group substituted by a hydroxy-lower alkyl group,
(7) a pyrrolidinyl group substituted by a hydroxy-lower alkyl group, and
(8) a lower alkyl-piperazinyl group;
A is a single bond; and
$R^3$ is a hydrogen atom.

8. The compound according to 7 above, wherein $R^2$ is a group selected from the followings:
(1) a hydrogen atom,
(2) a cyano group,
(3) an amino group optionally substituted by 1 to 2 lower alkyl groups,
(4) a hydroxyl group,
(5) a lower alkoxy group,
(6) a lower alkoxy group substituted by a lower alkoxy group,
(7) a lower alkoxy group substituted by a hydroxyl group,
(8) a lower alkoxy group substituted by an amino group optionally substituted by 1 to 2 lower alkyl groups,
(9) a lower alkoxycarbonyl group,
(10) a carboxyl group,
(11) a carbonyl group substituted by an amino group optionally substituted by 1 to 2 groups selected from (a) lower alkyl group, (b) a hydroxy-lower alkyl group, (c) a lower alkoxy-lower alkyl group, and (d) a lower alkyl group substituted by an amino group optionally substituted by 1 to 2 lower alkyl groups,
(12) a morpholinylcarbonyl group, a pyrrolidinylcarbonyl group, a piperidylcarbonyl group or a thiomorpholinyl-carbonyl group,
(13) a piperidylcarbonyl group substituted by a hydroxy-lower alkyl group, or a pyrrolidinylcarbonyl group substituted by a hydroxy-lower alkyl group,
(14) a lower alkyl group,
(15) a lower alkyl group substituted by a lower alkoxycarbonyl group,
(16) a carboxy-lower alkyl group,
(17) a lower alkyl group substituted by a carbamoyl group optionally substituted by 1 to 2 groups selected from (a) a lower alkyl group, (b) a hydroxy-lower alkyl group, (c) a lower alkoxy-lower alkyl group, and (d) a lower alkyl group substituted by an amino group optionally substituted by 1 to 2 lower alkyl groups,
(18) a lower alkyl group substituted by a morpholinylcarbonyl group,
(19) a lower alkyl group substituted by a piperidylcarbonyl group substituted by a hydroxy-lower alkyl group, or a lower alkyl group substituted by a pyrrolidinylcarbonyl group substituted by a hydroxy-lower alkyl group,
(20) a hydroxy-lower alkyl group, and
(21) a lower alkyl group substituted by a pyrrolidinyl-carbonyl group.

9. The compound according to 7 above, wherein $R^2$ is a group selected from the followings:
(1) a hydrogen atom,
(2) a carbonyl group substituted by an amino group optionally substituted by 1 to 2 groups selected from (a) a lower alkyl group and (b) a lower alkoxy-lower alkyl group,
(3) a lower alkoxycarbonyl group,
(4) a morpholinylcarbonyl group, a pyrrolidinylcarbonyl group, a piperidylcarbonyl group or a thiomorpholinyl-carbonyl group,
(5) a lower alkyl group substituted by a carbamoyl group substituted by 1 to 2 lower alkyl groups,
(6) a carboxy-lower alkyl group,
(7) a lower alkyl group substituted by a morpholinylcarbonyl group,
(8) a hydroxy-lower alkyl group,
(9) a lower alkyl group substituted by a pyrrolidinyl-carbonyl group, and
(10) a lower alkyl group substituted by a carbamoyl group optionally substituted by 1 to 2 groups selected from (a) a lower alkyl group substituted by an amino group optionally substituted by 1 to 2 lower alkyl groups and (b) lower alkyl group.

10. The compound according to 7 above, wherein $R^2$ is a group selected from the followings:
(1) a hydrogen atom,
(2) a hydroxy-lower alkyl group,
(3) a carboxy-lower alkyl group,
(4) a lower alkoxy group substituted by a lower alkoxy group;
(5) a carbonyl group substituted by a group selected from (a) an amino group optionally substituted by 1 to 2 lower alkyl groups, and (b) a morpholinyl group;
(6) a carbamoyl group substituted by 1 to 2 groups selected from (a) a lower alkoxy-lower alkyl group and (b) a lower alkyl group;
(7) a lower alkyl group substituted by a carbamoyl group substituted by 1 to 2 groups selected from (a) a lower alkoxy-lower alkyl group and (b) a lower alkyl group;
(8) a carbamoyl group substituted by 1 to 2 groups selected from (a) a lower alkyl group substituted by an amino group optionally substituted by 1 to 2 alkyl groups and (b) a lower alkyl group,
(9) a lower alkyl group substituted by a carbamoyl group substituted by 1 to 2 groups selected from (a) an amino-lower alkyl group optionally substituted 1 to 2 alkyl groups and (b) a lower alkyl group,
(10) a lower alkyl group substituted by a pyrrolidinyl-carbonyl group; and
(11) a carbamoyl-lower alkyl group optionally substituted by 1 to 2 groups selected from (a) a lower alkyl group substituted by an amino group optionally substituted by 1 to 2 lower alkyl groups and (b) a lower alkyl group.

11. A compound of the formula:

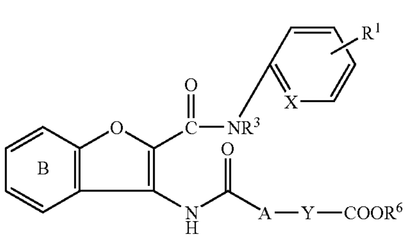

wherein X is a group of the formula: —N= or —CH=;

A is a single bond or a group of the formula: -NH-;

Y is a lower alkylene group, a cycloalkanediyl group, a phenyl group or a saturated heterocyclic group;

$R^6$ is a protecting group for carboxyl group;

$R^1$ is a hydrogen atom, a halogen atom, a lower alkyl group, a lower alkoxy group, a cyano group, or an amino group optionally substituted by 1 to 2 lower alkyl groups;

Ring B of the formula:

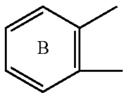

is an optionally substituted benzene ring; and $R^3$ is a hydrogen atom or a lower alkyl group.

12. A compound of the formula:

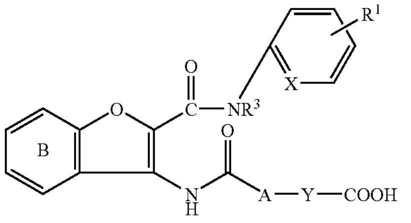

wherein X is a group of the formula: —N= or —CH=;

A is a single bond or a group of the formula: —NH—;

Y is a lower alkylene group, a cycloalkanediyl group, a phenyl group or a saturated heterocyclic group;

$R^1$ is a hydrogen atom, a halogen atom, a lower alkyl group, a lower alkoxy group, a cyano group, or an amino group optionally substituted by 1 to 2 lower alkyl groups;

Ring B of the formula:

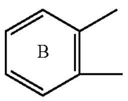

is an optionally substituted benzene ring; and $R^3$ is a hydrogen atom or a lower alkyl group.

13. The compound according to 11 or 12 above, wherein the formula:

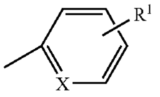

is

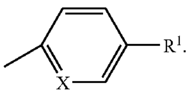

14. The compound according to 5 above, wherein Ring Z is a group of the formula:

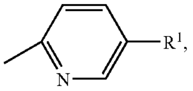

$R^1$ is a halogen atom;

$R^3$ is a hydrogen atom;

the formula:

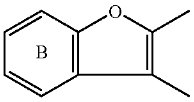

is

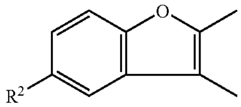

or

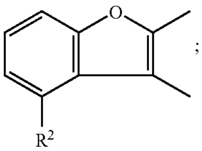

;

$R^2$ is a carbonyl group substituted by a group selected from the followings:

(1) a lower alkoxy group, (2) a hydroxyl group, (3) an amino group optionally substituted by 1 to 2 groups elected from (a) a lower alkyl group, (b) a lower alkoxy group, (c) a lower alkoxy-lower alkyl group, (d) a hydroxy-lower alkyl group, (e) a lower alkyl group substituted by an amino group optionally substituted by 1 to 2 lower alkyl groups, (f) a lower alkyl group substituted by an aromatic hydrocarbon group, and (g) a lower alkyl group substituted by a pyridyl group, (4) a morpholinyl group, a pyrrolidinyl group, a piperidyl group or a thiomorpholinyl group, (5) a hydroxypiperidyl group, (6) a piperidyl group substituted by a hydroxy-lower alkyl group, (7) a pyrrolidinyl group substituted by a hydroxy-lower alkyl group, and (8) a lower alkyl-piperazinyl group;

A is a single bond;

Y is a cyclohexanediyl group; and $R^4$ and $R^5$ are independently a lower alkyl group, or $R^4$, $R^5$ and the adjacent nitrogen atom, when $R^4$ and $R^5$ combine together at the ends, form a pyrrolidinyl group, a morpholinyl group, a pyrrolidinyl group substituted by a hydroxy-lower alkyl group, a pyrrolidinyl group substituted by a hydroxyl group, a thiomorpholinyl group, a piperidyl group, a piperidyl group substituted by a hydroxyl group, a piperazinyl group substituted by a hydroxy-lower alkyl group, a piperidyl group substituted by a hydroxy-lower alkyl group, a piperazinyl group substituted by a lower alkyl group, a pyrrolidinyl group substituted by a lower alkoxycarbonylamino group, a piperidyl group substituted by an amino group optionally substituted by 1 to 2 lower alkyl groups, an oxopyrrolidinyl group, an oxomorpholinyl group, an oxothiomorpholinyl group, an oxopiperidyl group, an oxopiperazinyl group, or a piperidyl group substituted by a lower alkoxycarbonyl group.

15. The compound according to 14 above, wherein $R^2$ is a carbonyl group substituted by a group selected from the followings:

(1) an amino group optionally substituted by 1 to 2 groups selected from (a) a lower alkyl group, (b) a lower alkoxy group, (c) a lower alkoxy-lower alkyl group, (d) a hydroxy-lower alkyl group, (e) a lower alkyl group substituted by an amino group optionally substituted by 1 to 2 lower alkyl group, (f) a lower alkyl group substituted by an aromatic hydrocarbon group, and (g) a lower alkyl group substituted by a pyridyl group, and (2) a morpholin-4-yl group, a pyrrolidin-1-yl group, a piperidin-1-yl group a piperazin-1-yl group or a thiomorpholin-4-yl group;

$R^4$ and $R^5$ are independently a lower alkyl group, or $R^4$, $R^5$ and the adjacent nitrogen atom, when $R^4$ and $R^5$ combine together at the ends, form a pyrrolidin-4-yl group.

16. The compound according to 15 above, wherein the formula:

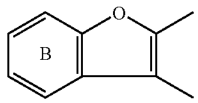

is

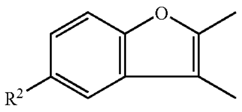

;

$R^2$ is a carbonyl group substituted by a group selected from the followings:

(1) an amino group optionally substituted by 1 to 2 groups selected from (a) a lower alkyl group and (b) a lower alkoxy-lower alkyl group, and (2) a morpholin-4-yl group.

17. Methyl 2-{[(5-chloropyridin-2-yl)amino]carbonyl}-3-[({trans-4-[(dimethylamino)carbonyl]cyclohexyl}-carbonyl)amino]benzofuran-5-carboxylate;

Methyl [2-{[(5-chloropyridin-2-yl)amino]carbonyl}-3-({[trans-4-(pyrrolidin-1-ylcarbonyl)cyclohexyl]carbonyl}-amino)benzofuran-5-yl]acetate;

$N^2$-(5-Chloropyriclin-2-yl)-$N^5$,$N^5$-dimethyl-3-({[trans-4-(morpholin-4-ylcarbonyl)cyclohexyl]carbonyl}amino)-benzofuran-2,5-dicarboxamide;

N-(5-Chloropyridin-2-yl)-3-[(5-morpholin-4-yl-5-oxopentanoyl)amino]benzofuran-2-carboxamide;

2-{[(5-Chloropyridin-2-yl)amino]carbonyl}-3-[({trans-4-[(dimethylamino)carbonyl]cyclohexyl}carbonyl)amino]-benzofuran-5-carboxylic acid;

$N^2$-(5-Chloropyridin-2-yl)-3-[({trans-4-[(dimethylamino) carbonyl]cyclohexyl}carbonyl)amino]-$N^5$,$N^5$-dimethyl-benzofuran-2,5-dicarboxamide;

trans-N'-[2-{[(5-Chloropyridin-2-yl)amino]carbonyl}-5-(morpholin-4-ylcarbonyl)benzofuran-3-yl]-N,N-dimethyl-cyclohexane-1,4-dicarboxamide, or a pharmaceutically acceptable-salt thereof.

18. A pharmaceutical composition, which comprises as an active ingredient a compound according to any one of 1 to 17 above, or a pharmaceutically acceptable salt thereof.

19. A method for treatment of thrombosis, which comprises administering an effective amount of a compound according to any one of 1 to 17 above, or a pharmaceutically acceptable salt thereof, to a patient in need thereof.

20. Use of a compound according to any one of 1 to 17 above, or a pharmaceutically acceptable salt thereof, to a patient in need thereof in treatment of patients suffering from thrombosis.

BEST MODE FOR CARRYING OUT THE INVENTION

The compound [1] of the present invention will be hereinafter described in detail.

The term "lower" used in the definition of the formulas herein described means unless otherwise noted a straight- or branched-carbon chain having 1 to 6 carbon atoms.

Thus, examples of "lower alkyl group" include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methyl-propyl, and the like. Among them, alkyl groups having 1 to 4 carbon atoms, for example, methyl, ethyl, propyl, isopropyl, butyl, isobutyl, sec-butyl and tert-butyl are commonly used.

The term "lower alkoxy group" means a substituent wherein an oxygen atom is bound to the above-mentioned alkyl group. Among them, alkoxy groups having 1 to 4 carbon atoms, for example, and methoxy, ethoxy, propoxy, isopropoxy, butoxy, isobutoxy, sec-butoxy and tert-butoxy groups are commonly used.

Examples of "lower alkylene group" include a straight- or branched-chain alkylene group having 1 to 6 carbon atoms, specifically, methylene, ethylene, trimethylene, tetra-methylene, pentamethylene, hexamethylene, and the like. Among them, an alkylene group having 1 to 5 carbon atoms is commonly used.

Examples of "lower alkanoyl group" include alkanoyl groups formed by removing a "OH" group from the carboxyl group of a lower carboxylic acid. Specifically, formyl, acetyl, propionyl, butyryl, and the like are commonly used.

The "saturated heterocyclic group" means a saturated heterocyclic group containing 1 to 4 hetero atoms selected independently from the group consisting of nitrogen atom, oxygen atom and sulfur atom, preferably a 4- to 14-membered heterocyclic group containing 1 to 4 hetero atoms selected independently from the group consisting of nitrogen atom, oxygen atom and sulfur atom, including condensed rings. Specific examples include imidazolidinyl, pyrazolidinyl, piperidyl, piperazinyl, morpholinyl, thiomorpholinyl, homopiperazinyl, homopiperidyl, pyrrolidinyl, oxazolidinyl, 1,3-dioxanyl, and the like. Above all, piperidyl, piperazinyl, homopiperazinyl, pyrrolidinyl and morpholinyl are commonly used. Further, they are used as a divalent group when used for the group: Y.

The "nitrogen-containing saturated heterocyclic group" means a saturated ring containing 1 to 4 hetero atoms, which ring may contain, in addition to nitrogen atom, oxygen atom and/or sulfur atom, preferably, a 4 to 14-membered saturated heterocyclic group containing, as hetero atom, only nitrogen atom or both nitrogen atom and oxygen atom, including condensed rings. Examples thereof include imidazolidinyl, pyrazolidinyl, piperidyl, piperazinyl, morpholinyl, thiomorpholinyl, homopiperazinyl, homopiperidyl, pyrrolidinyl, oxazolidinyl, and the like, specifically, piperidyl, piperazinyl, homopiperazinyl, pyrrolidinyl, and morpholinyl are commonly used.

Examples of "halogen atom" include fluorine, chlorine, bromine or iodine atom. Above all, fluorine, chlorine or bromine atom is commonly used.

Examples of "cycloalkanediyl group" include 3- to 7-membered cycloalkanediyl group such as 1,4-cyclohexanediyl group.

Examples of "aromatic hydrocarbon group" include phenyl group and naphthyl group, and phenyl group is commonly used.

The pharmaceutically acceptable salt of the compound [1] includes a salt with an inorganic acid such as hydrochloric acid, hydrobromic acid, hydroiodic acid, sulfuric acid, nitric acid, phosphoric acid, and the like; a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, and the like; salt with an acidic amino acid such as aspartic acid, glutamic acid, and the like; salt with a metal such as sodium, potassium, magnesium, calcium, aluminium, and the like; salt with an organic base such as methylamine, ethylamine, ethanolamine, and the like; or a salt with a basic amino acid such as lysine, ornithine, and the like.

The compound [1] of the present invention can be in the form of quaternary ammonium salt and such a quaternary ammonium salt falls within the scope of the present compound [1].

Further, the compound [1] of the present invention includes an intramolecular salt, hydrate, solvate or crystalline polymorphism, and the like.

Besides, when the compound [1] has an asymmetric carbon atom(s), it can exist as an optical isomer, and the present invention encompass those isomers and a mixture thereof. Further, when the compound [1] has a double bond and/or a ring to which a cycloalkanediyl group having two or more substituents is attached, it may exist in the form of cis or trans, and the present invention encompass those isomers and a mixture thereof.

Additionally, the compound [1] of the present invention encompasses a prodrug of a compound as mentioned above. Examples of a prodrug include those prepared by protecting a functional group such as an amino or carboxy group of a compound [1] above with a conventional protecting group.

The compound of the present invention may be prepared by the following processes.

[Process A]

Among the compounds [1] of the present invention, a compound wherein A is a single bond, i.e., a compound of the formula [1-A]:

[1-A]

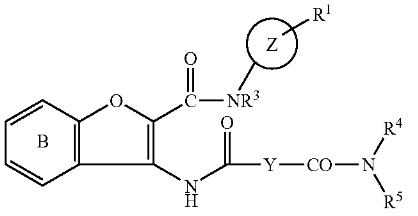

wherein the symbols are the same as defined above can be prepared by reacting an amino compound of the formula [2]:

[2]

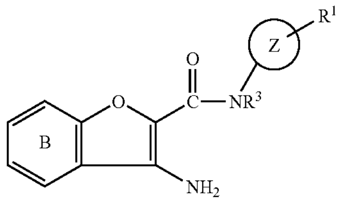

wherein the symbols are the same as defined above, with a carboxylic acid compound of the formula [3-A1]:

HOOC—Y—CO—N($R^4$)($R^5$) [3-A1]

wherein the symbols are the same as defined above, or a reactive derivative thereof at its carboxyl group.

[Process B]

The compound [1-A] can also be prepared by reacting the compound [2] with a compound of the formula [3-A2]:

HOOC—Y—COO$R^6$ [3-A2]

wherein $R^6$ is a protecting group for carboxyl group and the other symbol is the same as defined above, or a reactive derivative thereof at its carboxyl group, to give a compound of the formula [2-A1]:

[2-A1]

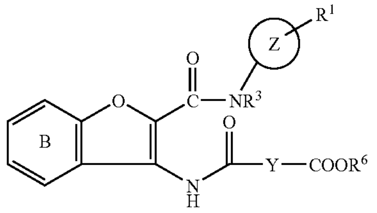

wherein the symbols are the same as defined above, removing the protecting group for carboxyl group to give a compound of the formula [2-A2]:

[2-A2]

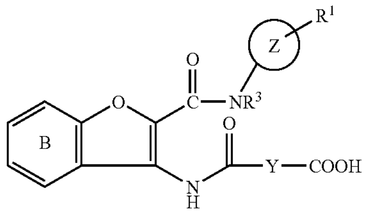

wherein the symbols are the same as defined above, and reacting the compound [2-A2] with a compound of the formula: [3-A3]:

HN($R^4$)($R^5$) [3-A3]

wherein the symbols are the same as defined above.

[Process C]

Among the compounds [1] of the present invention, those wherein A is a group of the formula: —NH—, i.e., a compound of the formula [1-B]:

[1-B]

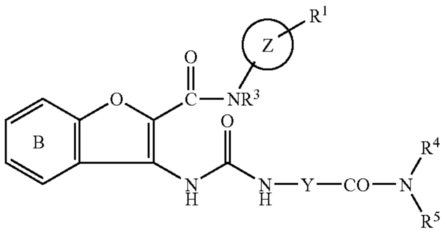

wherein the symbols are the same as defined above can be prepared by reacting the above-mentioned compound [2] with a compound of the formula [3-B1]:

$H_2N—Y—COOR^6$ [3-B 1]

wherein the symbols are the same as defined above and a compound of the formula [3-B2]:

$L^1—CO—L^2$ [3-B2]

wherein $L^1$ and $L^2$ are the same or different and each a leaving group to give a compound of the formula [2-B1]:

[2-B1]

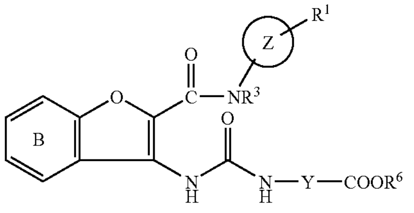

wherein the symbols are the same as defined above, removing the protecting group for carboxyl group to give a compound of the formula [2-B2]:

[2-B2]

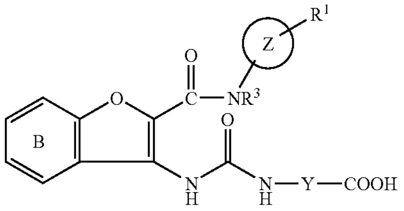

wherein the symbols are the same as defined above, and reacting the compound [2-B2] with the compound [3-A3].

The compound [1] can also be prepared, if necessary, through the mutual conversion, wherein a substituent(s) of resulting compound [1-A] or [1-B] is adequately converted into a compound [1] through the mutual conversion by alkylation, reductive alkylation, amidation, sulfonyl-amidation, reduction, dealkylation, hydrolysis, quaternary amination, formylation, protection or deprotection of amino or carboxyl group, and the like.

[Manufacturing Process for Starting Materials: Preparation of Compound [2]]

The compound [2] can be prepared by a process comprising:

converting the aldehyde group of a compound of the formula [10]:

[10]

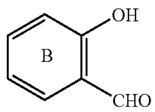

wherein the symbols are the same as defined above, into cyano group to give a compound of the formula [9]:

[9]

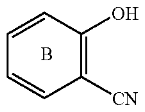

wherein the symbols are the same as defined above, reacting the compound [9] with a compound of the formula [8]:

[8]

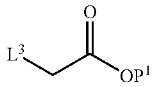

wherein $L^3$ is a leaving group and $P^1$ is a protecting group for carboxyl group, to give a compound of the formula [7]:

[7]

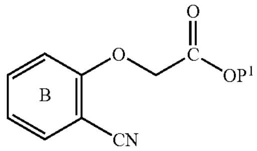

wherein the symbols are the same as defined above, removing the protecting group $P^1$ of the compound [7] to give a compound of the formula [6]:

[6]

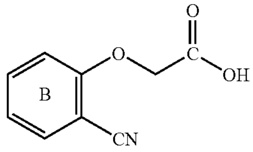

wherein the symbols are the same as defined above, reacting the compound [6], if necessary, after converting into a reactive derivative at the carboxyl group thereof, with a compound of the formula [5]:

[5]

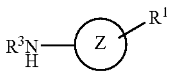

wherein the symbols are the same as defined above, to give a compound of the formula [4]:

[4]

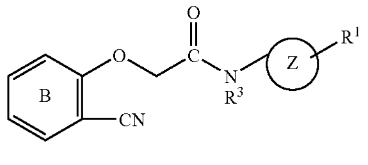

wherein the symbols are the same as defined above, and subjecting the compound [4] to cyclization.

Further, the compound [4] can be prepared by reacting a compound of the formula [9] with a compound of the formula [12]:

[12]

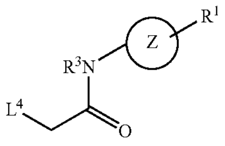

wherein $L^4$ is a leaving group and the other symbols are the same as defined above.

The compound [4] can also be prepared by reacting a compound of the formula [13]:

[13]

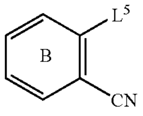

wherein $L^5$ is a leaving group and the other symbols are the same as defined above with a compound of the formula [14]:

[14]

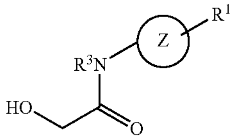

wherein the symbols are the same as defined above.

Further, the compound of the formula [10] can be prepared by formylating a compound of the formula [11]:

[11]

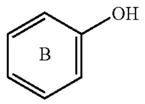

wherein the symbols are the same as defined above.

The Processes [A]-[C] above can be carried out in the following manner.

[Process A]

The reaction where a compound [1-A] is prepared using a compound [2] and a compound [3-A1] or a reactive derivative thereof at its carboxyl group can be carried out in a conventional manner for amidation. That is, the reaction can be carried out by reacting a compound [2] with a compound [3-A1] or a reactive derivative thereof, or a salt thereof in the presence or absence of a condensing agent, and if necessary, in the presence of an acid scavenger, in an appropriate solvent.

The condensing agent includes conventional agents such as N,N-dicyclohexylcarbodiimide (DCC), 1-ethyl-3-(3-dimethylaminopropyl)carbodiimide (EDC) or a hydrochloride thereof, carbonyldiimidazole (CDI), diphenylphosphorylazide (DPPA), diethyl cyanophosphonate (DEPC), and the like. Above all, DCC, EDC or a hydrochloride thereof is preferred.

Examples of the reactive derivative of the compound [3-A1] include those conventionally used such as an acid halide, a mixed anhydride, a reactive ester, and the like. Examples of an activator that can be used for converting the compound [3-A1] into the reactive derivative thereof include thionyl chloride, thionyl bromide, oxalyl chloride, N-hydroxylamines such as 1-hydroxysuccinimide, 1-hydroxybenzotriazole, and the like, and phenols such as p-nitrophenol, and the like. Above all, thionyl chloride, oxalyl chloride, 1-hydroxysuccinimide and 1-hydroxybenzotriazole are preferred. The acid chloride method is especially preferable.

Examples of the salt of a compound [3-A1] or a reactive derivative of the compound [3-A1] include a salt with an inorganic acid such as hydrochloric acid, hydrobromic acid, sulfuric acid, and the like. An acid scavenger is also usable depending on the method to be employed, which includes inorganic or organic bases.

The present reaction may be facilitated when it is carried out in the presence of a base or by using such a base as a solvent. Examples of inorganic bases include alkali metal carbonates (sodium carbonate, potassium carbonate, cesium carbonate, and the like.), alkali earth metal carbonates (calcium carbonate, and the like.), alkali metal hydrogen carbonates (sodium hydrogen carbonate, potassium hydrogen carbonate, and the like.), alkali metal hydroxides (sodium hydroxide, potassium hydroxide, lithium hydroxide, and the like). Examples of organic bases include tri-lower alkylamines (triethylamine, tributylamine, diisopropylethylamine, and the like), tertiary-amines (1,4-diazabicyclo[2.2.2]octane, 1,5-diazabicyclo[4.3.0]non-5-ene, 1,8-diazabicyclo[5.4.0]undec-7-ene, and the like), amines (N,N-dimethylaniline, N,N-diethylaniline, 4-dimethylaminopyridine, and the like), pyridine, lutidine, collidine, and the like. Above all, triethylamine, diisopropylethylamine, 4-dimethylaminopyridine, or pyridine is preferred for carrying out the reaction. The present reaction can be carried out in the presence or absence of a solvent, preferably in the presence of a solvent.

Examples of the solvent include any inert solvent which does not disturb the reaction, such as halogenated hydrocarbons (chloroform, dichloromethane, dichloroethane, and the like), aromatic hydrocarbons (benzene, toluene, xylene, and the like), ethers (diethyl ether, diisopropyl ether, tetrahydrofuran, dioxane, 1,2-dimethoxyethane, and the like), esters (ethyl acetate, and the like), amides (N,N-dimethylformamide, N,N-dimethylacetamide, 1,3-dimethyl-2-imidazolidinone, and the like), nitrites (acetonitrile, and the like), dimethylsulfoxide, pyridine, 2,6-luthidine, and the like, a mixed solvent comprising two or more of these solvents, if necessary, and also a mixture of any one(s) of these solvents and water. It is preferred to select any appropriate solvent depending on the method used. Above all, dichloromethane, chloroform, toluene, xylene, tetrahydrofuran, dioxane, N,N-dimethylformamide, N,N-dimethylacetamide, 1,3-dimethyl-2-imidazolidinone, pyridine, and the like are preferred, and dichloromethane, chloroform, N,N-dimethylformamide and pyridine are especially preferred. The present reaction can be carried out in a wide range of temperature from a temperature of under cooling to under heating. For example, the reaction can be preferably carried out at a temperature of −10° C. to the boiling point of the reaction mixture, especially from under ice-cooling to 60° C.

[Process B]

The reaction between the compound [2] and a compound [3-A2] or a reactive derivative thereof at the carboxyl group can be carried out in a similar manner to the reaction between the compound [2] and a compound [3-A1] or a reactive derivative thereof at the carboxyl group. The removal of a protecting group at the carboxyl group of compound [2-A1] can be carried out in a conventional manner. The next reaction with a compound [3-A3] can be carried out in a similar manner to the reaction between the compound [2] and a compound [3-A1].

[Process C]

The process wherein the compound [2-B1] is prepared by reacting a compound [2] with compounds of the formulas [3-B1] and [3-B2] can be carried out in accordance with a conventional method for carbonylation in the presence of an appropriate acid scavenger in an appropriate solvent.

Examples of a leaving group for a compound of the formula [3-B2] include a halogen atom. Examples of a compound [3-B2] include phosgene, triphosgene, CDI, and the like, and triphosgene is preferred.

Examples of acid scavenger used in the reaction include both the inorganic and organic bases. Examples of inorganic bases include alkali metal carbonates (sodium carbonate, potassium carbonate, cesium carbonate, and the like) and alkali metal hydrogen carbonates (sodium hydrogen carbonate, potassium hydrogen carbonate, and the like). Examples of organic bases include tri-lower alkylamines (triethylamine, tributylamine, diisopropylethylamine, and the like), tertiary-amines (1,4-diazabicyclo[2.2.2]octane, 1,5-diazabicyclo[4.3.0]non-5-ene, 1,8-diazabicyclo[5.4.0]-undec-7-ene, and the like), amines (N,N-dimethylaniline, N,N-diethylaniline, 4-dimethylaminopyridine, and the like), pyridine, lutidine, collidine, and the like. Above all, triethylamine, diisopropylethylamine, 4-dimethylaminopyridine and pyridine are preferred.

Examples of the solvent include any inert solvent which does not disturb the reaction, such as halogenated hydrocarbons (chloroform, dichloromethane, dichloroethane, and the like), ethers (diethyl ether, diisopropyl ether, tetrahydrofuran, dioxane, 1,2-dimethoxyethane, and the like), esters (ethyl acetate, and the like), amides (N,N-dimethylformamide, N,N-dimethylacetamide, 1,3-dimethyl-2-imidazolidinone, and the like), nitriles (acetonitrile, and the like), pyridine, 2,6-luthidine, and the like, and a mixed solvent comprising two or more of these solvents, if necessary. It is preferred to select any appropriate solvent depending on the method used. Above all, dichloromethane, tetrahydrofuran, N,N-dimethylformamide, N,N-dimethylacetamide, 1,3-dimethyl-2-imidazolidinone, pyridine, and the like are preferred, and dichloromethane and N,N-dimethylformamide are especially preferred. The present reaction can be carried out in a wide range of temperature from −78° C. to the boiling point of the reaction mixture. For example, the reaction can be preferably carried out at a temperature of −10° C. to the boiling point of the reaction mixture, especially at a temperature of under ice-cooling to room temperature.

The removal of a protecting group at the carboxyl group of compound [2-B1] can be carried out in a conventional manner, for example, by hydrolysis in the presence of an acid such as trifluoroacetic acid, and the like. The next reaction with a compound [3-A3] can be carried out in a similar manner to the reaction between the compound [2] and a compound [3-A1].

Furthermore, after carrying out the Processes [A], [B], [C], the objective compound [1] can also be obtained, if necessary, through a mutual conversion by conducting the following reaction(s), on condition that the resulting compound of the formula [1-A] or [1-B] has one or more moieties available to further reaction(s) in the substituent(s) (mainly referring to, for example, a protecting group for amine, alcoholic or phenolic OH, ester, carboxylic acid, nitro, halogen, and the like).

The reactions for amidation, reduction and hydrolysis, among the reactions to be conducted when needed, can be carried out as follows.

The amidation can be carried out in a manner similar to the above-mentioned reaction between a compound [2] and a compound [3-A1], when needed.

The reduction can be carried out in a conventional manner, when needed. For example, the reaction can be carried out by reacting a compound [1] with an appropriate reducing agent, or with hydrogen in the presence of a metal catalyst in an appropriate solvent.

In the reaction, any conventional reducing agents can be used without limitation; however, metal hydride reducing agents such as lithium aluminium hydride, lithium borohydride, sodium borohydride, and the like, metals such as zinc, iron, stannum, and the like, and metal salts such as tin chloride, and the like are preferred, and metals such as stannum, and the like and metal salts such as tin chloride, and the like are more preferred. In the catalytic hydrogenation, any conventional metal catalysts can be used without limitation; however, palladium-carbon, Raney Nickel, Raney Cobalt, platinum oxide, and the like are preferred and metals such as Raney Nickel, and the like are more preferred. Furthermore, depending on the method used, the reaction can sometimes be facilitated when it is carried out under an acidic condition in the co-existence of a mineral acid such as hydrochloric acid, and the like In the reaction where a metal hydride reducing agent is used, any inert solvents which do not disturb the reaction can be used without limitation, and examples thereof include ethers (diethyl ether, diisopropyl ether, tetrahydrofuran, dioxane, 1,2-dimethoxyethane, and the like), amides (N,N-dimethylformamide, N,N-dimethylacetamide, 1,3-dimethyl-2-imidazolidinone, and the like), aromatic hydrocarbons (benzene, toluene, xylene, and the like), alcohols (methanol, ethanol, propanol, and the like), water, and the like, and a mixed solvent comprising two or more of these solvents, if necessary. It is preferred to select any appropriate solvent depending on the method used.

In the reaction where a metal such as zinc, iron, stannum, and the like, or a metal salt such as tin chloride, and the like is used, any inert solvents which do not disturb the reaction can be used without limitation, and examples thereof include water, alcohols (methanol, ethanol, propanol, and the like), esters (ethyl acetate, and the like), ethers (diethyl ether, diisopropyl ether, tetrahydrofuran, 1,2-dimethoxyethane, and the like), amides (N,N-dimethylformamide, N,N-dimethylacetamide, 1,3-dimethyl-2-imidazolidinone, and the like), nitrites (acetonitrile, and the like), aromatic hydrocarbons (benzene, toluene, xylene, and the like), and a mixed solvent comprising two or more of these solvents, if necessary. It is preferred to select any appropriate solvent depending on the method used. Above all, ethyl acetate, water, or a mixed solvent comprising water and an alcohol, an ether, an amide, a nitrile and the like is preferred.

In the reaction where hydrogenation is carried out in the presence of a metal catalyst, any inert solvents which do not disturb the reaction can be used without limitation, and examples thereof include alcohols, ethers, aliphatic hydrocarbons, aromatic hydrocarbons, amides, esters (ethyl acetate, and the like), organic acids (formic acid, acetic acid, propionic acid, trifluoroacetic acid, and the like), and a mixed solvent comprising two or more of these solvents, if necessary. It is preferred to select any appropriate solvent depending on the method used.

The present reaction can be carried out in a wide range of temperature from a temperature of under cooling to under heating. For example, the reaction can be preferably carried out at a temperature of −10° C. to the boiling point of the reaction mixture.

The hydrogen pressure used in the catalytic hydrogenation reaction is generally about 1-100 atm.

The reaction time for the present reaction varies depending on the kind of the reducing agent or the activity of the catalyst used; however, it is generally between is about 10 minutes and 24 hours.

The hydrolysis can be carried out in a conventional manner, when needed.

The protection and deprotection of amino or carboxyl group can be carried out according to any one of known methods, when needed.

The mutual conversion of a compound [1] by alkylation, reductive alkylation, sulfonyl-amidation, dealkylation, quaternary amination, formylation, and the like, can be conducted properly using any one of known methods.

[Manufacturing Process for Starting Materials: Preparation of Compound [2]]

(1) The reaction for converting the aldehyde group of the compound [10] into a cyano group to give the compound [9] can be carried out by reacting the compound [10] with a hydroxylamine or hydrochloride thereof in the presence or absence of sodium formate in an appropriate solvent. A dehydrating agent may be added. The solvent available includes an organic lower fatty acid such as formic acid; however, it is preferred to select an appropriate solvent depending on the method used.

The present reaction can be carried out in a wide range of temperature from a temperature of under cooling to under heating. For example, the reaction can be preferably carried out at a temperature of under ice-cooling to the boiling point of the reaction mixture, especially at the boiling point of the reaction mixture.

(2) The next reaction between the resulting compound [9] and the compound [8] to give the compound [7] can be carried out in a conventional manner for O-alkylation of a phenol compound. The present reaction can be carried out by reacting the compound [9] with the compound [8] in an appropriate solvent in the presence of a base or by using such a base as the solvent.

The leaving group in the compound [8] can be preferably, for example, a halogen atom. Examples of a preferred protecting group for the carboxyl group of the compound [8] include a lower alkyl group and a phenyl-lower alkyl group.

Examples of the base usable include both the inorganic and organic bases such as alkali metal carbonates (sodium carbonate, potassium carbonate, and the like), alkali metal hydrogen carbonates (sodium hydrogen carbonate, potassium hydrogen carbonate, and the like), alkali metal hydroxides (sodium hydroxide, potassium hydroxide, lithium hydroxide, and the like), alkali metal hydrides (sodium hydride, and the like), alkali metal alkoxides (sodium methoxide, potassium t-butoxide, and the like), tri-lower alkylamines (triethylamine, tributylamine, diisopropylethylamine, and the like), tertiary-amines (1,4-diazabicyclo [2.2.2]octane, 1,5-diazabicyclo[4.3.0]non-5-ene, 1,8-diazabicyclo[5.4.0]-undec-7-ene, and the like), amines (N,N-dimethylaniline, N,N-diethylaniline, 4-dimethylaminopyridine, and the like), pyridine, lutidine, collidine, and the like. Above all, alkali metal carbonate, diisopropylethylamine, pyridine, and the like are preferred.

Examples of the solvent include any inert solvent which does not disturb the reaction, such as ketones (e.g., acetone, methylethyl ketone, and the like), aromatic hydrocarbons (benzene, toluene, xylene, and the like), ethers (diethyl ether, diisopropyl ether, tetrahydrofuran, dioxane, 1,2-dimethoxyethane, and the like), amides (N,N-dimethylformamide, N,N-dimethylacetamide, 1,3-dimethyl-2-imidazolidinone, and the like), nitriles (acetonitrile, and the like), alcohols (methanol, ethanol, propanol, 2-butanol, and the like), dimethylsulfoxide, pyridine, 2,6-luthidine, and the like, and a mixed solvent comprising two or more of these solvents, if necessary. Above all, ketones such as acetone, methylethyl ketone, and the like, and amides such as N,N-dimethylformamide, N,N-dimethylacetamide, 1,3-dimethyl-2-imidazolidinone, and the like are preferred.

The present reaction can be carried out in a wide range of temperature from a temperature of under cooling to under heating. For example, the reaction can be preferably carried out at a temperature of under ice-cooling to the boiling point of the reaction mixture.

An alkali metal iodide such as lithium iodide, sodium iodide, potassium iodide, and the like can also be added, which may facilitate the reaction.

(3) The reaction for removing a protecting group from the compound [7] to give the compound [6] can be carried out by a method generally used for the deprotection of carboxyl group.

(4) The reaction between the compound [5] and the compound [6] to give the compound [4] can be carried out in a manner similar to that for reacting the compound [2] with the compound [3-A].

(5) The reaction for cyclizing the compound [4] to give the compound [2] can be carried out by treating the compound [4] with a base in an appropriate solvent.

Examples of the base usable include both the inorganic and organic bases such as alkali metal carbonates (sodium carbonate, potassium carbonate, and the like), alkali metal hydroxides (sodium hydroxide, potassium hydroxide, lithium hydroxide, and the like), alkali metal hydrides (sodium hydride, and the like), alkali metal alkoxides (sodium methoxide, potassium t-butoxide, and the like), tri-lower alkylamines (triethylamine, tributylamine, diisopropylethylamine, and the like), tert-amines (1,4-diazabicyclo[2.2.2]octane, 1,5-diazabicyclo[4.3.0]-non-5-ene, 1,8-diazabicyclo[5.4.0]undec-7-ene, and the like), amines (N,N-dimethylaniline, N,N-diethylaniline, 4-dimethylaminopyridine, and the like), pyridine, lutidine, collidine, and the like.

The present reaction can be carried out in the presence or absence of a solvent, preferably in the presence of a solvent. Examples of the solvent include any inert solvent which does not disturb the reaction, such as aromatic hydrocarbons (benzene, toluene, xylene, and the like), ethers (diethyl ether, diisopropyl ether, tetrahydrofuran, dioxane, 1,2-dimethoxyethane, and the like), amides (N,N-dimethylformamide, N,N-dimethylacetamide, 1,3-dimethyl-2-imidazolidinone, and the like), nitrites (acetonitrile, and the like), alcohols (methanol, ethanol, propanol, 2-butanol, and the like), dimethylsulfoxide, pyridine, 2,6-luthidine, and the like, and a mixed solvent comprising two or more of these solvents, if necessary. Above all, xylene, tetrahydrofuran, N,N-dimethylformamide, N,N-dimethylacetamide, 1,3-dimethyl-2-imidazolidinone, methanol, pyridine, and the like are preferred, and N,N-dimethylacetamide and 1,3-dimethyl-2-imidazolidinone are especially preferred.

The present reaction can be carried out in a wide range of temperature from a temperature of under cooling to under heating, preferably at a temperature of under ice-cooling to the boiling point of the reaction mixture.

(6) The reaction between the compound [9] and the compound [12] to give the compound [4] can be carried out in the presence of a base in an appropriate solvent, if necessary. The leaving group in the compound [12] can be preferably, for example, a halogen atom.

Examples of the base usable in the present reaction include the inorganic and organic bases. The inorganic bases include alkali metal carbonates (potassium carbonate, sodium carbonate, and the like), alkali metal hydrogen carbonates (sodium hydrogen carbonate, potassium hydrogen carbonate, and the like), alkali metal hydroxides (sodium hydroxide, potassium hydroxide, lithium hydroxide, and the like), alkali metal hydrides (sodium hydride, and the like). A mixture of cesium carbonate and sodium iodide can also be used. The organic bases include alkali metal alkoxides (sodium methoxide, potassium t-butoxide, and the like), tri-lower alkylamines (triethylamine, tributylamine, diisopropylethylamine, and the like), tert-amines (1,4-diazabicyclo[2.2.2]octane, 1,5-diazabicyclo[4.3.0]non-5-ene, 1,8-diazabicyclo[5.4.0]-undec-7-ene, and the like), amines (N,N-dimethylaniline, N,N-diethylaniline, 4-dimethylaminopyridine, and the like), pyridine, lutidine and collidine, and the like. Above all, alkali metal carbonates, diisopropylethylamine, pyridine, and the like are preferred. In the present reaction, the bases above can also be used as a solvent.

Examples of the solvent usable in the present reaction include any inert solvent which does not disturb the reaction, such as ketones (e.g., acetone, methylethyl ketone, and the like), aromatic hydrocarbons (benzene, toluene, xylene, and the like), ethers (diethyl ether, diisopropyl ether, tetrahydrofuran, dioxane, 1,2-dimethoxyethane, and the like), amides (N,N-dimethylformamide, N,N-dimethylacetamide, 1,3-dimethyl-2-imidazolidinone, and the like), nitriles (acetonitrile, and the like), alcohols (methanol, ethanol, propanol, 2-butanol, and the like), dimethylsulfoxide, pyridine, 2,6-luthidine, and the like. A mixed solvent comprising two or more of these solvents can also be used. Above all, ketones and amides are preferred.

The present reaction can generally be carried out at a temperature of under ice-cooling to the reflux temperature of the solvent.

The reaction time for the present reaction is generally between 30 minutes and 24 hours; however, longer or shorter reaction time can be selected appropriately, if necessary. Further, an alkali metal iodide such as lithium iodide, sodium iodide, potassium iodide, and the like can also be added, which may facilitate the reaction.

The reaction between the compound [13] and the compound [14] can be carried out in the presence of a base in an appropriate solvent, if necessary. The leaving group in the compound [13] can be preferably, for example, a halogen atom or a nitro group.

Examples of the base usable in the present reaction include alkali metal carbonates (potassium carbonate, sodium carbonate, cesium carbonate, and the like), alkali metal hydrides (sodium hydride, and the like) and alkali metal alkoxides (sodium methoxide, potassium t-butoxide, and the like). Above all, sodium hydride is preferred.

Examples of the solvent usable in the present reaction include amides (N,N-dimethylformamide, N,N-dimethylacetamide, 1,3-dimethyl-2-imidazolidinone, and the like) and ethers (diethyl ether, diisopropyl ether, tetrahydrofuran, dioxane, 1,2-dimethoxyethane, and the like), and N,N-dimethylformamide, N,N-dimethylacetamide, 1,3-dimethyl-2-imidazolidinone, and the like are preferred.

The reaction for formylation of the compound [11] to give the compound [10] can be carried out in a conventional manner, if necessary. For example, the reaction can be carried out by reacting a formylating agent in accordance with the method for Duff reaction, Gatterman-Koch reaction, Vilsmeier reaction, and the like in an appropriate solvent.

The formylating agent usable in the Duff reaction includes any conventional ones without limitation, and hexamethylenetetramine, and the like are preferred.

Examples of the solvent include any inert solvent which does not disturb the reaction, such as organic acids (acetic acid, propionic acid, trifluoroacetic acid, methanesulfonic acid, and the like), halogenated hydrocarbons (chloroform, dichloromethane, dichloroethane, and the like), aromatic hydrocarbons (benzene, toluene, xylene, and the like), ethers (diethyl ether, diisopropyl ether, tetrahydrofuran, dioxane, 1,2-dimethoxyethane, and the like), nitrites (acetonitrile, and the like), water, and a mixed solvent comprising two or more of these solvents, if necessary. It is preferred to select any appropriate solvent depending on the method used.

The present reaction can be carried out in a wide range of temperature from a temperature of under cooling to under heating, preferably at −78° C. to the boiling point of the reaction mixture.

The resulting compounds of the present invention thus produced can be isolated and purified by a procedure well known in the field of organic chemistry such as recrystallization, column chromatography, and the like.

The present compound [1] or a pharmaceutically acceptable salt thereof has an excellent inhibitory effect on FXa, and hence is useful in the prevention and treatment of various disorders caused by thrombi and emboli in a mammal (e.g., human, monkey, rabbit, dog, cat, pig, horse, bull, mouse, rat, guinea pig, and the like), which disorders include, for example, stable angina pectoris, unstable angina pectoris, cerebral thrombosis, cerebral infarction, cerebral embolism, transient ischemic attack (TIA), ischemic cerebrovascular disease such as cerebrovascular spasm after subarachnoid hemorrhage, ischemic heart disease caused by coronary artery thrombogenesis, congestive chronic heart failure, myocardial infarction, acute myocardial infarction, pulmonary infarction, pulmonary embolism, pulmonary vascular disorders, economy-class syndrome, kidney disease (diabetic renal disease, chronic glomerulonephritis, IgA nephropathy, and the like), thrombogenesis with atherosclerosis, peripheral arterial occlusion, peripheral venous occlusion, Buerger's disease, deep vein thrombosis, disseminated intravascular coagulation (DIC), thrombogenesis after implantation of a synthetic vascular prosthesis or replacement of artificial heart valve or joint, intermittent claudication, thrombogenesis and reocclusion after blood circulation reconstruction such as percutaneous transluminal coronary angioplasty (PTCA) or percutaneous transluminal coronary artery recanalization (PTCR), systemic inflammatory response syndrome (SIRS), multiple organ failure (MODS), thrombogenesis in extracorporeal circulation, blood coagulation in case of blood drawing, diabetic circulatory disturbance, graft rejection, organ protection and improvement of function in case of transplantation, and the like The present compound is characterized in that it shows excellent inhibitory effect on FXa, decreased toxicity, and causes few side effects (bleeding, and the like) that are seen in the existing anticoagulants.

When an FXa inhibitor has a small distribution volume (internal medicine/blood concentration), it would be substantially free of side effects such as phospholipidosis, hepatotoxicity, and the like. Accordingly, FXa inhibitors, especially those having the distribution volume of 0.1-3.0 L/kg and the FXa inhibitory effect with the $IC_{50}$ value of 100 nM or below are substantially free of side effects such as phospholipidosis, hepatotoxicity, and the like, and useful as a medicament for treating thrombosis.

The present compound [1] or a pharmaceutically acceptable salt thereof can be formulated into a pharmaceutical composition comprising a therapeutically effective amount of the compound [1] and a pharmaceutically acceptable carrier therefor. The pharmaceutically acceptable carriers include diluents, binders (e.g., syrup, gum arabic, gelatine, sorbit, tragacanth, polyvinyl-pyrrolidone), excipients(e.g., lactose, sucrose, corn starch, potassium phosphate, sorbit, glycine), lubricants (e.g., magnesium stearate, talc, polyethylene glycol, silica), disintegrants (e.g., potato starch) and wetting agents (e.g., sodium lauryl sulfate), and the like The compound [1] of the present invention or a pharmaceutically acceptable salt thereof can be administered orally or parenterally, and be used as an appropriate pharmaceutical preparation. Examples of an appropriate preparation for oral administration include solid preparations (tablets, granules, capsules, powders, and the like), solutions, suspensions and emulsions. Examples of an appropriate preparation for parenteral administration include suppository, injections or preparation for continuous infusion prepared using distilled water for injection, physiological saline or aqueous glucose solution, and the like, or inhalant.

The dose of the compound [1] or a pharmaceutically acceptable salt thereof of the present invention may vary depending on the administration routes, and the age, weight and condition of the patient, or the kind or severity of the disease, it is usually in the range of about 0.1 to 50 mg/kg/day, preferably about 0.1 to 30 mg/kg/day.

EXAMPLES

The present invention will be illustrated in detail by Examples and Reference Examples, but should not be construed to be limited thereto.

Example 1

Methyl 2-{[(5-chloropyridin-2-yl)amino]-carbonyl}-3-[({trans-4-[(dimethylamino)carbonyl]-cyclohexyl}carbonyl)amino]benzofuran-5-carboxylate

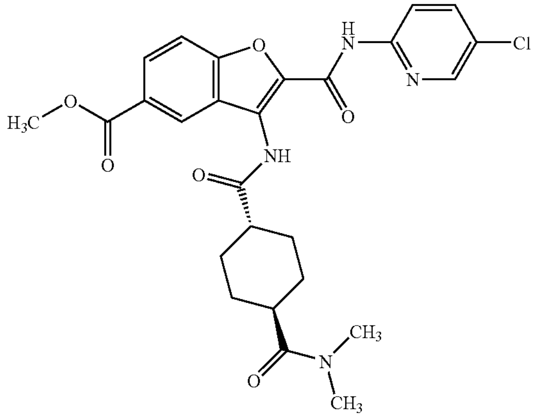

trans-4-[(Dimethylamino)carbonyl]cyclohexanecarboxylic acid (910 mg) obtained in Reference Example 1 is dissolved in thionyl chloride (10 ml), and the mixture is stirred at room temperature for 17 hours. The reaction solution is concentrated under reduced pressure, and the residue is dissolved in chloroform (6 ml). The mixture is added dropwise into a suspension of 3-amino-5-methoxycarbonyl-N-(5-chloropyridin-2-yl)benzofuran-2-carboxamide (1.21 g) obtained in Reference Example 78 in pyridine (10 ml) under ice-cooling. After the addition, the reaction solution is warmed to room temperature, and then stirred for 19 hours. To the reaction solution is poured a saturated aqueous sodium hydrogen carbonate solution, and the mixture is extracted with chloroform. The organic layer is washed with brine, dried over sodium sulfate, and evaporated to remove the solvent under reduced pressure. The resulting residue is suspended in diethyl ether and filtered to give the title compound (1.40 g).

APCI-MS M/Z: 527/529$[M+H]^+$

Example 2

Methyl [2-{[(5-chloropyridin-2-yl)amino]-carbonyl}-3-({[trans-4-(pyrrolidin-1-ylcarbonyl)-cyclohexyl]carbonyl}amino)benzofuran-5-yl]acetate

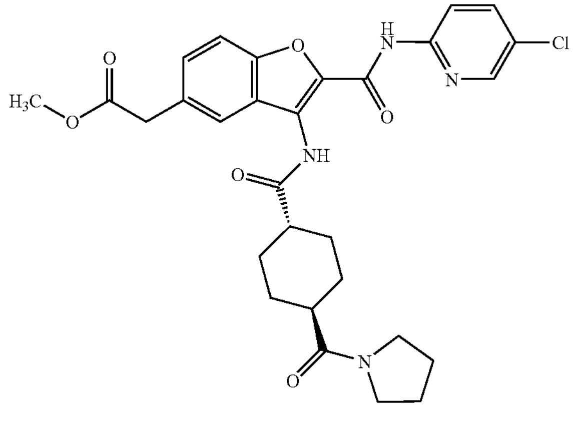

trans-4-(Pyrrolidin-1-ylcarbonyl)cyclohexanecarboxylic acid (1.03 g) obtained in Reference Example 2 is dissolved in thionyl chloride (10 ml), and the mixture is stirred at room temperature for 17 hours. The reaction solution is concentrated under reduced pressure, and the residue is dissolved in chloroform (6 ml). The solution is added dropwise to a suspension of 3-amino-5-methoxycarbonyl-methyl-N-(5-chloropyridin-2-yl)benzofuran-2-carboxamide (1.26 g) obtained in Reference Example 79 in pyridine (10 ml) under ice-cooling. After the addition, the reaction solution is warmed to room temperature and stirred for 19 hours. To the reaction solution is poured a saturated aqueous sodium hydrogen carbonate solution, and the mixture is extracted with chloroform. The organic layer is washed with saturated brine, dried over sodium sulfate, and evaporated to remove the solvent under reduced pressure. The resulting residue is suspended in diethyl ether and filtered to give the title compound (1.78 g).

APCI-MS M/Z:567/569[M+H]$^+$

Example 3

$N^2$-(5-Chloropyridin-2-yl)-$N^5$,$N^5$-dimethyl-3-({[trans-4-(morpholin-4-ylcarbonyl)cyclohexyll]carbonyl}-amino)benzofuran-2,5-dicarboxamide

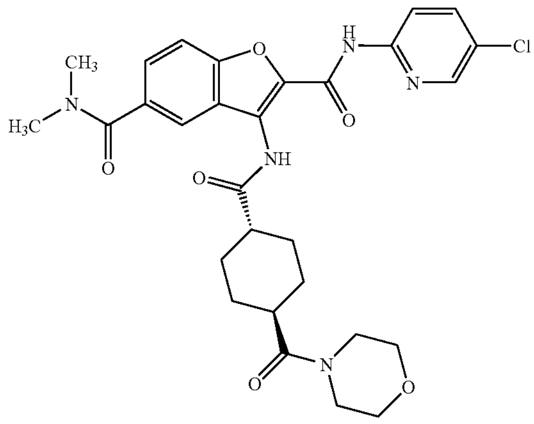

trans-4-(Morpholin-4-ylcarbonyl)cyclohexanecarboxylic acid (109 mg) obtained in Reference Example 3 is dissolved in thionyl chloride (5 ml) and the mixture is stirred at room temperature for 19 hours. The reaction solution is concentrated under reduced pressure, and the residue is dissolved in chloroform (4 m 1). To the solution is added 3-amino-5-dimethylaminocalbonyl-N-(5-chloropyridin-2-yl)-benzofuran-2-carboxamide (104 mg) obtained in Reference Example 128 under ice-cooling. After adding pyridine (4 ml), the reaction solution is warmed to room temperature, and stirred for 20 hours. To the reaction solution is poured a saturated aqueous sodium hydrogen carbonate solution, and the mixture is extracted with chloroform. The organic layer is washed with saturated brine, dried over sodium sulfate, and evaporated to remove the solvent under reduced pressure. The resulting residue is purified by NH-silica gel column chromatography (eluent: ethyl acetate) to give the title compound (81 mg).

APCI-MS M/Z:582/584[M+H]$^+$

Example 4

N-(5-Chloropyridin-2-yl)-3-[(5-morpholin-4-yl-5-oxopentanoyl)amino]benzofuran-2-carboxamide

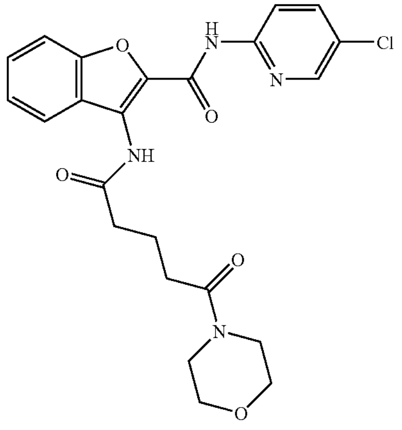

5-Morpholin-4-yl-5-oxopentanoic acid (120 mg) obtained in Reference Example 6 is dissolved in chloroform (3 ml), and thereto are added pyridine (97 μl) and thionyl chloride (39 μl) under ice-cooling. The mixture is then stirred at room temperature for 0.5 hours. The resulting reaction solution is cooled with ice, and thereto are added 3-amino-N-(5-chloropyridin-2-yl)benzofuran-2-carboxamide (86 mg) obtained in Reference Example 80 and pyridine (2 ml). The reaction solution is then warmed to room temperature and stirred for 1 hour. To the reaction solution is poured a saturated aqueous sodium hydrogen carbonate solution, and the mixture is extracted with chloroform. The organic layer is washed with saturated brine, dried over sodium sulfate, and evaporated to remove the solvent under reduced pressure. The resulting residue is purified by NH-silica gel column chromatography (eluent: chloroform) to give the title compound (125 mg). APCI-MS M/Z:471/473[M+H]$^+$ Example 5

2-{[(5-Chloropyridin-2-yl)amino]carbonyl}-3-[({trans-4-[(dimethylamino)carbonyl]cyclohexyl}carbonyl)-amino]benzofuran-5-carboxylic acid

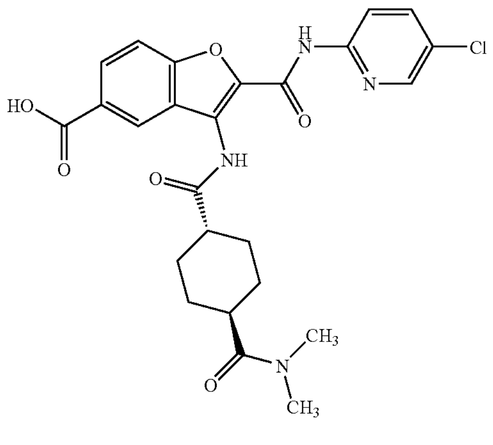

Methyl 2-{[(5-chloropyridin-2-yl)amino]carbonyl}-3-[({trans-4-[(dimethylamino)carbonyl]cyclohexyl}carbonyl)-amino]benzofuran-5-carboxylate (1.35 g) obtained in Example 1 is suspended in tetrahydrofuran-methanol (4:1) (20 ml). After adding a solution of sodium hydroxide (205 mg) in water (5 ml), the mixture is warmed to room temperature and stirred for 18 hours. The reaction solution is concentrated under reduced pressure, thereto poured ice-water, and the mixture is acidified by addition of 10% hydrochloric acid. The precipitates are collected by filtration, washed with water, and dried to give the title compound (1.23 g).

ESI-MS M/Z:511/513[M−H]$^-$

Example 6

$N^2$-(5-Chloropyridin-2-yl)-3-[({trans-4-[(dimethylamino)carbonyl]cyclohexyl}carbonyl)amino]-$N^5$,$N^5$-dimethylbenzofuran-2,5-dicarboxamide

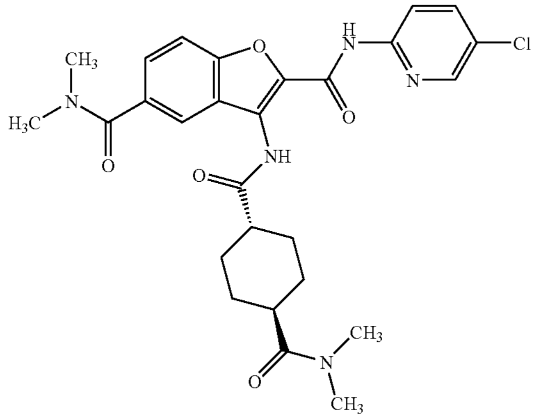

2-{[(5-Chloropyridin-2-yl)amino]carbonyl}-3-[({trans-4-[(dimethylamino)carbonyl]cyclohexyl}carbonyl)amino]-benzofuran-5-carboxylic acid (200 mg) obtained in Example 5 is suspended in chloroform-pyridine (1:3) (8 ml), and thereto are added successively dimethylamine hydrochloride (64 mg), 1-hydroxybenzotriazol (79 mg) and 1-ethyl-3-(3-dimethylaminopropyl)carbodiimide hydrochloride (112 mg) under ice-cooling. The mixture is then stirred at room temperature for 17 hours. To the reaction solution is poured a saturated aqueous sodium hydrogen carbonate solution, and the mixture is extracted with chloroform. The organic layer is washed with saturated brine and dried over sodium sulfate. After evaporating the solvent under reduced pressure, the resulting residue is suspended in ethanol-diethyl ether. The precipitates are collected by filtration and dried to give the title compound (176 mg).

APCI-MS M/Z:540/542[M+H]$^+$

Example 7 trans-N'-[2-{[(5-Chloropyridin-2-yl)amino]-carbonyl}-5-(morpholin-4-ylcarbonyl)benzofuran-3-yl]-N,N-dimethylcyclohexane-1,4-dicarboxamide

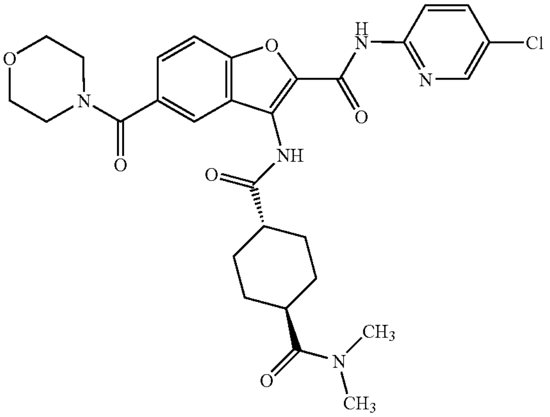

2-{[(5-Chloropyridin-2-yl)amino]carbonyl}-3-[({trans-4-[(dimethylamino)carbonyl]cyclohexyl}carbonyl)amino]-benzofuran-5-carboxylic acid (200 mg) obtained in Example 5 is suspended in chloroform-pyridine (1:3) (8 ml) and thereto are added successively morpholine (68 mg), 1-hydroxybenzotriazole (79 mg) and 1-ethyl-3-(3-dimethylaminopropyl)carbodiimide hydrochloride (112 mg) under ice-cooling. The mixture is then stirred at room temperature for 17 hours. To the reaction solution is poured a saturated aqueous sodium hydrogen carbonate solution, and the mixture is extracted with chloroform. The organic layer is washed with saturated brine and dried over sodium sulfate. After evaporating the solvent under reduced pressure, the resulting residue is suspended in ethanol-diethyl ether. The precipitates are collected by filtration and dried to give the title compound (174 mg)

APCI-MS M/Z:582/584[M+H]$^+$

Example 8 trans-N'-(2-{[(5-Chloropyridin-2-yl)amino]-carbonyl}benzofuran-3-yl)-N,N-dimethylcyclohexane-1,4-dicarboxamide

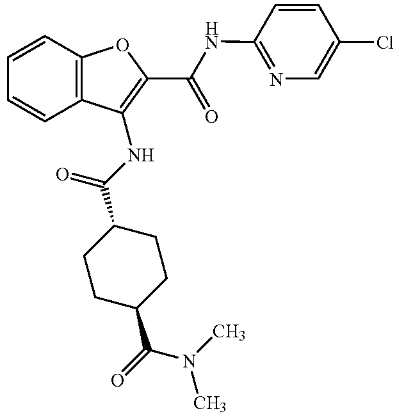

(1) To thionyl chloride (30 ml) is added trans-4-(methoxycarbonyl)cyclohexanecarboxylic acid (2.79 g) obtained in Reference Example 1(2) under ice-cooling, and the mixture is stirred at room temperature for 17 hours. The reaction solution is concentrated under reduced pressure and dissolved in chloroform (50 ml), and thereto are added successively 3-amino-N-(5-chloropyridin-2-yl)benzofuran-2-carboxamide (2.88 g) obtained in Reference Example 80 and pyridine (20 ml) under ice-cooling. The reaction solution is warmed to room temperature and stirred for 2 hours. To the reaction solution is poured a saturated aqueous sodium hydrogen carbonate solution, and the mixture is extracted with chloroform. The organic layer is washed successively with water and saturated brine, dried over sodium sulfate, and evaporated to remove the solvent under reduced pressure. The resulting residue is suspended in diethyl ether and filtered to give methyl trans-4-{[(2-{[(5-chloropyridin-2-yl)amino]carbonyl}-benzofuran-3-yl)amino] carbonyl}cyclohexanecarboxylate (3.32 g). APCI-MS M/Z: 456/458[M+H]$^+$ (2) Methyl trans-4-{[(2-{[(5-chloropyridin-2-yl)-amino] carbonyl}benzofuran-3-yl)amino]carbonyl}cyclohexane-carboxylate (300 mg) obtained in Example 8(1) is suspended in tetrahydrofuran-methanol (4:1) (10 ml) and thereto is added 10% aqueous sodium hydroxide solution (1 ml). The mixture is warmed to room temperature and stirred for 17 hours. The reaction solution is concentrated under reduced pressure, thereto added ice-water, and the mixture is acidified by addition of 10% hydrochloric acid. The precipitates are collected by filtration, washed with water, and dried to give trans-4-{[(2-{[(5-chloropyridin-2-yl)amino] carbonyl}benzofuran-3-yl)amino]carbonyl}-cyclohexanecarboxylic acid (270 mg).

ESI-MS M/Z:440/442[M−H]$^-$ (3) trans-4-{[(2-{[(5-Chloropyridin-2-yl)amino]-carbonyl}benzofuran-3-yl)amino]carbonyl}cyclohexane-carboxylic acid (176 mg) obtained in Example 8(2) is suspended in pyridine (8 ml), and thereto are added successively dimethylamine hydrochloride (65 mg), 1-hydroxybenzotriazole (108 mg) and 1-ethyl-3-(3-dimethylaminopropyl)carbodiimide hydrochloride (153 mg) under ice-cooling, followed by stirring at room temperature for 19 hours. To the reaction solution is poured ice-water and the precipitates are collected by filtration. The resulting precipitates are dissolved in chloroform and dried over sodium sulfate. After evaporating the solvent under reduced pressure, the residue is purified by NH-silica gel column chromatography (eluent: ethyl acetate) The resulting residue is suspended in n-hexane and the precipitates are collected by filtration to give the title compound (137 mg). APCI-MS M/Z:469/471[M+H]$^+$ Example 9

5-[(2-{[(5-chloropyridin-2-yl)amino]carbonyl}-benzofuran-3-yl)amino]-5-oxopentanoic acid

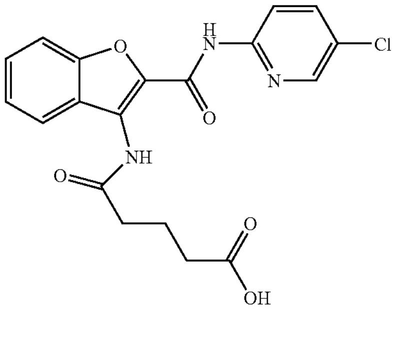

(1) Monomethyl glutarate (3.32 g) is dissolved in chloroform (50 ml) and thereto are added thionyl chloride (1.75 ml) and N,N-dimethylformamide (one drop). After stirring for 1.5 hours at the same temperature, the reaction solution is cooled, and thereto are added 3-amino-N-(5-chloropyridin-2-yl)benzofuran-2-carboxamide (5.00 g) obtained in Reference Example 80 and pyridine (7.0 ml). After stirring for 2.5 hours at room temperature, the reaction solution is poured into 5% hydrochloric acid and extracted with chloroform. The organic layer is washed successively with saturated brine, a saturated aqueous sodium hydrogen carbonate solution and saturated brine, dried over sodium sulfate, and evaporated to remove the solvent under reduced pressure. The resulting residue is suspended in diisopropyl ether and the precipitates are collected by filtration to give methyl 5-[(2-{[(5-chloropyridin-2-yl)amino]carbonyl}benzofuran-3-yl) amino]-5-oxopentanoate (6.16 g). APCI-MS M/Z:416/418 [M+H]$^+$ (2) Methyl 5-[(2-{[(5-chloropyridin-2-yl)amino]-carbonyl}benzofuran-3-yl)amino]-5-oxopentanoate (4.44 g) obtained in Example 9(1) is suspended in methanol (50 ml), and thereto is added 2N aqueous sodium hydroxide solution (30 ml) under ice-cooling followed by stirring at room temperature for 2 hours. After evaporating methanol under reduced pressure, the residue is diluted with water and washed with diethyl ether. The separated aqueous layer is acidified with 10% hydrochloric acid under ice-cooling, and the precipitates are collected by filtration. The resulting solid materials are washed successively with water, ethanol and diethyl ether, and dried to give the title compound (3.99 g). ESI-MS M/Z:400/402[M−H]$^-$ Example 10

6-[(2-{[(5-Chloropyridin-2-yl)amino]-carbonyl}benzofuran-3-yl)amino]-6-oxohexanoic acid

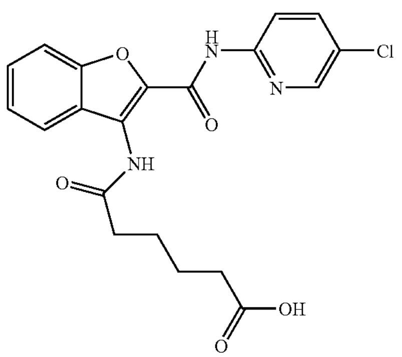

(1) Monomethyl adipate (2.55 g) is dissolved in chloroform (35 ml) and there to are added thionyl chloride (1.25 ml) and N,N-dimethylformamide (2 drops) at room temperature. The mixture is stirred at the same temperature for 3 hours and 20 minutes, and thereto are added 3-amino-N-(5-chloropyridin-2-yl)benzofuran-2-carboxamide (3.50 g) obtained in Reference Example 80 and pyridine (5.0 ml). After stirring for 14.5 hours at room temperature, a saturated aqueous sodium hydrogen carbonate solution is added to the reaction solution, and the mixture is extracted with chloroform. The organic layer is washed with saturated brine, dried over sodium sulfate, and evaporated to remove the solvent under reduced pressure. The resulting residue is suspended in diisopropyl ether and the precipitates are collected by filtration to give methyl 6-[(2-{[(5-chloropyridin-2-yl)amino] carbonyl}benzofuran-3-yl)amino]-6-oxohexanoate (4.72 g). APCI-MS M/Z:430/432[M+H]$^+$ (2) Methyl 6-[(2-{[(5-chloropyridin-2-yl)amino]-carbonyl}benzofuran-3-yl)amino]-6-oxohexanoate (4.30 g) obtained in Example 10(1) is suspended in methanol (5 m), and thereto is added at room temperature 2N aqueous sodium hydroxide solution (30 ml). The mixture is stirred at room temperature for 4 hours, and at 50° C. for 2 hours. The reaction solution is diluted with water and acidified by addition of 10% hydrochloric acid under ice-cooling, and the precipitates are collected by filtration and dried to give the title compound (3.54 g). ESI-MS M/Z:414/416[M−H]$^-$ Example 11

N-{[(2-{[(5-Chloropyridin-2-yl)amino]-carbonyl}benzofuran-3-yl)amino]carbonyl}-β-alanine

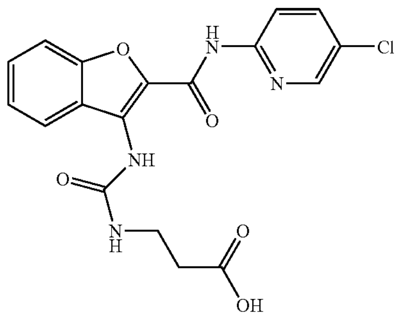

(1) β-Alanine t-butyl ester hydrochloride (3.00 g) is suspended in chloroform (30 ml) and thereto is added triphosgene (1.99 g) under ice-cooling, followed by dropwise addition of pyridine (7.0 ml) at the same temperature over 7 minutes. After stirring at the same temperature for 20 minutes, to the reaction solution are added 3-amino-N-(5-chloropyridin-2-yl)benzofuran-2-carboxamide (3.07 g) obtained in Reference Example 80 and pyridine (7.0 ml). The mixture is then heated under reflux for 3 hours and 40 minutes. The reaction solution is allowed to cool to room temperature, thereto is added 5% hydrochloric acid, and the mixture is extracted with chloroform. The organic layer is washed with saturated brine and a saturated aqueous sodium hydrogen carbonate solution, dried over sodium sulfate, and evaporated to remove the solvent under reduced pressure. The resulting residue is suspended in chloroform-diisopropyl ether and the precipitates are collected by filtration to give N-{[(2-{[(5-chloropyridin-2-yl)amino]carbonyl}benzofuran-3-yl) amino]carbonyl}-β-alanine t-butyl ester (2.96 g).

APCI-MS M/Z:459/461[M+H]$^+$ (2) N-{[(2-{[(5-Chloropyridin-2-yl)amino]carbonyl}-benzofuran-3-yl)amino]carbonyl}-β-alanine t-butyl ester (1.71 g) obtained in Example 11(1) is dissolved in trifluoroacetic acid (15 ml), and the mixture is stirred at room temperature for 1 hour and 45 minutes. The reaction solution is concentrated in vacuo to reduce the volume by about half. To the residue is added diisopropyl ether and the precipitates are collected by filtration to give the title compound (1.57 g). ESI-MS M/Z:401/403[M−H]$^-$ Examples 12-17

The amino compounds and carboxylic acids obtained in Reference Examples are treated in a similar manner to Example 1, 2, 3 or 4 to give the following compounds.

| EX. NO. | Structure | Physicochemical Properties |
|---|---|---|
| 12 | 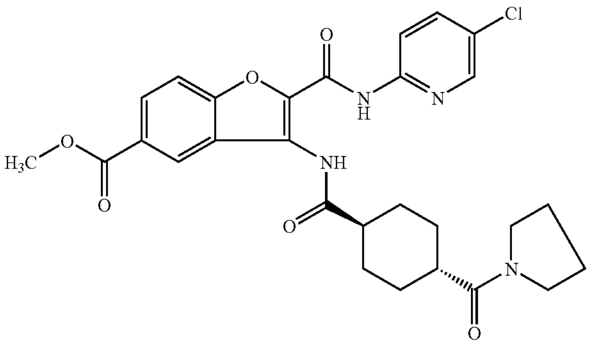 | APCI-MS M/Z:533/535 [M + H]$^+$ |

-continued
| EX. NO. | Structure | Physicochemical Properties |
| --- | --- | --- |
| 13 | 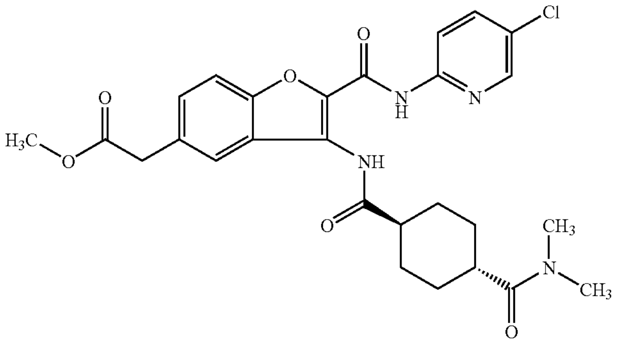 | APCI-MS M/Z:541/543 [M + H]$^+$ |
| 14 | 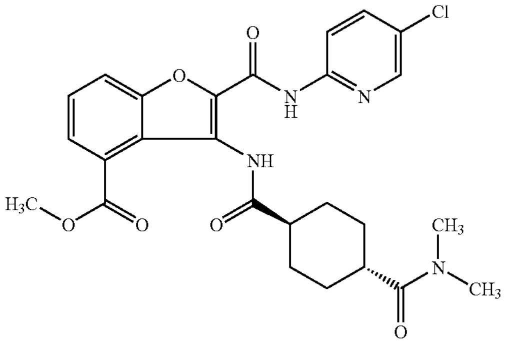 | APCI-MS M/Z:527/529 [M + H]$^+$ |
| 15 | 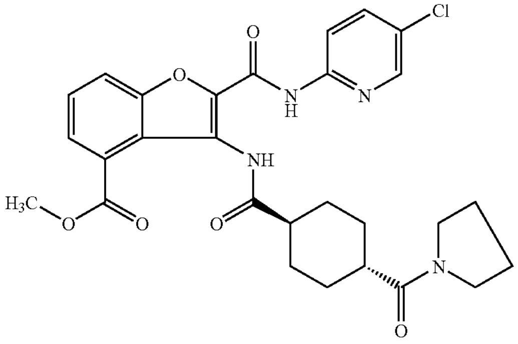 | APCI-MS M/Z:553/555 [M + H]$^+$ |
| 16 | 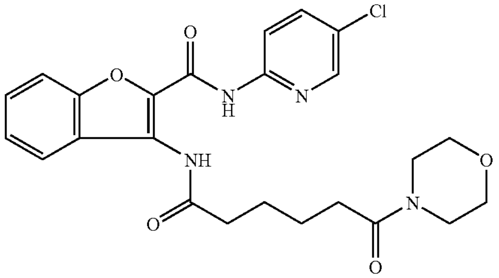 | APCI-MS M/Z:485/487 [M + H]$^+$ |

-continued
| EX. NO. | Structure | Physicochemical Properties |
|---|---|---|
| 17 | 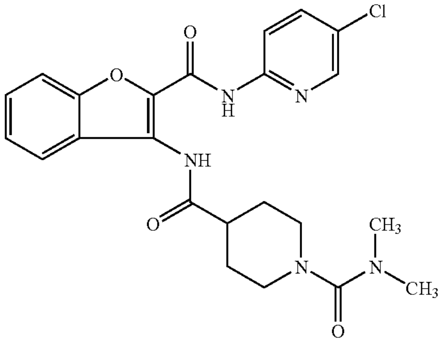 | APCI-MS M/Z:470/472 $[M + H]^+$ |
Examples 18-22
The corresponding carboxylic acid esters are treated in a similar manner to Example 5 to give the following compounds.
| EX. NO. | Structure | Physicochemical Properties |
|---|---|---|
| 18 | 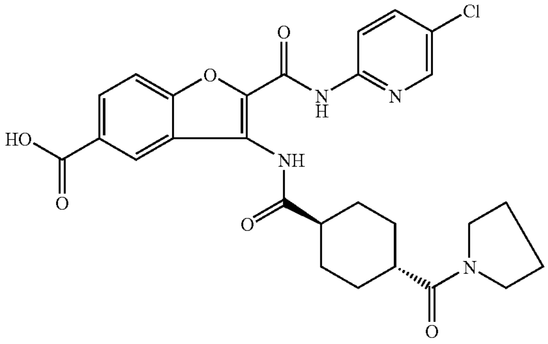 | ESI-MS M/Z:537/539 $[M - H]^-$ |
| 19 | 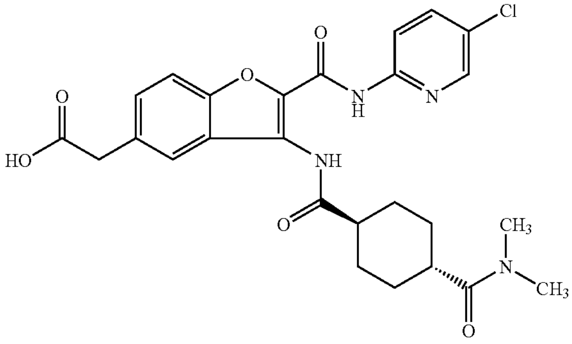 | ESI-MS M/Z:525/527 $[M - H]^-$ |

-continued
| EX. NO. | Structure | Physicochemical Properties |
|---|---|---|
| 20 | 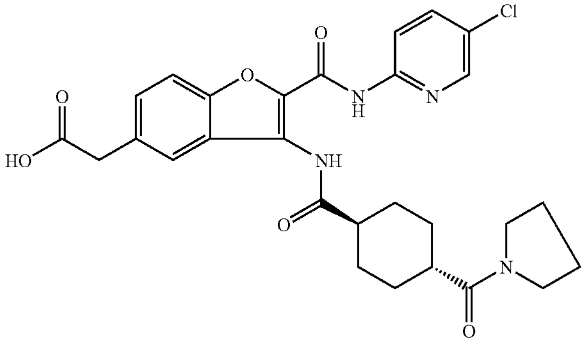 | ESI-MS M/Z:551/553 [M − H]⁻ |
| 21 | 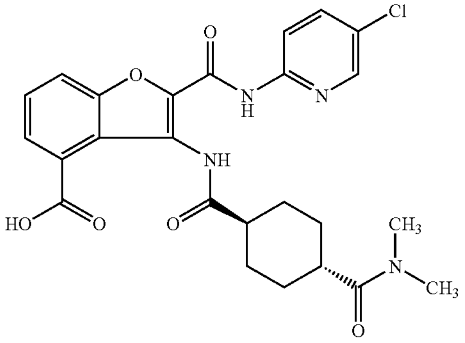 | ESI-MS M/Z:511/513 [M − H]⁻ |
| 22 | 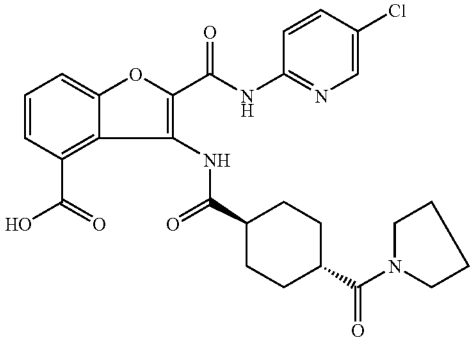 | ESI-MS M/Z:537/539 [M − H]⁻ |
Examples 23-42
The corresponding carboxylic acids and the corresponding amino compounds are treated in a similar manner to Example 6 to give the following compounds.

| EX. NO. | Structure | Physicochemical Properties |
|---|---|---|
| 23 | 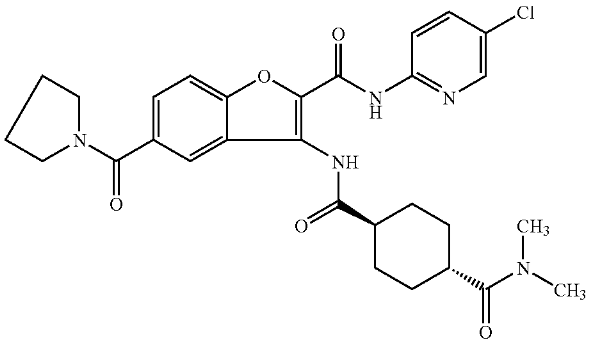 | APCI-MS M/Z:556/558 [M + H]$^+$ |
| 24 | 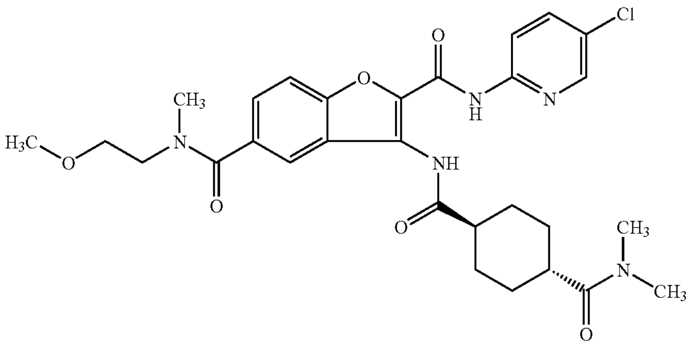 | APCI-MS M/Z:584/586 [M + H]$^+$ |
| 25 | 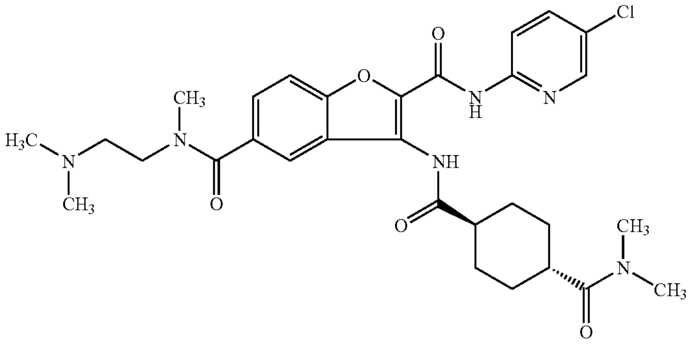 | APCI-MS M/Z:597/599 [M + H]$^+$ |
| 26 | 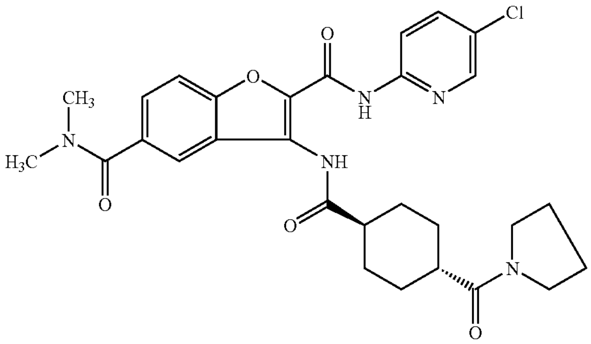 | APCI-MS M/Z:566/568 [M + H]$^+$ |

-continued
| EX. NO. | Structure | Physicochemical Properties |
| --- | --- | --- |
| 27 | 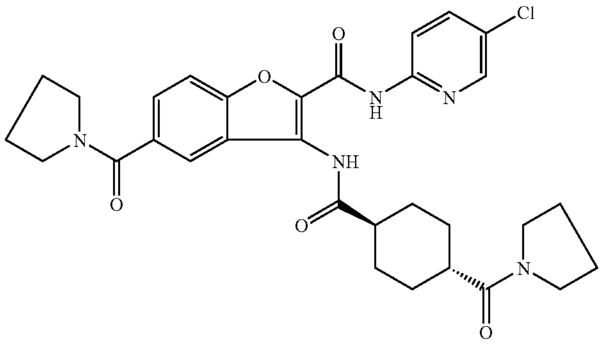 | APCI-MS M/Z:592/594 [M + H]+ |
| 28 | 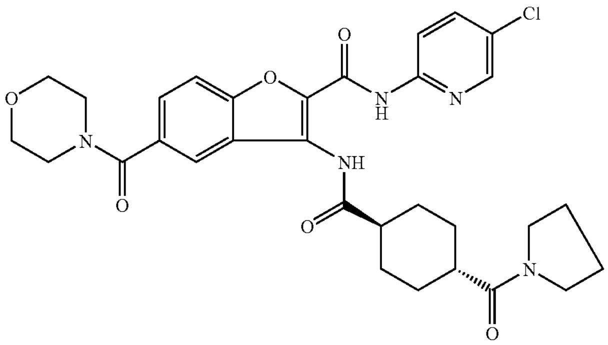 | APCI-MS M/Z:608/610 [M + H]+ |
| 29 | 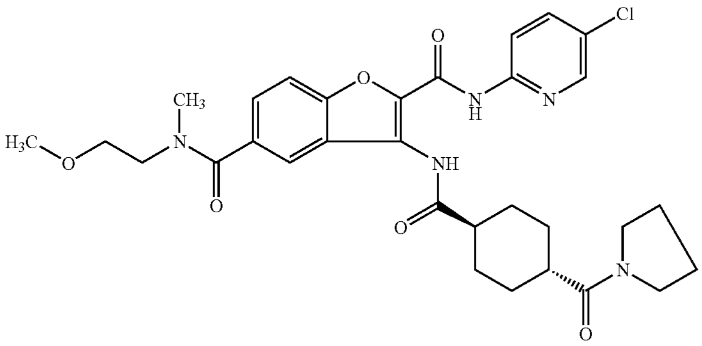 | APCI-MS M/Z:610/612 [M + H]+ |
| 30 | 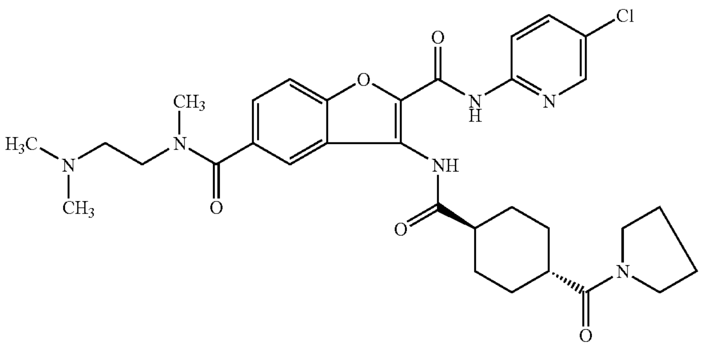 | APCI-MS M/Z:623/625 [M + H]+ |

-continued
| EX. NO. | Structure | Physicochemical Properties |
|---|---|---|
| 31 | 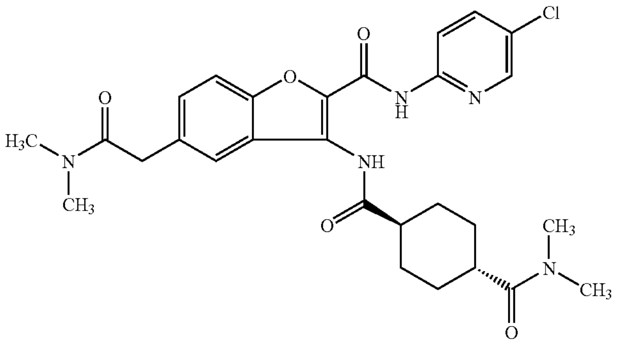 | APCI-MS M/Z:554/556 [M + H]$^+$ |
| 32 | 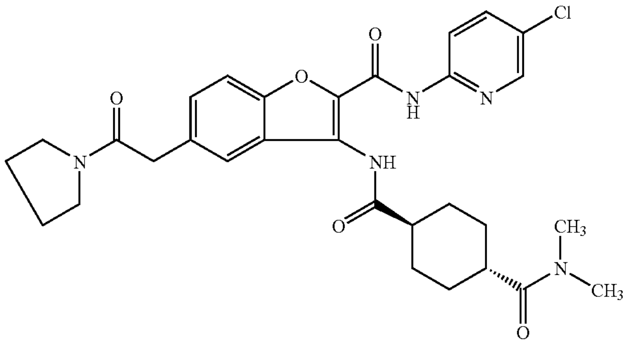 | APCI-MS M/Z:580/582 [M + H]$^+$ |
| 33 | 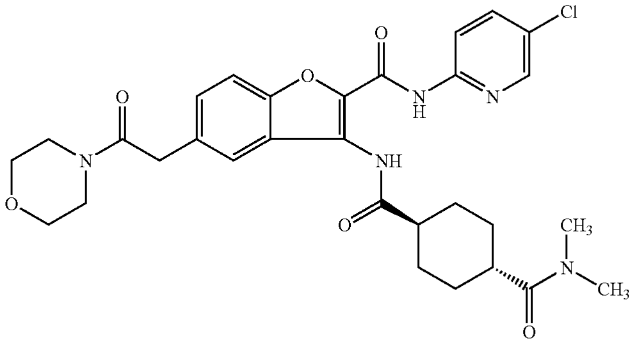 | APCI-MS M/Z:596/598 [M + H]$^+$ |
| 34 | 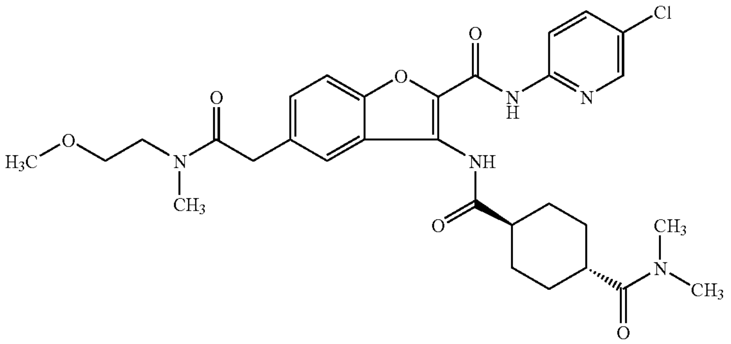 | APCI-MS M/Z:598/600 [M + H]$^+$ |

-continued
| EX. NO. | Structure | Physicochemical Properties |
|---|---|---|
| 35 | 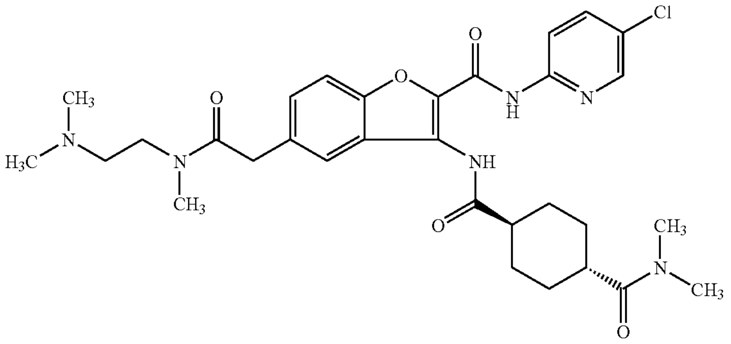 | APCI-MS M/Z:611/613 [M + H]$^+$ |
| 36 | 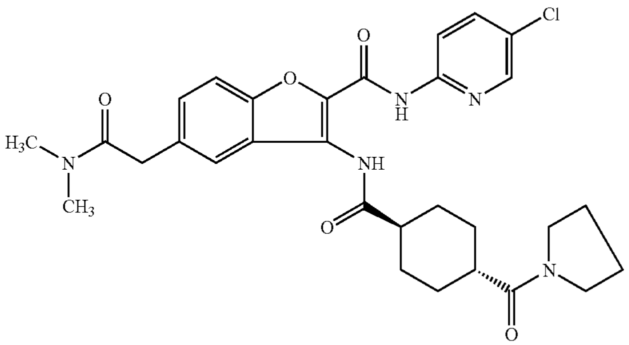 | APCI-MS M/Z:580/582 [M + H]$^+$ |
| 37 | 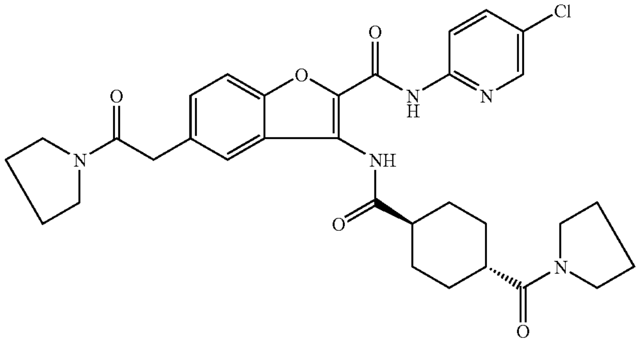 | APCI-MS M/Z:606/608 [M + H]$^+$ |
| 38 | 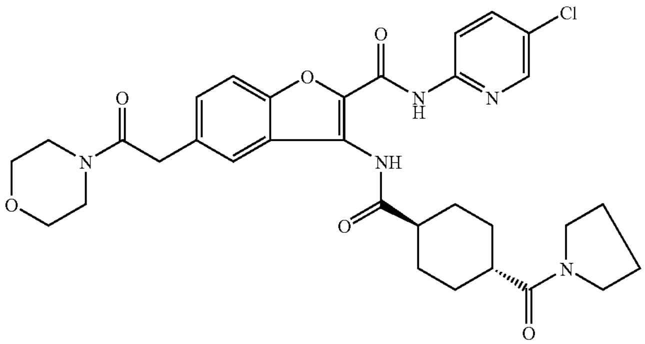 | APCI-MS M/Z:622/624 [M + H]$^+$ |

-continued
| EX. NO. | Structure | Physicochemical Properties |
|---|---|---|
| 39 | 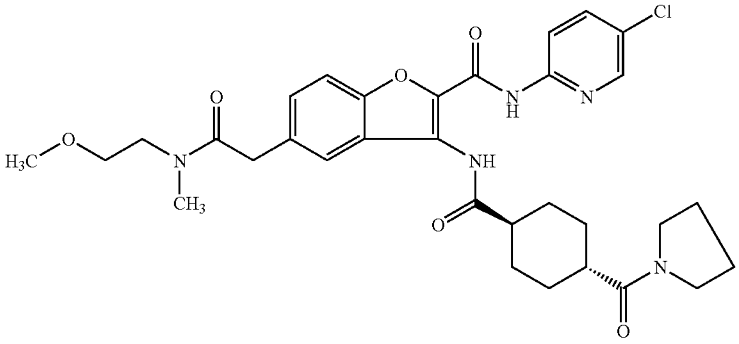 | APCI-MS M/Z:624/626 [M + H]+ |
| 40 | 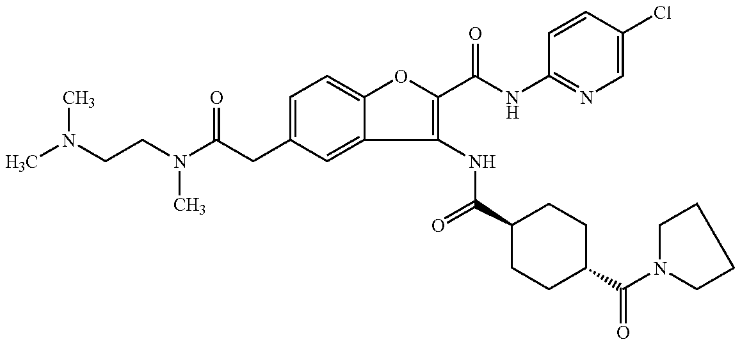 | APCI-MS M/Z:637/639 [M + H]+ |
| 41 | 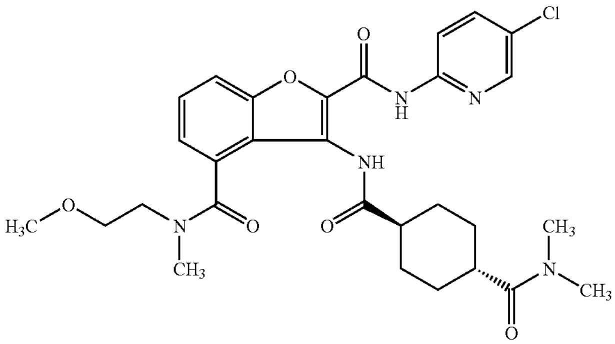 | APCI-MS M/Z:584/586 [M + H]+ |
| 42 | 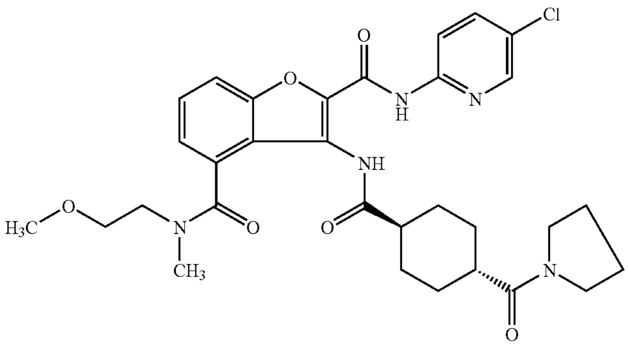 | APCI-MS M/Z:610/612 [M + H]+ |

Example 43

N-(5-Chloropyridin-2-yl)-5-(2-hydroxyethyl)-3-({[trans-4-(pyrrolidin-1-ylcarbonyl)cyclohexyl]carbonyl}-amino)benzofuran-2-carboxamide

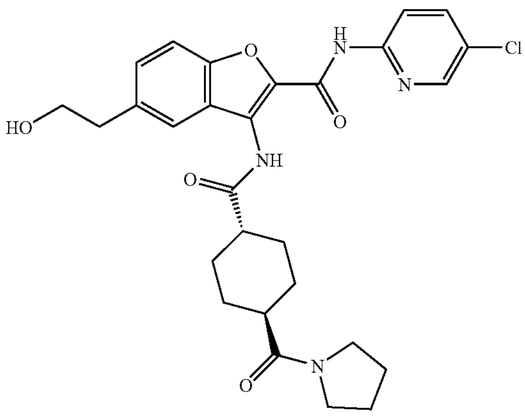

Methyl [2-{[(5-chloropyridin-2-yl)amino]carbonyl}-3-({[trans-4-(pyrrolidin-1-ylcarbonyl)cyclohexyl]carbonyl}-amino)benzofuran-5-yl]acetate (113 mg) obtained in Example 2 is suspended in tetrahydrofuran-ethanol (6:1) (7 ml). To the suspension is added lithium borohydride (13 mg), and the mixture is stirred at room temperature for 4 hours. After pouring 10% hydrochloric acid under ice-cooling, the reaction solution is stirred at room temperature for several minutes. The reaction solution is then basified by addition of a saturated aqueous sodium hydrogen carbonate solution, followed by extraction with chloroform. The organic layer is washed with saturated brine, dried over sodium sulfate, and evaporated to remove the solvent under reduced pressure. The resulting residue is purified by NH-silica gel column chromatography (eluent: chloroform), and the resulting residue is then suspended in diethyl ether. The precipitates are collected by filtration and dried to give the title compound (28 mg). APCI-MS M/Z:539/541[M+H]$^+$ Example 44

The corresponding carboxylic acid esters are treated in a similar manner to Example 43 to give the following compound.

| EX. NO. | Structure | Physicochemical Properties |
|---|---|---|
| 44 | 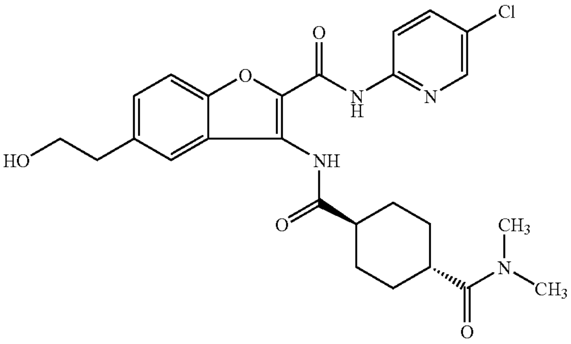 | APCI-MS M/Z:513/515 [M + H]$^+$ |

Examples 45-92

The carboxylic acids, which are obtained in Example 8(2) and Examples 9-11, and corresponding amino compounds are treated in a similar manner to Example 8(3) to give the following compounds.

| EX. NO. | Structure | Physicochemical Properties |
|---|---|---|
| 45 | 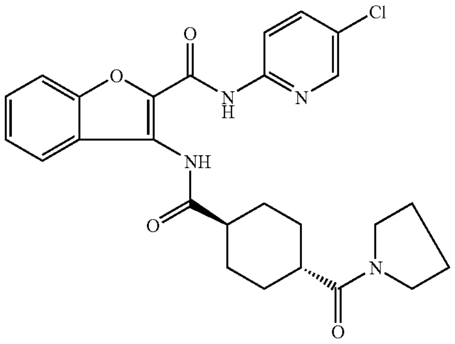 | APCI-MS M/Z:495/497 $[M + H]^+$ |
| 46 | 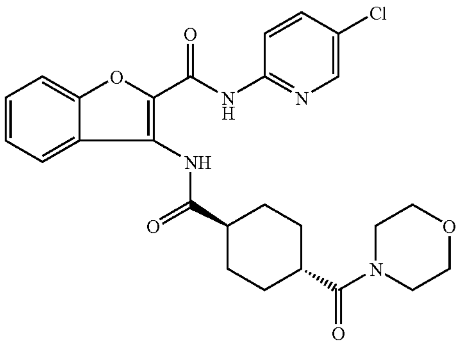 | APCI-MS M/Z:511/513 $[M + H]^+$ |
| 47 | 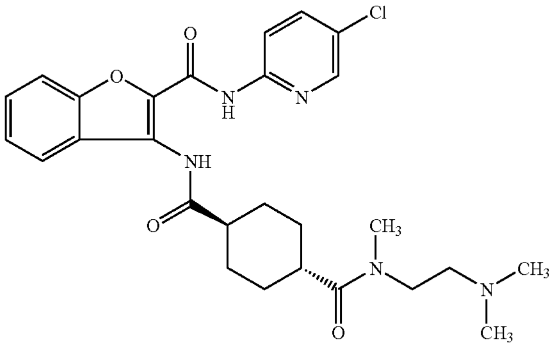 | APCI-MS M/Z:526/528 $[M + H]^+$ |
| 48 | 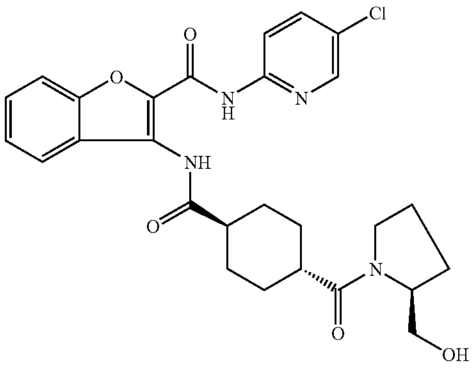 | APCI-MS M/Z:525/527 $[M + H]^+$ |

-continued
| EX. NO. | Structure | Physicochemical Properties |
|---|---|---|
| 49 | 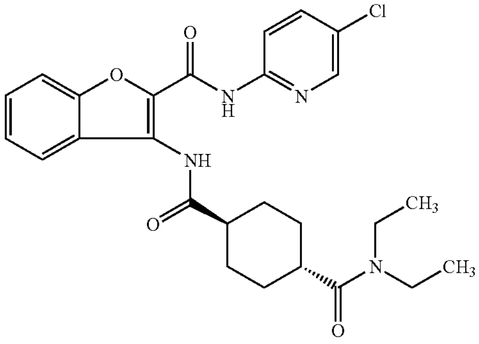 | APCI-MS M/Z:497/499 $[M + H]^+$ |
| 50 | 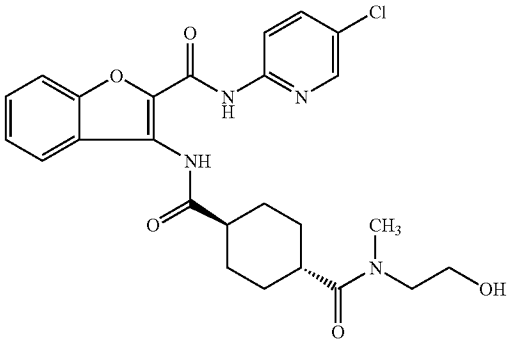 | APCI-MS M/Z:499/501 $[M + H]^+$ |
| 51 | 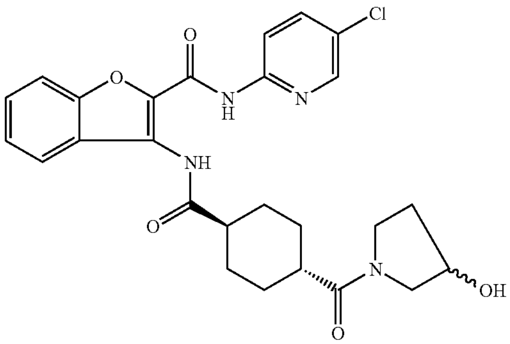 | APCI-MS M/Z:511/513 $[M + H]^+$ |
| 52 | 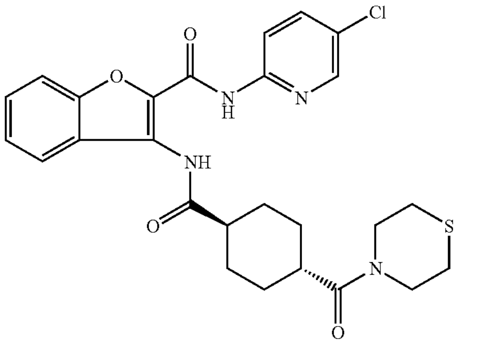 | APCI-MS M/Z:527/529 $[M + H]^+$ |

-continued
| EX. NO. | Structure | Physicochemical Properties |
|---|---|---|
| 53 | 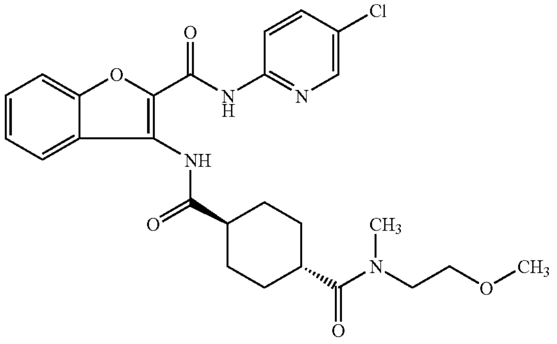 | APCI-MS M/Z:513/515 $[M + H]^+$ |
| 54 | 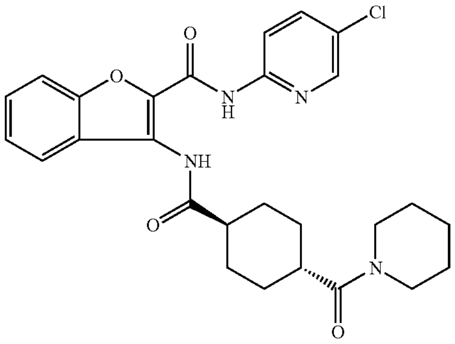 | APCI-MS M/Z:509/511 $[M + H]^+$ |
| 55 | 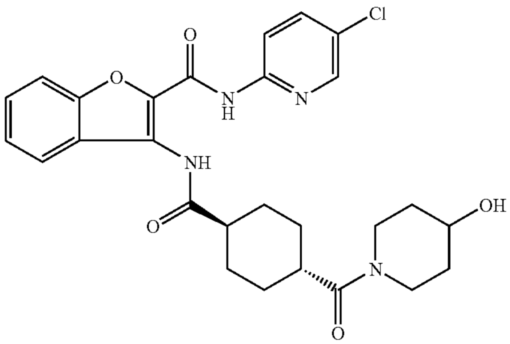 | APCI-MS M/Z:525/527 $[M + H]^+$ |
| 56 | 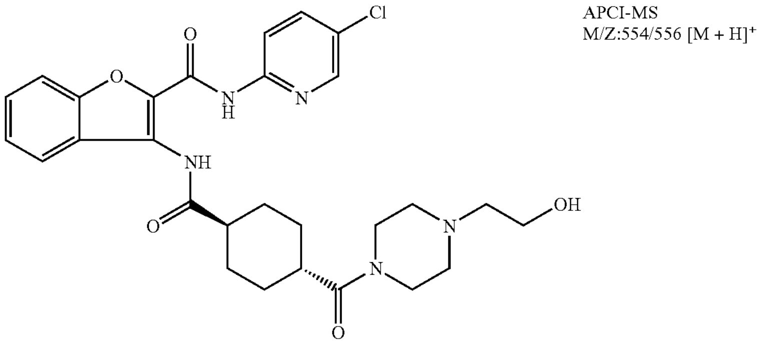 | APCI-MS M/Z:554/556 $[M + H]^+$ |

-continued
| EX. NO. | Structure | Physicochemical Properties |
|---|---|---|
| 57 | 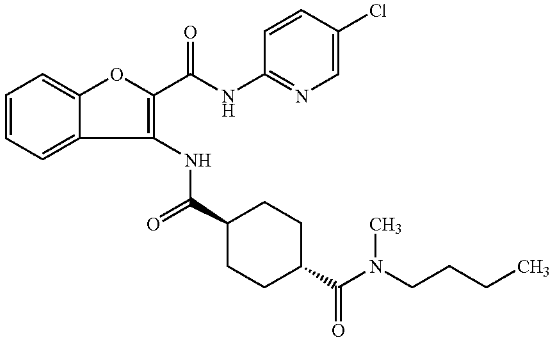 | APCI-MS M/Z:511/513 $[M + H]^+$ |
| 58 | 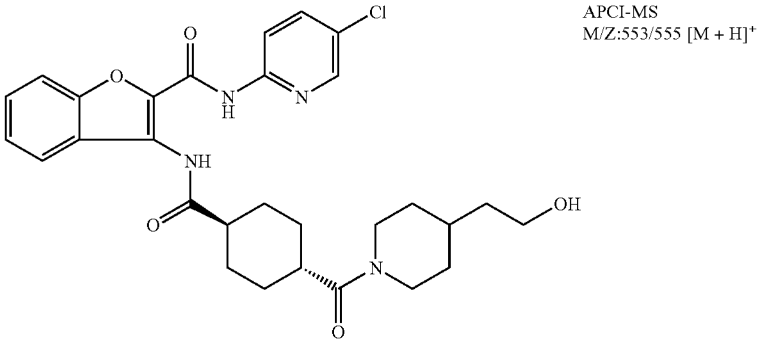 | APCI-MS M/Z:553/555 $[M + H]^+$ |
| 59 | 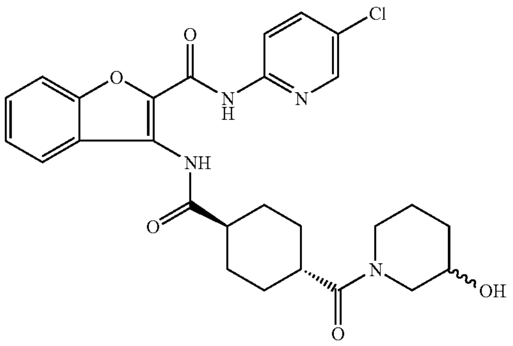 | APCI-MS M/Z:525/527 $[M + H]^+$ |
| 60 | 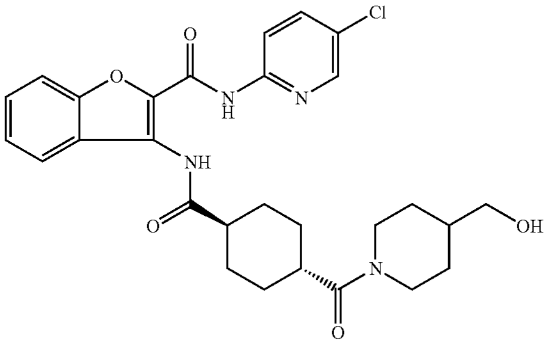 | APCI-MS M/Z:539/541 $[M + H]^+$ |

-continued
| EX. NO. | Structure | Physicochemical Properties |
|---|---|---|
| 61 | 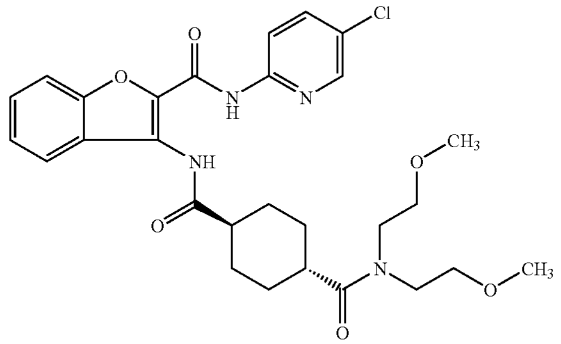 | APCI-MS M/Z:557/559 $[M+H]^+$ |
| 62 | 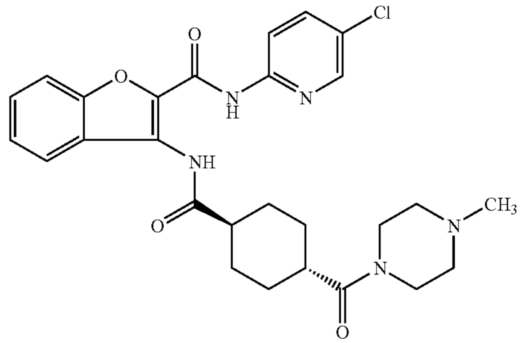 | APCI-MS M/Z:524/526 $[M+H]^+$ |
| 63 | 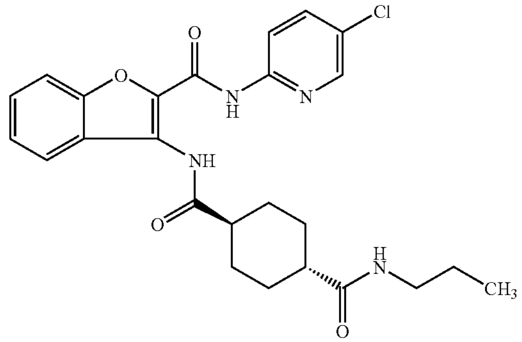 | APCI-MS M/Z:483/485 $[M+H]^+$ |
| 64 | 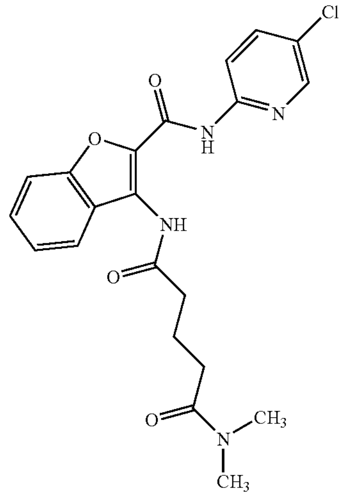 | APCI-MS M/Z:429/431 $[M+H]^+$ |

-continued
| EX. NO. | Structure | Physicochemical Properties |
|---|---|---|
| 65 | 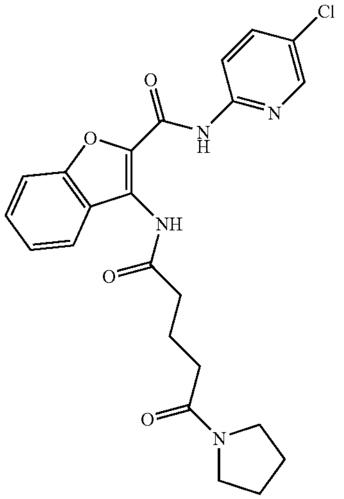 | APCI-MS M/Z:455/457 [M − H]$^+$ |
| 66 | 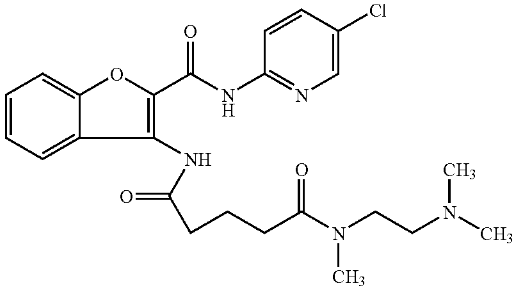 | APCI-MS M/Z:486/488 [M − H]$^+$ |
| 67 | 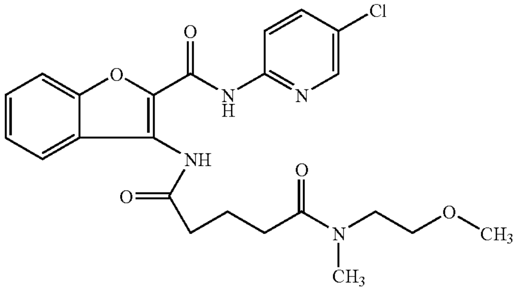 | APCI-MS M/Z:473/475 [M − H]$^+$ |

-continued
| EX. NO. | Structure | Physicochemical Properties |
| --- | --- | --- |
| 68 | 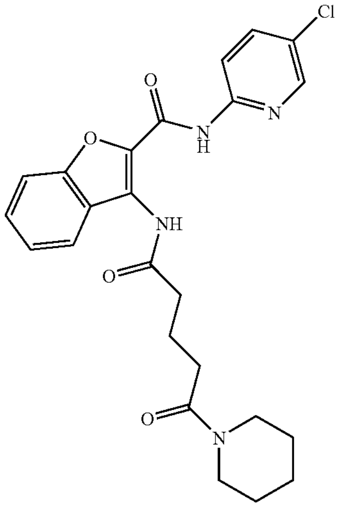 | APCI-MS M/Z:469/471 [M − H]$^+$ |
| 69 | 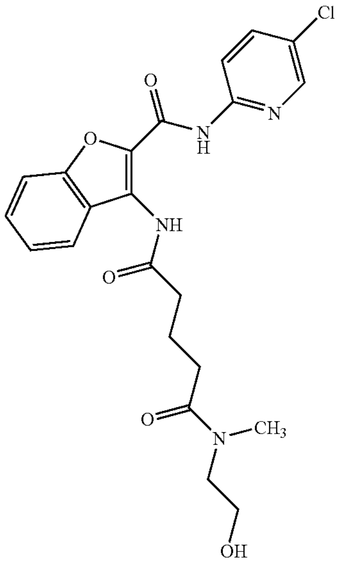 | APCI-MS M/Z:459/461 [M + H]$^+$ |

-continued
| EX. NO. | Structure | Physicochemical Properties |
|---|---|---|
| 70 | 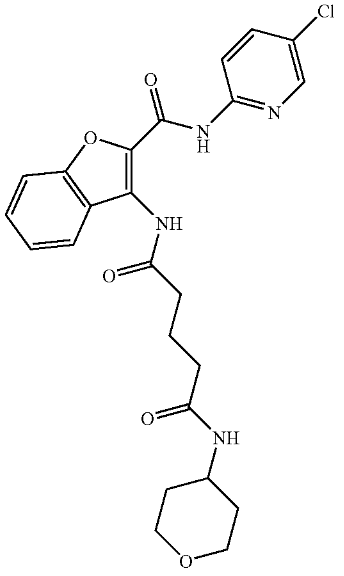 | APCI-MS M/Z:485/487 $[M + H]^+$ |
| 71 | 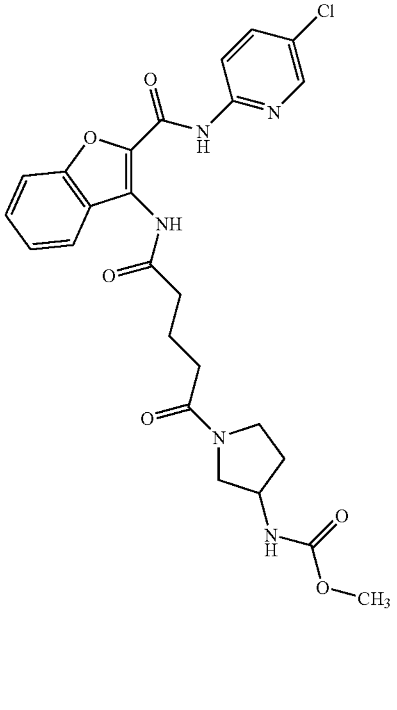 | APCI-MS M/Z:528/530 $[M + H]^+$ |

-continued
| EX. NO. | Structure | Physicochemical Properties |
|---|---|---|
| 72 | 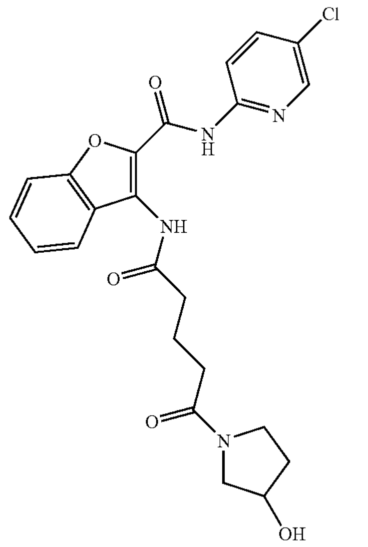 | APCI-MS M/Z:471/473 [M + H]$^+$ |
| 73 | 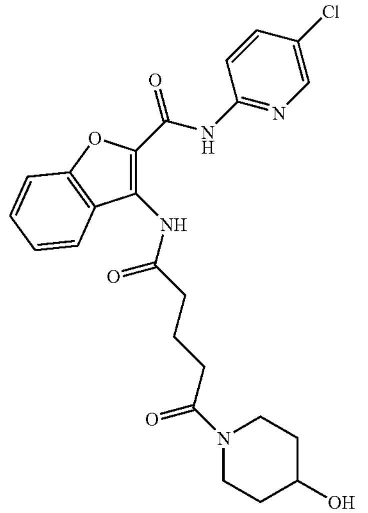 | APCI-MS M/Z:485/487 [M + H]$^+$ |
| 74 | 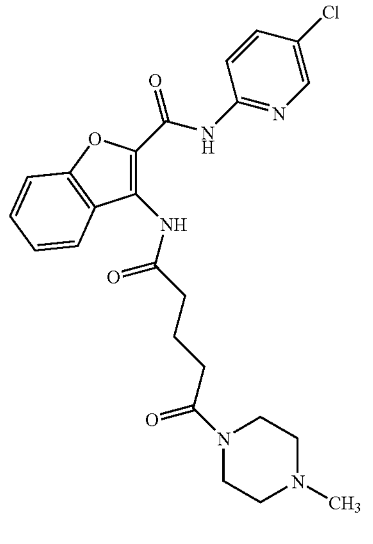 | APCI-MS M/Z:484/486 [M + H]$^+$ |

-continued
| EX. NO. | Structure | Physicochemical Properties |
|---|---|---|
| 75 | 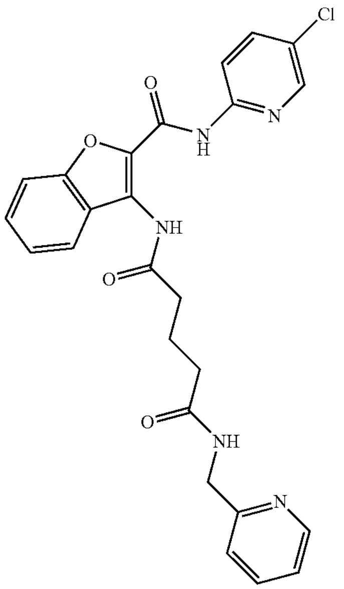 | APCI-MS M/Z:492/494 [M + H]$^+$ |
| 76 | 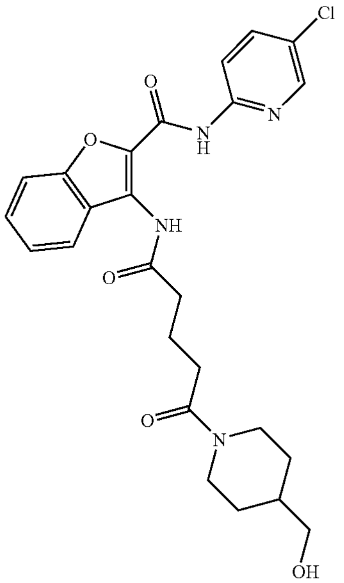 | APCI-MS M/Z:499/501 [M + H]$^+$ |
| 77 | 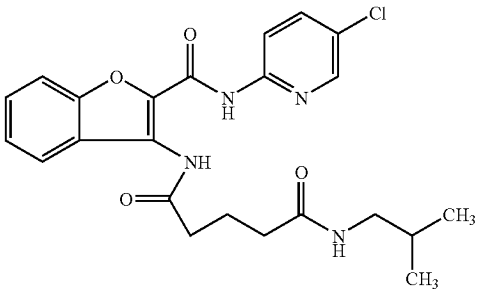 | APCI-MS M/Z:457/459 [M + H]$^+$ |

-continued
| EX. NO. | Structure | Physicochemical Properties |
|---|---|---|
| 78 | 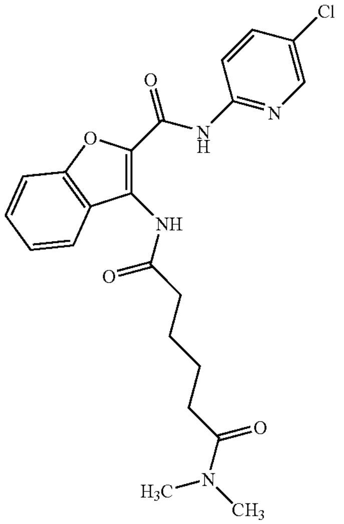 | APCI-MS M/Z:443/445 [M + H]$^+$ |
| 79 | 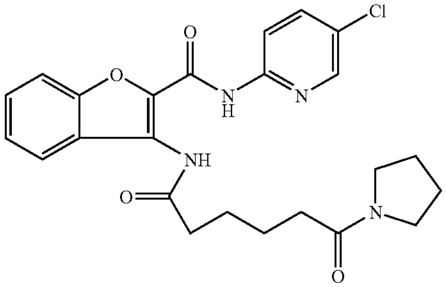 | APCI-MS M/Z:469/471 [M + H]$^+$ |
| 80 | 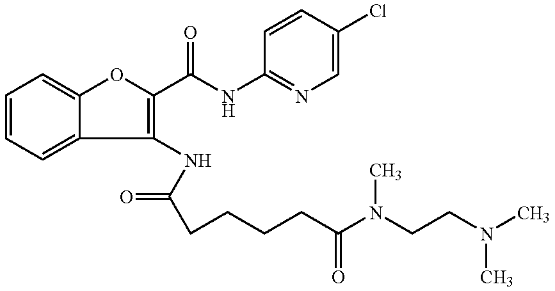 | APCI-MS M/Z:500/502 [M + H]$^+$ |
| 81 | 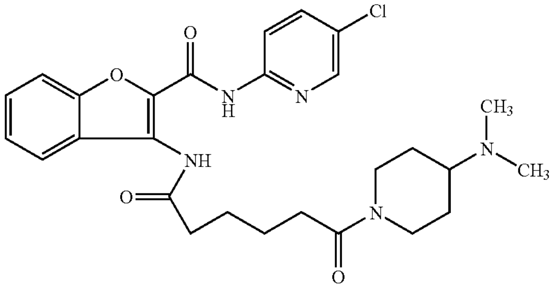 | APCI-MS M/Z:526/528 [M + H]$^+$ |

-continued
| EX. NO. | Structure | Physicochemical Properties |
|---|---|---|
| 82 | 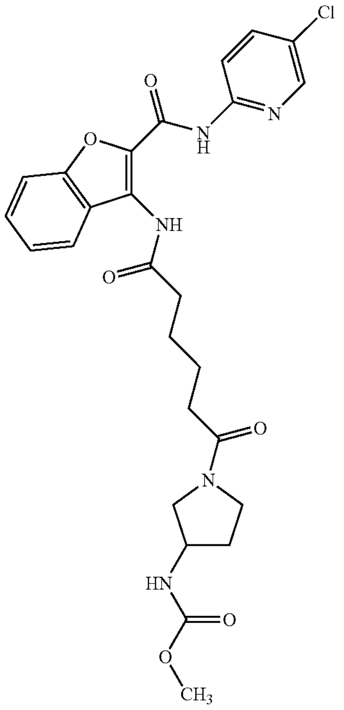 | APCI-MS M/Z:542/544 $[M + H]^+$ |
| 83 | 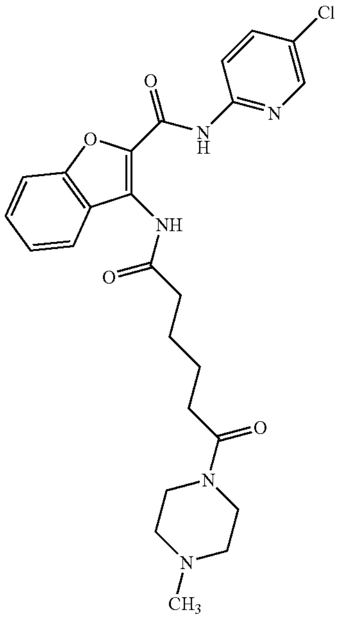 | APCI-MS M/Z:498/500 $[M + H]^+$ |

-continued
| EX. NO. | Structure | Physicochemical Properties |
|---|---|---|
| 84 | 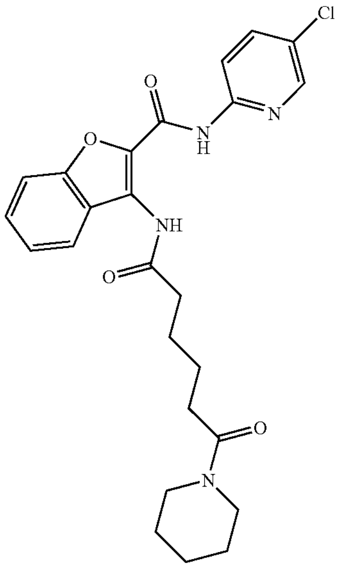 | APCI-MS M/Z:483/485 [M + H]+ |
| 85 | 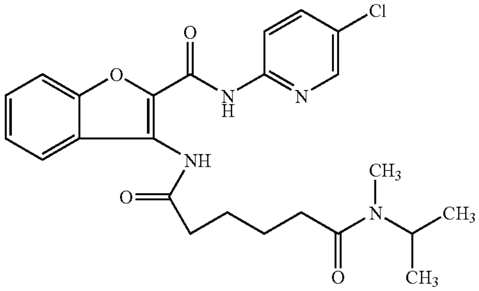 | APCI-MS M/Z:471/473 [M + H]+ |
| 86 | 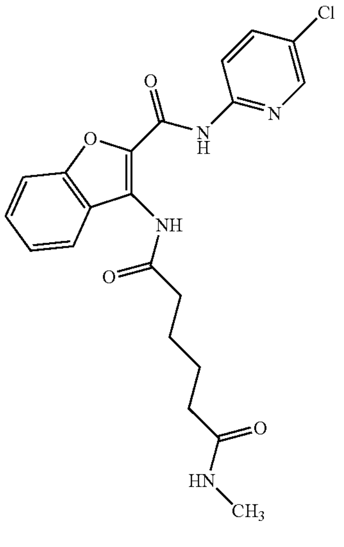 | APCI-MS M/Z:429/431 [M + H]+ |

-continued
| EX. NO. | Structure | Physicochemical Properties |
|---|---|---|
| 87 | 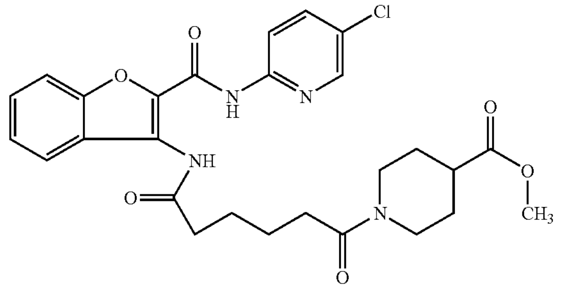 | APCI-MS M/Z:541/543 [M + H]+ |
| 88 | 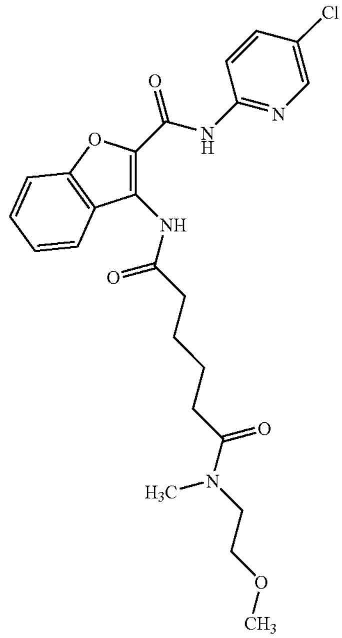 | APCI-MS M/Z:487/489 [M + H]+ |
| 89 | 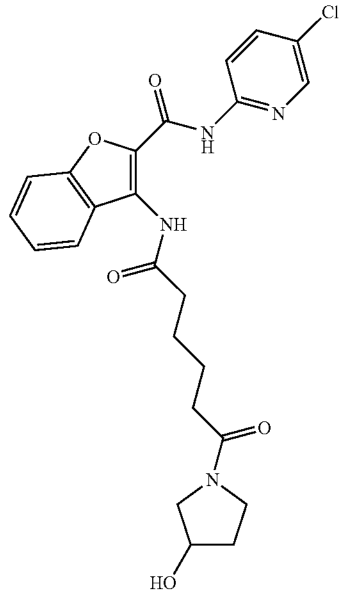 | APCI-MS M/Z:485/487 [M + H]+ |

-continued
| EX. NO. | Structure | Physicochemical Properties |
|---|---|---|
| 90 | 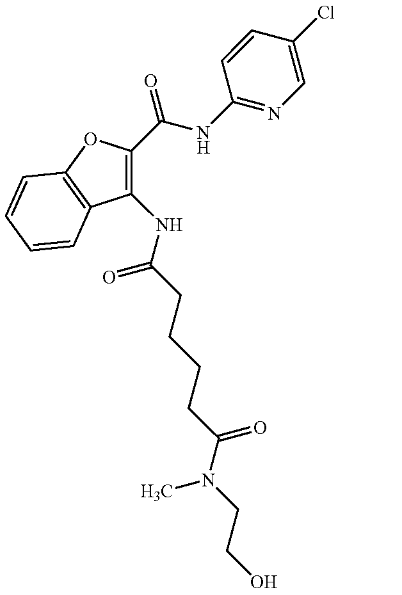 | APCI-MS M/Z:473/475 [M + H]$^+$ |
| 91 | 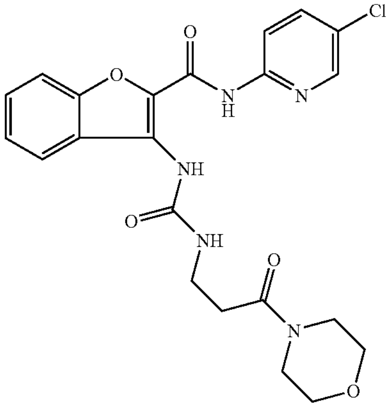 | APCI-MS M/Z:472/474 [M + H]$^+$ |
| 92 | 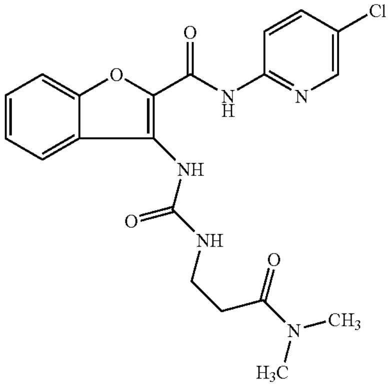 | APCI-MS M/Z:430/432 [M + H]$^+$ |
Examples 93-95
The amino compounds and carboxylic acids obtained in Reference Examples are treated in a similar manner to Example 1 to give the following compounds.

| EX. NO. | Structure | Physicochemical Properties |
|---|---|---|
| 93 | 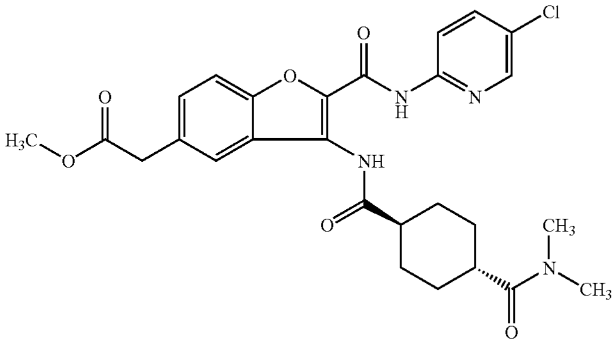 | APCI-MS M/Z:521 [M + H]$^+$ |
| 94 | 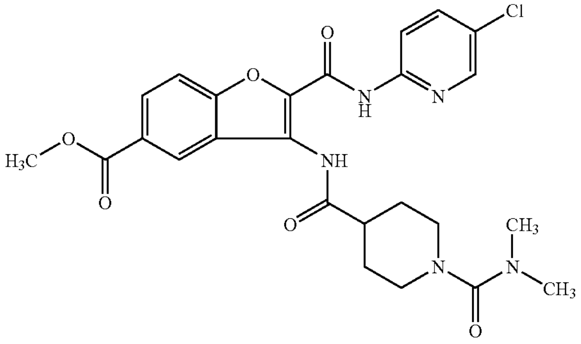 | APCI-MS M/Z:528/530 [M + H]$^+$ |
| 95 | 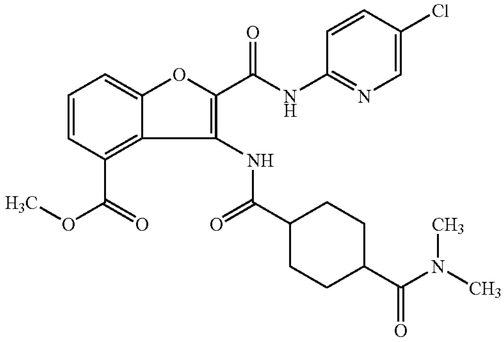 | APCI-MS M/Z:521/523 [M + H]$^+$ |
Examples 96-98
The corresponding carboxylic acid esters are tested in a similar manner to Example 5 to give the following compounds.

| EX. NO. | Structure | Physicochemical Properties |
|---|---|---|
| 96 | 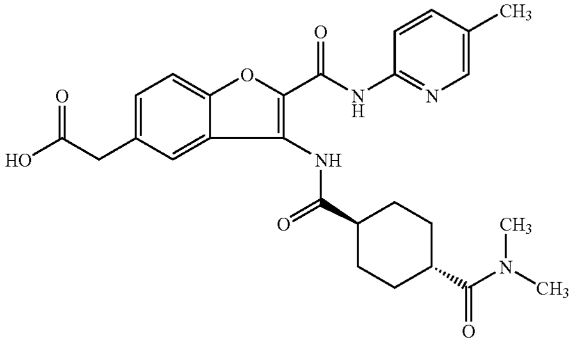 | APCI-MS M/Z:507 [M + H]$^+$ |
| 97 | 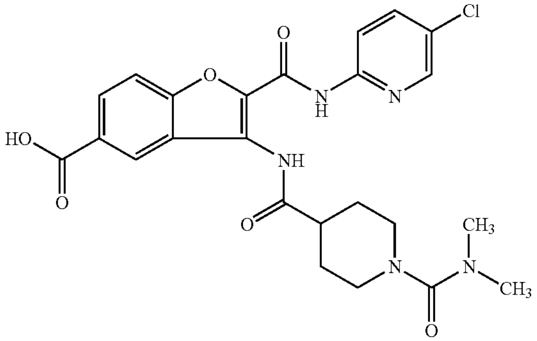 | ESI-MS M/Z:512/514 [M − H]$^-$ |
| 98 | 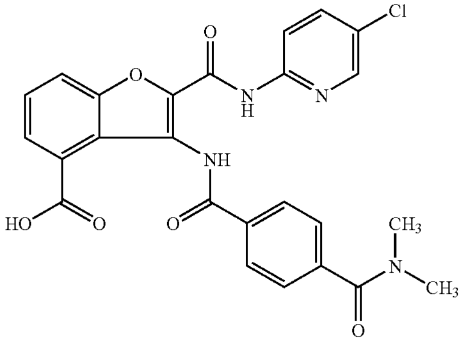 | ESI-MS M/Z:505/507 [M − H]$^-$ |
Examples 99-123
The corresponding carboxylic acids and the corresponding amino compounds are treated in a similar manner to Example 6 to give the following compounds.

| EX. NO. | Structure | Physicochemical Properties |
|---|---|---|
| 99 | 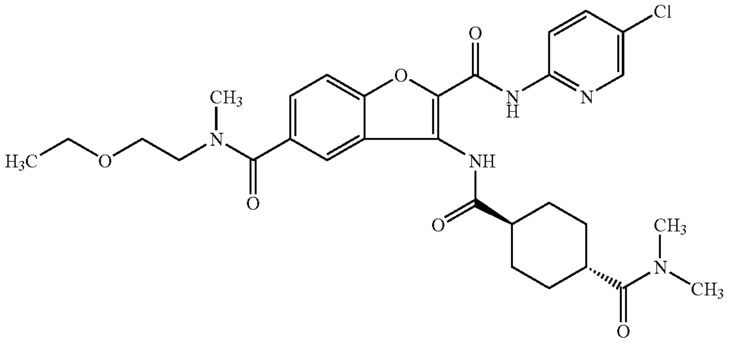 | APCI-MS M/Z:598/600 [M + H]+ |
| 100 | 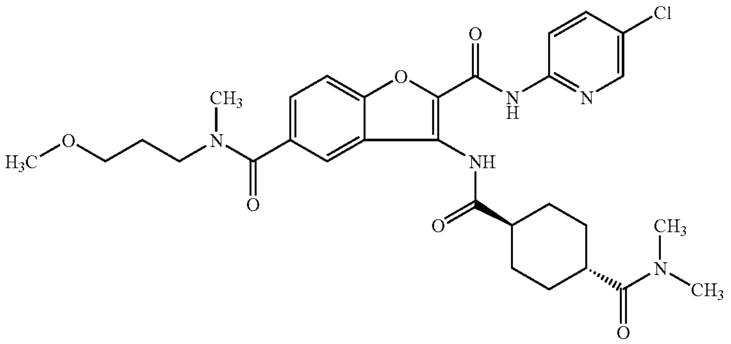 | APCI-MS M/Z:598/600 [M + H]+ |
| 101 | 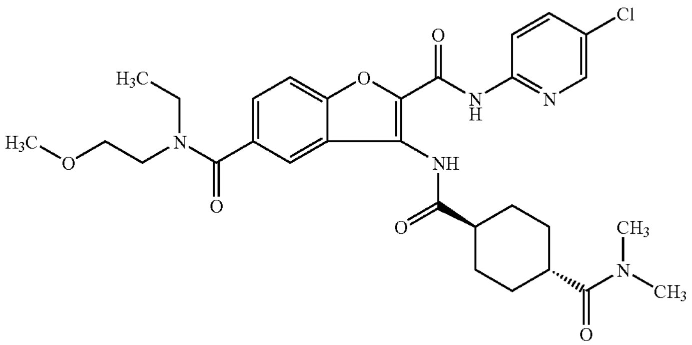 | APCI-MS M/Z:598/600 [M + H]+ |
| 102 | 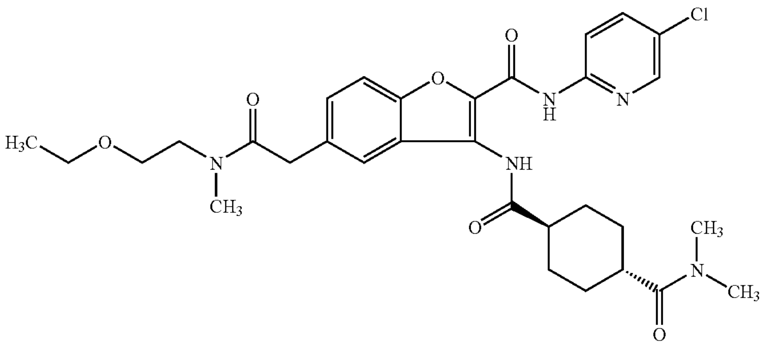 | APCI-MS M/Z:612/614 [M + H]+ |

-continued
| EX. NO. | Structure | Physicochemical Properties |
|---|---|---|
| 103 | 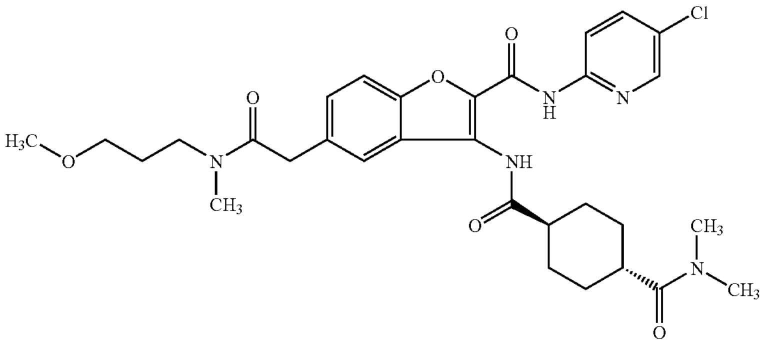 | APCI-MS M/Z:612/614 [M + H]$^+$ |
| 104 | 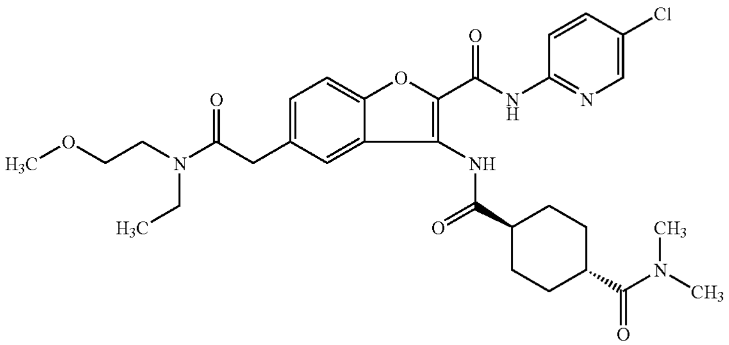 | APCI-MS M/Z:612/614 [M + H]$^+$ |
| 105 | 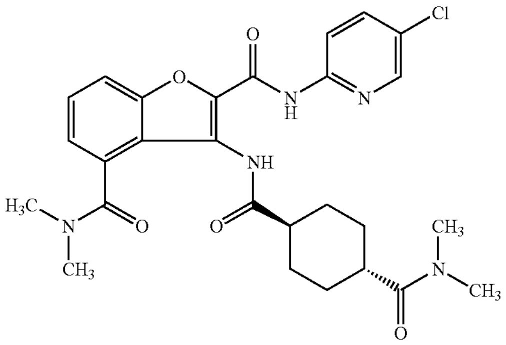 | APCI-MS M/Z:540/542 [M + H]$^+$ |
| 106 | 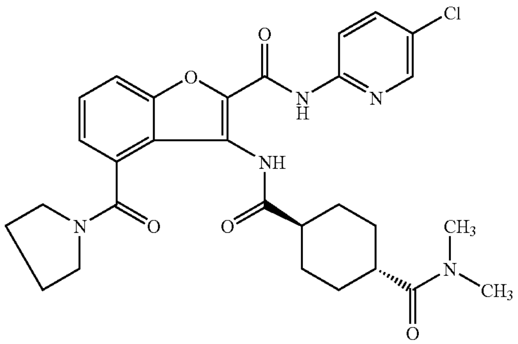 | APCI-MS M/Z:566/568 [M + H]$^+$ |

-continued
| EX. NO. | Structure | Physicochemical Properties |
|---|---|---|
| 107 | 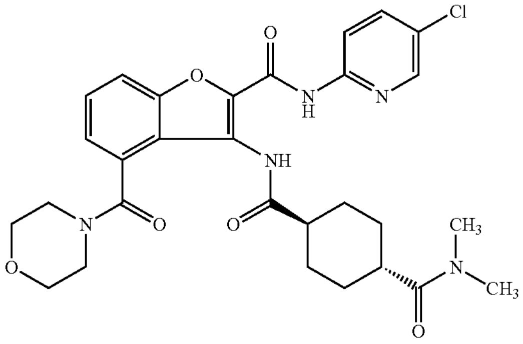 | APCI-MS M/Z:582/584 $[M + H]^+$ |
| 108 | 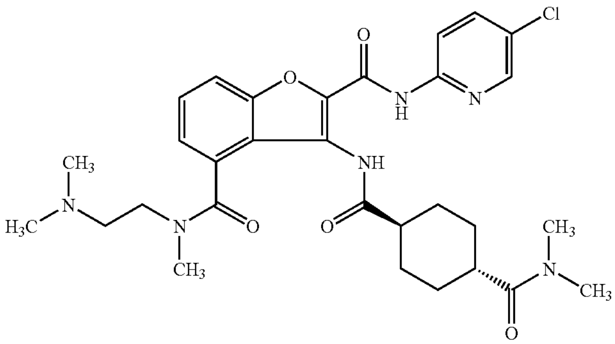 | APCI-MS M/Z:597/599 $[M + H]^+$ |
| 109 | 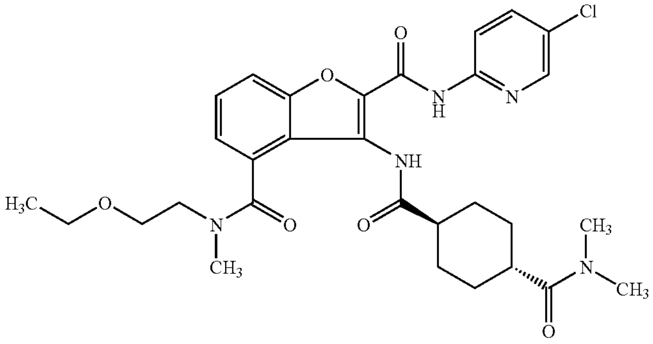 | APCI-MS M/Z:598/600 $[M + H]^+$ |
| 110 | 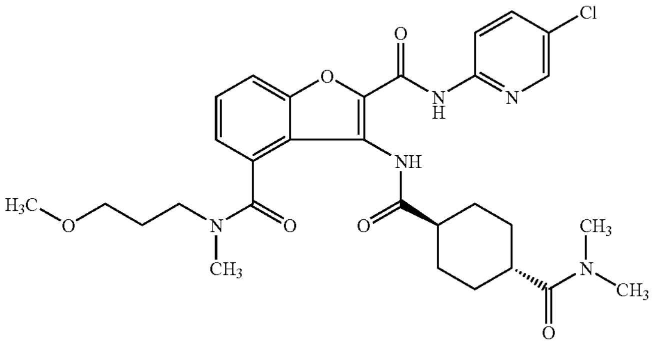 | APCI-MS M/Z:598/600 $[M + H]^+$ |

-continued
| EX. NO. | Structure | Physicochemical Properties |
|---|---|---|
| 111 | 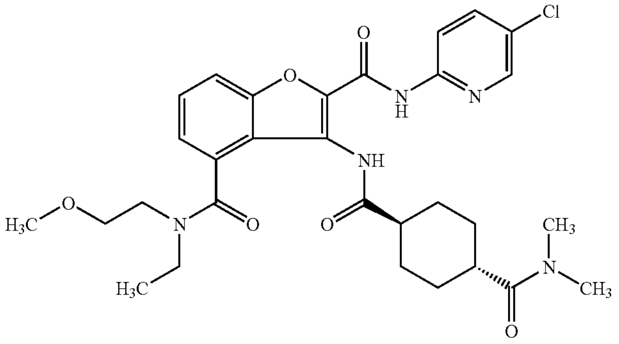 | APCI-MS M/Z:598/600 $[M + H]^+$ |
| 112 | 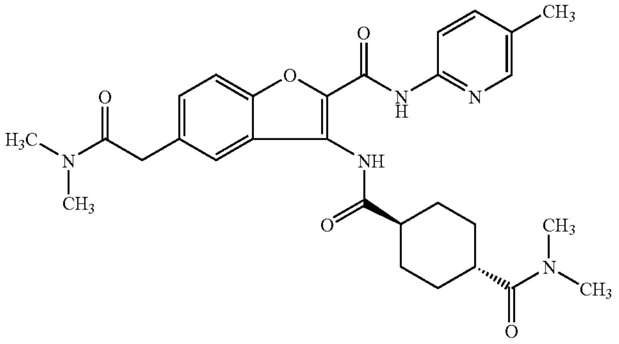 | APCI-MS M/Z:534 $[M + H]^+$ |
| 113 | 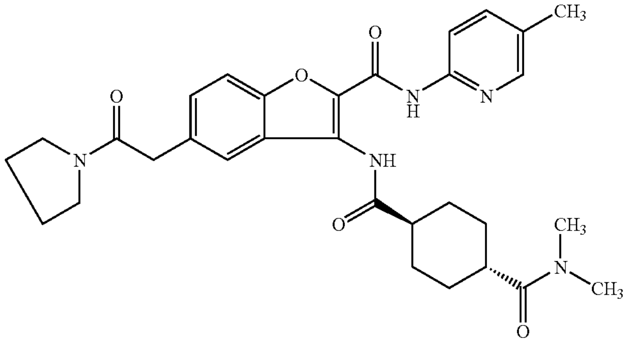 | APCI-MS M/Z:560 $[M + H]^+$ |
| 114 | 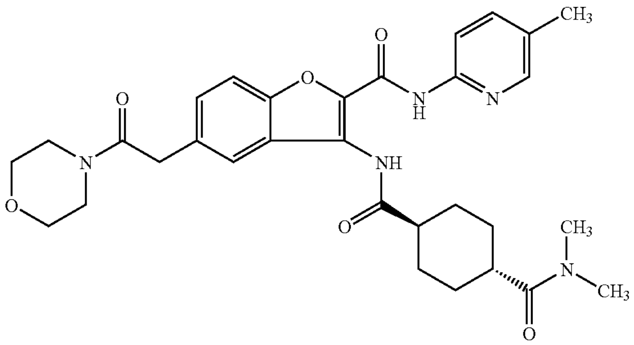 | APCI-MS M/Z:576 $[M + H]^+$ |

-continued
| EX. NO. | Structure | Physicochemical Properties |
|---|---|---|
| 115 | 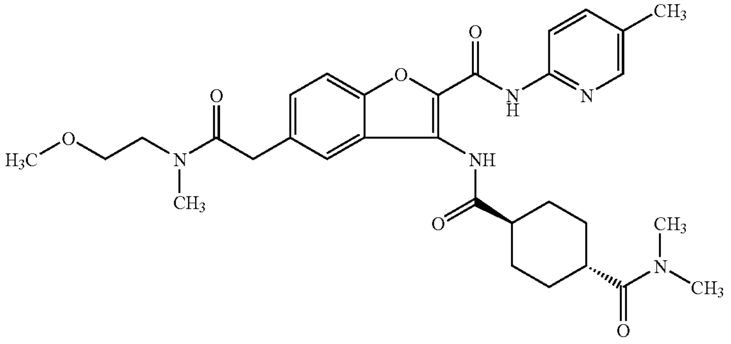 | APCI-MS M/Z:578 [M + H]+ |
| 116 | 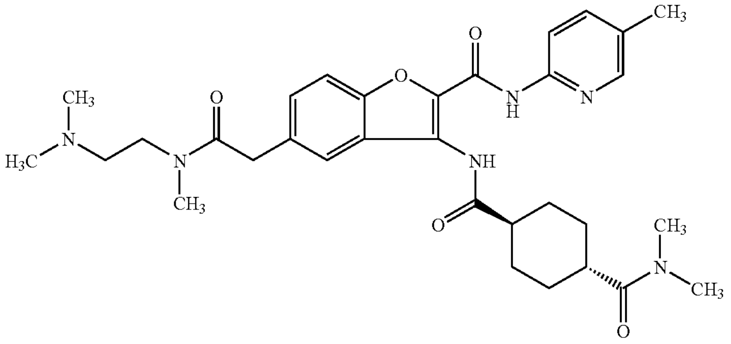 | APCI-MS M/Z:591 [M + H]+ |
| 117 | 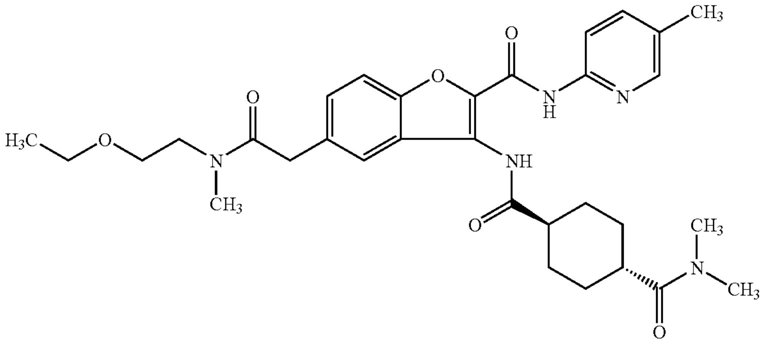 | APCI-MS M/Z:592 [M + H]+ |
| 118 | 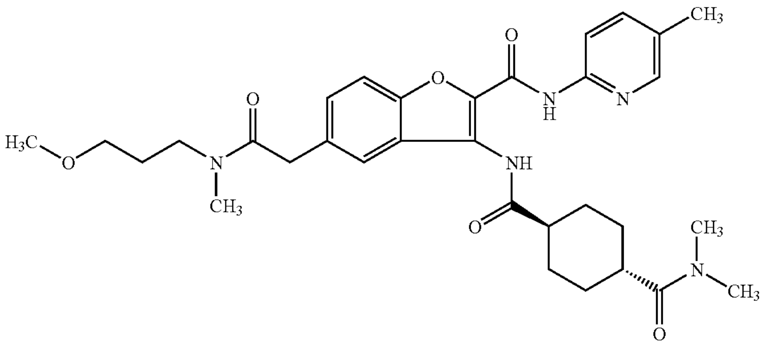 | APCI-MS M/Z:592 [M + H]+ |

-continued
| EX. NO. | Structure | Physicochemical Properties |
|---|---|---|
| 119 | 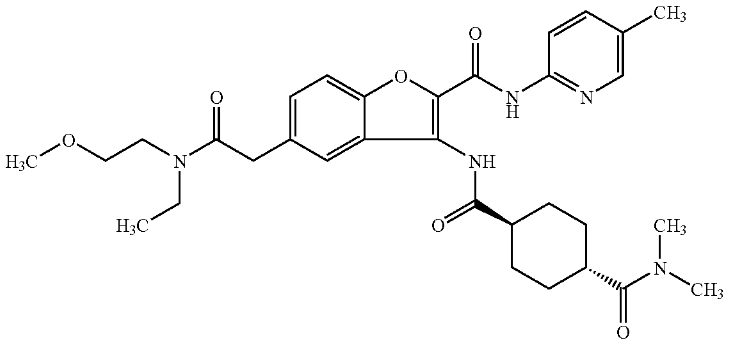 | APCI-MS M/Z:592 [M + H]$^+$ |
| 120 | 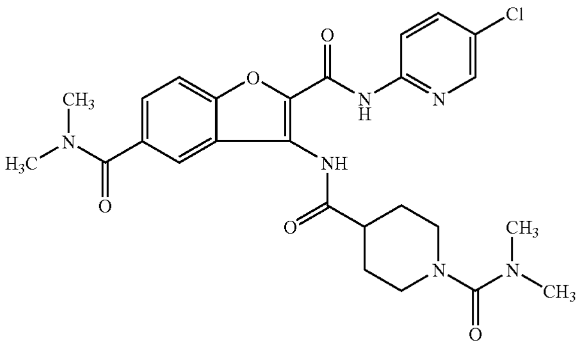 | APCI-MS M/Z:541/543 [M + H]$^+$ |
| 121 | 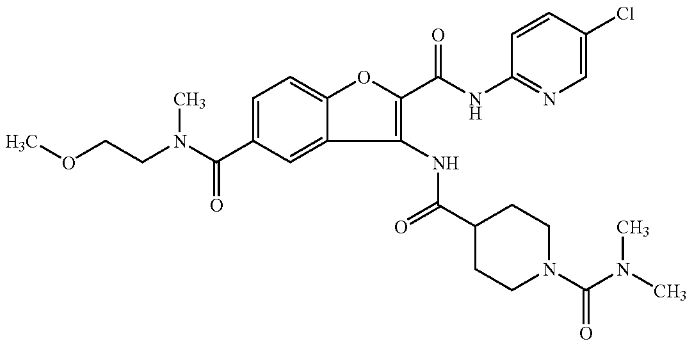 | APCI-MS M/Z:585/587 [M + H]$^+$ |
| 122 | 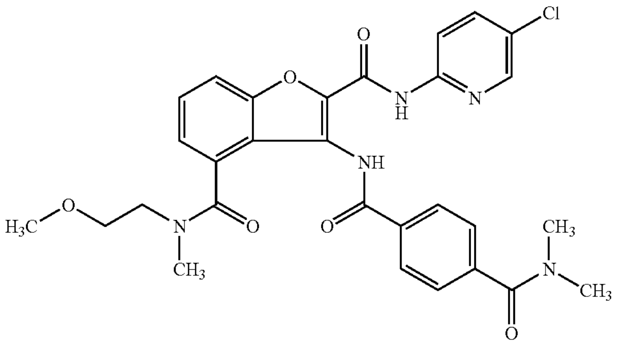 | APCI-MS M/Z:578/580 [M + H]$^+$ |

-continued

| EX. NO. | Structure | Physicochemical Properties |
|---|---|---|
| 123 | 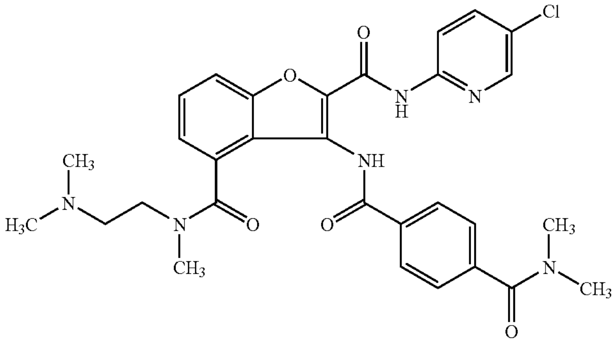 | APCI-MS M/Z:591/593 [M + H]$^+$ |

Examples 124-125

The corresponding amino compounds and carboxylic acids are treated in a similar manner to Example 1 to give the following compounds.

| EX. NO. | Structure | Physicochemical Properties |
|---|---|---|
| 124 | 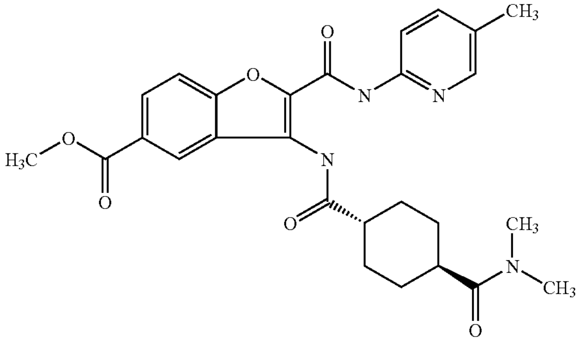 | |
| 125 | 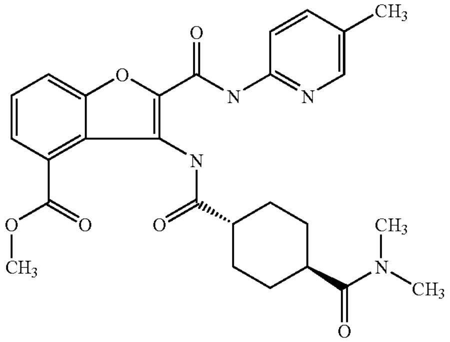 | |

Examples 126-127

The corresponding carboxylic acid esters are treated in a similar manner to Example 5 to give the following compounds.

| EX. NO. | Structure | Physicochemical Properties |
|---|---|---|
| 126 | 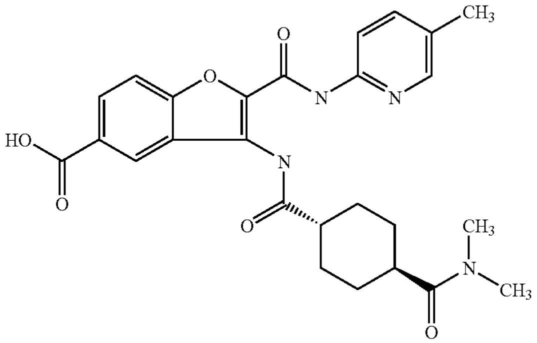 | |
| 127 | 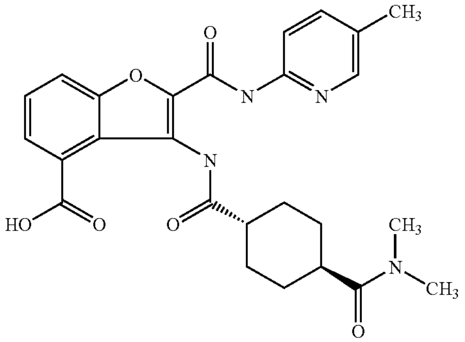 | |
Examples 128-143
The corresponding carboxylic acids and the corresponding amino compounds are treated in a similar manner to Example 6 to give the following compounds.
| EX. NO. | Structure | Physicochemical Properties |
|---|---|---|
| 128 | 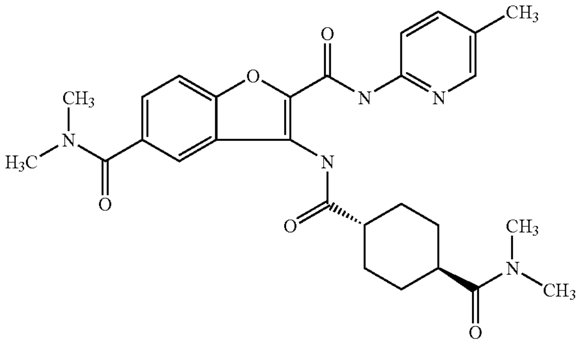 | |

-continued
| EX. NO. | Structure | Physicochemical Properties |
|---|---|---|
| 129 | 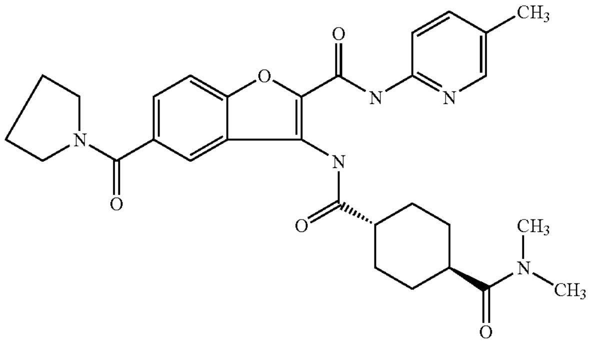 | |
| 130 | 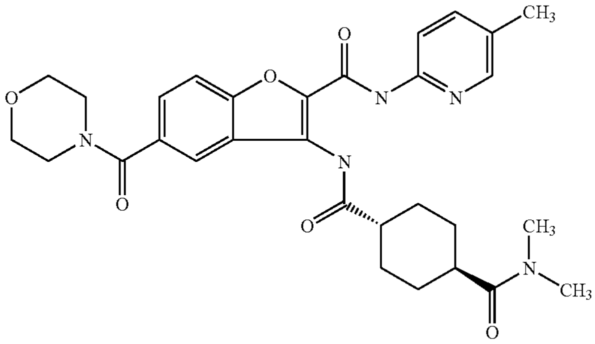 | |
| 131 | 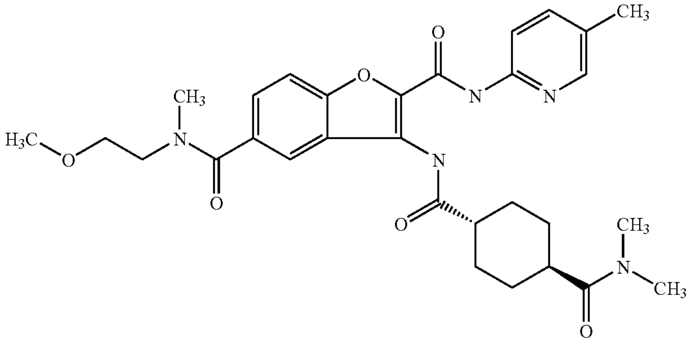 | |
| 132 | 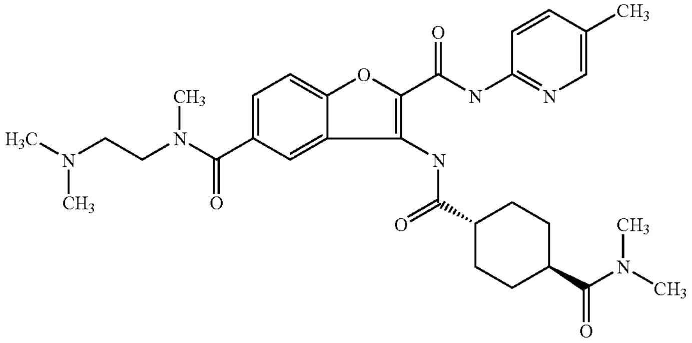 | |

-continued
| EX. NO. | Structure | Physicochemical Properties |
| --- | --- | --- |
| 133 | 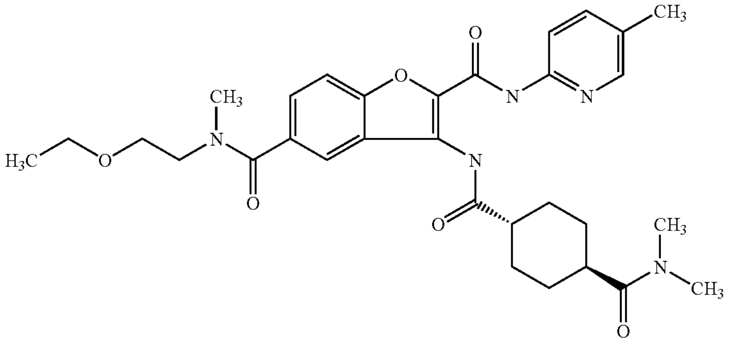 | |
| 134 | 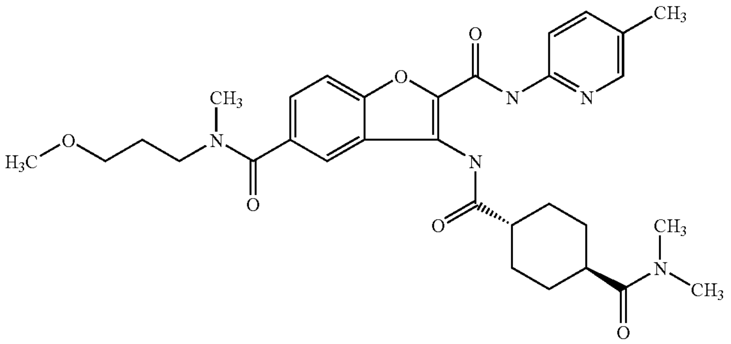 | |
| 135 | 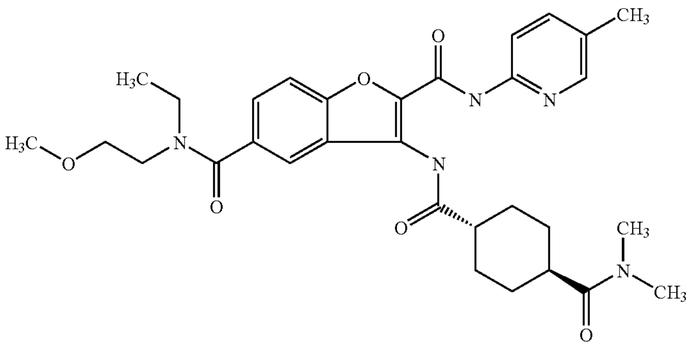 | |
| 136 | 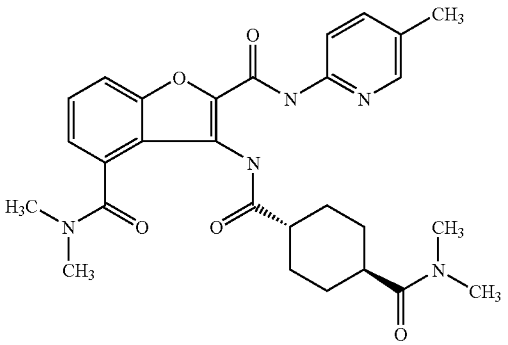 | |

-continued
| EX. NO. | Structure | Physicochemical Properties |
|---|---|---|
| 137 | 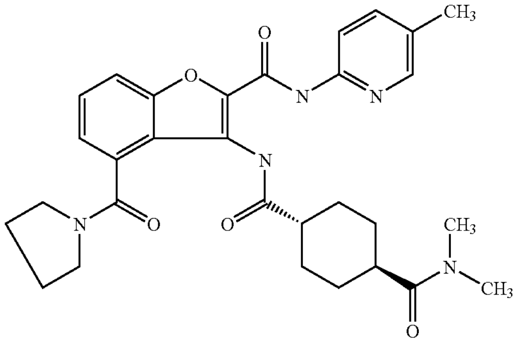 | |
| 138 | 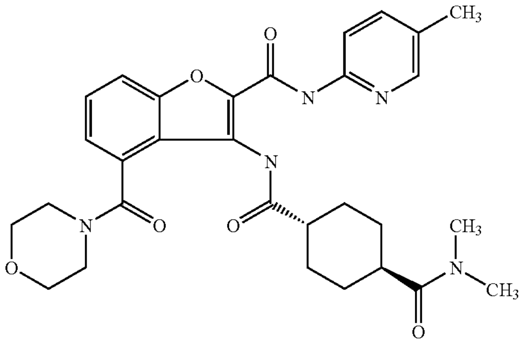 | |
| 139 | 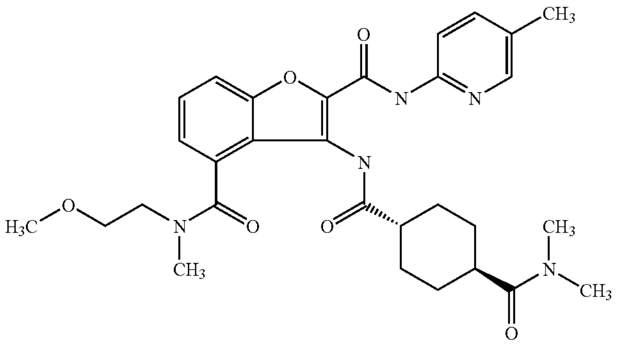 | |
| 140 | 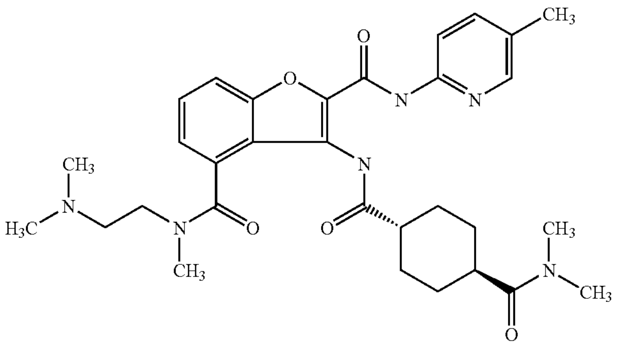 | |

-continued

| EX. NO. | Structure | Physicochemical Properties |
|---|---|---|
| 141 | 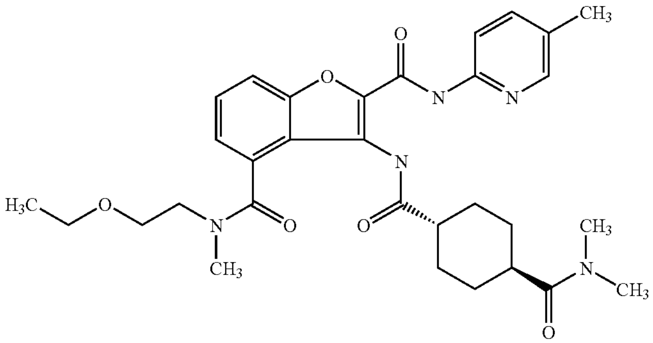 | |
| 142 | 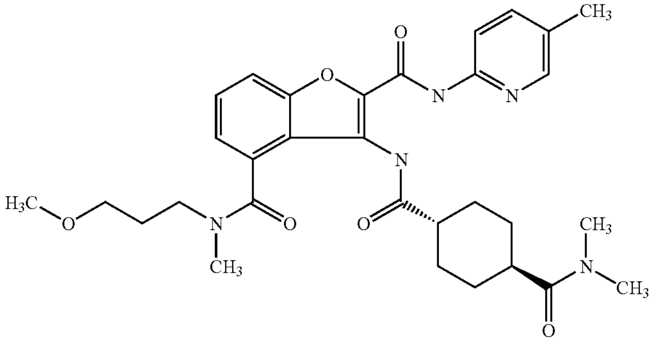 | |
| 143 | 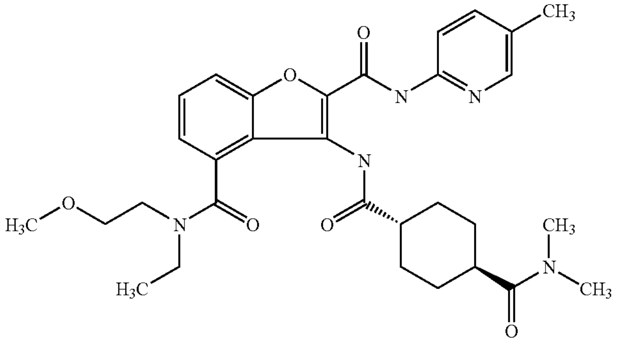 | |

Reference Example 1 trans-4-[(Dimethylamino)carbonyl]-cyclohexanecarboxylic acid

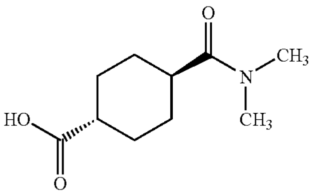

(1) Thionyl chloride (254 ml) is added dropwise to methanol (1500 ml) under cooling at −30° C. over a period of about an hour. After the addition, the reaction mixture is stirred at room temperature for 0.5 hours, and thereto is added trans-cyclohexane-1,4-dicarboxylic acid (500.0 g), and the mixture is stirred at room temperature for 17 hours. The reaction solution is concentrated under reduced pressure. The residue is diluted with chloroform, and washed with a saturated aqueous sodium hydrogen carbonate solution and saturated brine. The organic layer is dried over sodium sulfate and evaporated to remove the solvent under reduced pressure. The resulting residue is crystallized from n-hexane. The product is collected by filtration and dried to give dimethyl trans-cyclohexane-1,4-dicarboxylate (545.0 g). APCI-MS M/Z:201[M+H]$^+$ (2) Dimethyl trans-cyclohexane-1,4-dicarboxylate (150.0 g) obtained in (1) above is dissolved in tetrahydrofuran (1500 ml), and to the solution is added dropwise a mixed solution of 28% sodium methoxide/methanol (149 g) and water (13.2 g) under ice-cooling. The reaction solution is warmed to room temperature, stirred for 3.5 hours, and thereto is poured n-hexane (1500 ml). The mixture is filtered to collect the precipitates. The resulting solid precipitates are added to a mixture of conc. hydrochloric acid (50 ml), water (450 ml) and chloroform (1000 ml) under ice-cooling, and the mixture is stirred at room temperature for 20 minutes. The chloroform layer is separated and the aqueous layer is extracted with chloroform. The organic layers are combined, dried over sodium sulfate and evaporated to remove the solvent under reduced pressure. The resulting residue is crystallized from n-hexane, collected by filtration and dried to give trans-4-(methoxycarbonyl)cyclohexanecarboxylic acid (106.0 g). ESI-MS M/Z:185[M−H]$^-$ (3) trans-4-(Methoxycarbonyl)cyclohexanecarboxylic acid (20.0 g) obtained in (2) above is dissolved in chloroform (200 ml), and thereto are added dimethylamine hydrochloride (10.5 g), 1-ethyl-3-(3-dimethylaminopropyl)-carbodiimide hydrochloride (24.7 g) and triethylamine (26.0 g) under ice-cooling. The mixture is then stirred at room temperature for 17 hours. Ice-water is poured to the reaction solution and the mixture is extracted with chloroform. The organic layer is washed successively with 10 % hydrochloric acid, a saturated aqueous sodium hydrogen carbonate solution and saturated brine, and dried over sodium sulfate. The solvent is concentrated under reduced pressure. The resulting residue is purified by silica gel column chromatography (eluent: chloroform, then chloroform/methanol=20/1) to give methyl trans-4-[(dimethylamino)carbonyl]cyclohexanecarboxylate (20.1 g).

APCI-MS M/Z:214[M+H]$^+$ (4) Methyl trans-4-[(dimethylamino)carbonyl]-cyclohexanecarboxylate (20.0 g) obtained in (3) above is dissolved in methanol (100 ml), and thereto is added a solution of sodium hydroxide (7.50 g) in water (40 ml). The mixture is then stirred at room temperature for 18 hours. The reaction solution is concentrated under reduced pressure, and the residue is diluted with ice-water and washed with diethyl ether. The resulting aqueous layer is acidified with 10% hydrochloric acid and extracted twice with chloroform. The organic layer is washed with saturated brine and dried over sodium sulfate. The solvent is concentrated under reduced pressure. The resulting residue is suspended in n-hexane and collected by filtration to give the title compound (15.7 g).

ESI-MS M/Z:198[M−H]$^-$

Reference Example 2 trans-4-(Pyrrolidin-1-ylcarbonyl)-cyclohexanecarboxylic acid

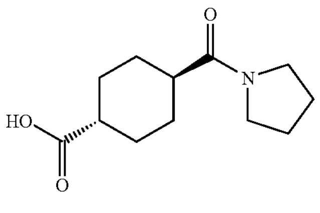

(1) trans-4-(Methoxycarbonyl)cyclohexanecarboxylic acid (20.0 g) obtained in Reference Example 1(2) is dissolved in chloroform (200 ml), and thereto are added pyrrolidine (9.2 g), 1-ethyl-3-(3-dimethylaminopropyl)-carbodiimide hydrochloride (24.7 g) and triethylamine (13.6 g) under ice-cooling. The mixture is then stirred at room temperature for 17 hours. Ice-water is poured to the reaction solution and the mixture is extracted with chloroform. The organic layer is washed successively with 10% hydrochloric acid, a saturated aqueous sodium hydrogen carbonate solution and saturated brine, and dried over sodium sulfate. The solvent is concentrated under reduced pressure. The resulting residue is purified by silica gel column chromatography (eluent: chloroform, then chloroform/methanol=20/1) to give methyl trans-4-(pyrrolidin-1-ylcarbonyl)cyclohexanecarboxylate (11.8 g).

APCI-MS M/Z:240[M+H]$^+$ (2) Methyl trans-4-(pyrrolidin-1-ylcarbonyl)-cyclohexanecarboxylate (11.7 g) obtained in (1) above is dissolved in methanol (50 ml), and thereto is added a solution of sodium hydroxide (3.95 g) in water (20 ml). The mixture is then stirred at room temperature for 18 hours. The reaction solution is concentrated under reduced pressure. The residue is diluted with ice-water and washed with diethyl ether. The resulting aqueous layer is acidified with 10% hydrochloric acid and extracted twice with chloroform. The organic layer is washed with saturated brine and dried over sodium sulfate. The solvent is concentrated under reduced pressure. The resulting residue is suspended in n-hexane and collected by filtration to give the title compound (10.1 g).

ESI-MS M/Z:224[M−H]$^-$

Reference Example 3 trans-4-(Morpholin-4-ylcarbonyl)-cyclohexanecarboxylic acid

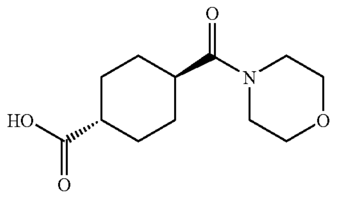

(1) trans-4-(Methoxycarbonyl)cyclohexanecarboxylic acid (800 mg) obtained in Reference Example 1(2) is dissolved in chloroform (30 ml), and thereto are added morpholine (560 mg), 1-ethyl-3-(3-dimethylaminopropyl)-carbodiimide hydrochloride (1.24 g) and triethylamine (650 mg) under ice-cooling. The mixture is then stirred at room temperature for 19 hours. Ice-water is poured to the reaction solution and the mixture is extracted with chloroform. The organic layer is washed successively with 10% hydrochloric acid, a saturated aqueous sodium hydrogen carbonate solution and saturated brine and dried over sodium sulfate. The solvent is concentrated under reduced pressure. The resulting residue is purified by silica gel column chromatography (eluent: chloroform, then chloroform/methanol=30/1) to give methyl trans-4-(morpholin-4-ylcarbonyl)cyclohexanecarboxylate (897 mg).

APCI-MS M/Z:256[M+H]$^+$ (2) Methyl trans-4-(morpholin-4-ylcarbonyl)-cyclohexanecarboxylate (860 mg) obtained in (1) above is dissolved in methanol (40 ml), and thereto is added 4 N aqueous sodium hydroxide solution (1.68 ml). The mixture is then stirred at room temperature for 18 hours. The reaction solution is concentrated under reduced pressure. The residue is diluted with ice-water, neutralized with 10% hydrochloric acid, and extracted with chloroform. The organic layer is dried over sodium sulfate and the solvent is concentrated under reduced pressure to give the title compound (638 mg). ESI-MS M/Z: 240[M−H]$^-$ Reference Example 4 trans-4-{[[2-(Dimethylamino)ethyl]-(methyl)amino]carbonyl}cyclohexanecarboxylic acid

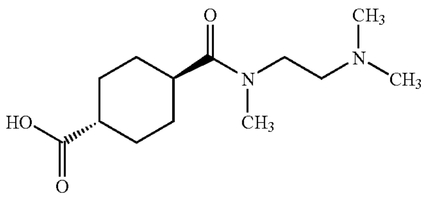

(1) trans-4-(Methoxycarbonyl)cyclohexanecarboxylic acid (8.84 g) obtained in Reference Example 1(2) is dissolved in chloroform (100 ml), and thereto are added 1-hydroxybenzotriazole (7.14 g), 1-ethyl-3-(3-dimethyl-aminopropyl)carbodiimide hydrochloride (10.00 g) and N,N,N'-trimethylethylenediamine (5.33 g) under ice-cooling. The mixture is then stirred at room temperature for 4 hours. Saturated aqueous sodium hydrogen carbonate solution is poured to the reaction solution and the mixture is extracted with chloroform. The organic layer is washed with saturated brine and dried over sodium sulfate. The solvent is concentrated under reduced pressure. The resulting residue is purified by silica gel column chromatography (eluent: chloroform/methanol/28% ammonia water=200/10/1) to give methyl trans-4-{[[2-(dimethylamino)ethyl](methyl)amino]carbonyl}-cyclohexanecarboxylate-(11.98 g). APCI-MS M/Z:271[M+H]$^+$ (2) Methyl trans-4-{[[2-(dimethylamino)ethyl](methyl)-amino]carbonyl}cyclohexanecarboxylate (6.32 g) obtained in (1) above is dissolved in methanol (20 ml), and thereto is added 1 N aqueous sodium hydroxide solution (25 ml). The mixture is stirred at room temperature for 3 hours. To the reaction solution is added 1 N hydrochloric acid (25 ml) and the reaction solution is concentrated under reduced pressure. The residue is lyophilized to give the crude title compound which contains equimolar sodium chloride (6.71 g). APCI-MS M/Z:257[M+H]$^+$ Reference Example 5

6-Morpholin-4-yl-6-oxohexanoic acid

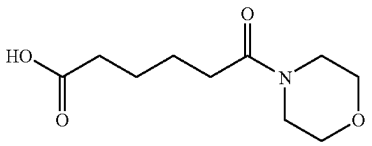

(1) Monomethyl adipate (3.20 g) is dissolved in chloroform (70 ml), and thereto are added morpholine (2.61 g), 1-ethyl-3-(3-dimethylaminopropyl)carbodiimide hydrochloride (5.75 g) and triethylamine (3.04 g) under ice-cooling. The mixture is then stirred at room temperature for 19 hours. Ice-water is added to the reaction solution and the mixture is extracted with chloroform. The organic layer is washed successively with 10% hydrochloric acid, a saturated aqueous sodium hydrogen carbonate solution and saturated brine, and dried over sodium sulfate. The solvent is removed by evaporation under reduced pressure to give methyl 6-morpholin-4-yl-6-oxohexanoate (4.63 g). APCI-MS M/Z:230[M+H]$^+$ (2) Methyl 6-morpholin-4-yl-6-oxohexanoate (4.60 g) obtained in (1) above is dissolved in methanol (20 ml), and thereto is added a solution of sodium hydroxide (1.61 g) in water (8 ml). The mixture is stirred at room temperature for 19 hours. The reaction solution is concentrated under reduced pressure and the residue is neutralized with 2 N hydrochloric acid. The residue is concentrated under reduced pressure and extracted with chloroform. The organic layer is dried over sodium sulfate and the solvent is concentrated under reduced pressure to give the title compound (4.11 g). ESI-MS M/Z: 214[M−H]$^-$ Reference Example 6

5-Morpholin-4-yl-5-oxopentanoic acid

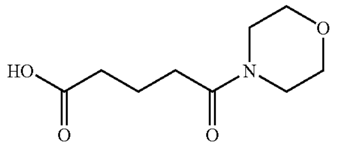

Glutaric anhydride (1.14 g) is dissolved in tetrahydrofuran (20 ml), and thereto is added morpholine (0.87 g). The mixture is then stirred at room temperature for 19 hours. The reaction solution is concentrated under reduced pressure, and the residue is diluted with chloroform and washed with 10% hydrochloric acid. The organic layer is dried over sodium sulfate and evaporated to remove the solvent under reduced pressure to give the title compound (1.05 g). ESI-MS M/Z: 200[M−H]$^-$ Reference Example 7

Methyl 3-formyl-4-hydroxybenzoate

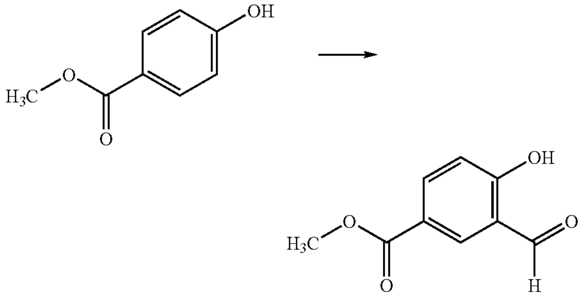

Methyl 4-hydroxybenzoate (1.52 g) is dissolved in trifluoroacetic acid (20 ml), and thereto is added hexamethylenetetramine (700 mg). The mixture is heated under reflux for 2 hours. The reaction solution is concentrated under reduced pressure, and thereto is poured ice-water. The mixture is then extracted with ethyl acetate. The organic layer is washed with a saturated aqueous sodium hydrogen carbonate solution and saturated brine, dried over sodium sulfate and evaporated to remove the solvent under reduced pressure. The resulting residue is dissolved in chloroform, and filtered to remove the insoluble materials. The filtrate is concentrated under reduced pressure, and purified by silica gel column chromatography (eluent: n-hexane/ethyl acetate=4/1) to give the title compound (540 mg). ESI-MS M/Z:179[M−H]$^-$ Reference Example 8

Methyl (3-formyl-4-hydroxyphenyl)-acetate

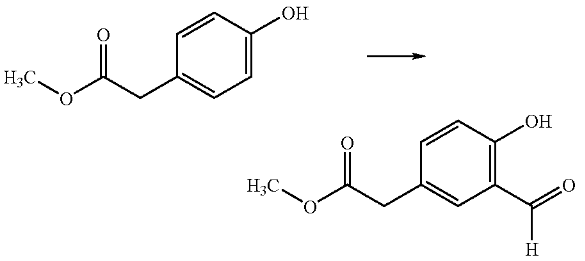

Methyl (4-hydroxyphenyl)acetate (1.66 g) is dissolved in trifluoroacetic acid (20 ml), thereto is added hexamethylenetetramine (700 mg), and the mixture is heated under reflux for 2 hours. The reaction solution is concentrated under reduced pressure, thereto is poured ice-water, and then the mixture is extracted with ethyl acetate. The organic layer is washed with a saturated aqueous sodium hydrogen carbonate solution and saturated brine, dried over sodium sulfate, and evaporated to remove the solvent under reduced pressure. The resulting residue is purified by silica gel column chromatography (eluent: n-hexane/ethyl acetate =9/1, then 4/1) to give the title compound (1.08 g). ESI-MS M/Z:193[M−H]$^-$ Reference Examples 9-10

The corresponding starting compounds are treated in a similar manner to Reference Example 7 or Reference Example 8 to give the following compounds.

Reference Example 11

Methyl 3-cyano-4-hydroxybenzoate

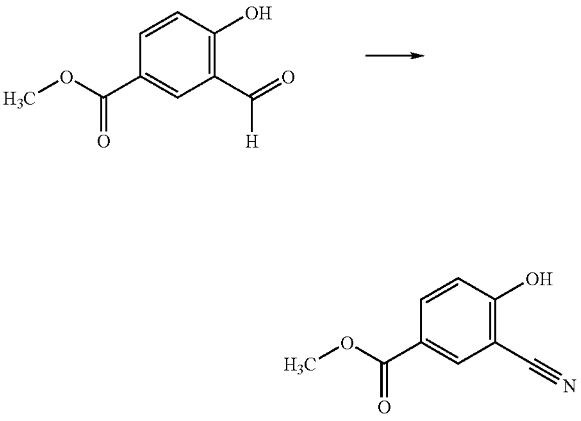

Methyl 3-formyl-4-hydroxybenzoate (28.60 g) obtained in Reference Example 7 is dissolved in formic acid (120 ml), thereto is added hydroxylammonium chloride (14.30 g), and the mixture is heated under reflux for 15 hours. The reaction solution is concentrated under reduced pressure, diluted with ethyl acetate, washed successively with water and saturated brine, dried over sodium sulfate and evaporated to remove the solvent under reduced pressure to give the title compound (24.25 g). ESI-MS M/Z:176[M−H]$^-$

| Ref. Ex. No. | Structure | Physicochemical Properties |
|---|---|---|
| 9 | 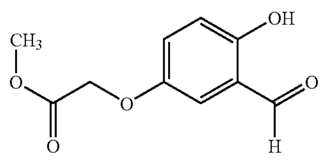 | APCI-MS M/Z:225 [M + H + MeOH − $H_2O$]$^+$ |
| 10 | 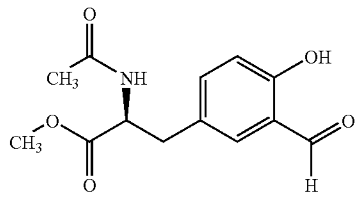 | EI-MS M/Z:265 [M]$^+$ |

Reference Example 12

Methyl (3-cyano-4-hydroxyphenyl)-acetate

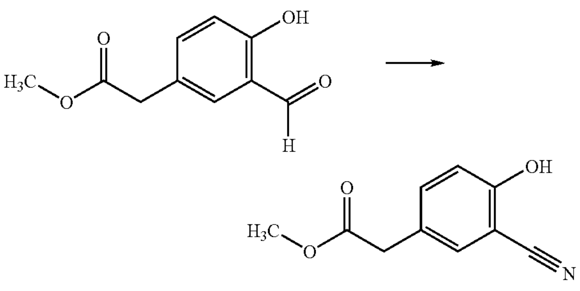

Methyl (3-formyl-4-hydroxyphenyl)acetate (1.05 g) obtained in Reference Example 8 is dissolved in formic acid (15 ml), and thereto are added hydroxylammonium chloride (0.49 g) and sodium formate (0.81 g), and the mixture is heated under reflux for 8 hours. The reaction solution is concentrated under reduced pressure, diluted with ethyl acetate, washed successively with water and saturated brine, dried over sodium sulfate, and evaporated to remove the solvent under reduced pressure to give the title compound (520 mg). ESI-MS M/Z:190[M−H]$^-$ Reference Examples 13-25

The corresponding starting compounds are treated in a similar manner to Reference Example 11 or 12 to give the following compounds.

| Ref. Ex. No. | Structure | Physico-chemical Properties |
|---|---|---|
| 13 | 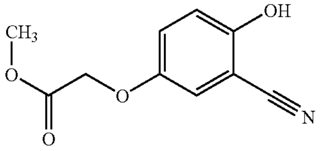 | ESI-MS M/Z:192 [M − H]$^-$ |
| 14 | 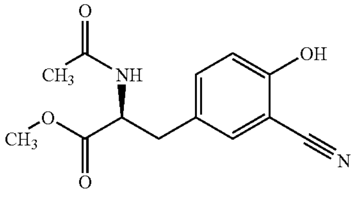 | APCI-MS M/Z:263 [M + H]$^+$ |
| 15 | 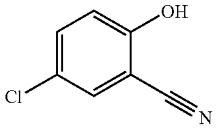 | ESI-MS M/Z:152/154 [M − H]$^-$ |
| 16 | 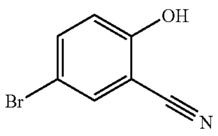 | ESI-MS M/Z:196/198 [M − H]$^-$ |

-continued

| Ref. Ex. No. | Structure | Physico-chemical Properties |
|---|---|---|
| 17 | 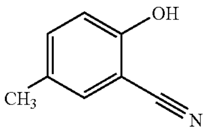 | ESI-MS M/Z:132 [M − H]$^-$ |
| 18 | 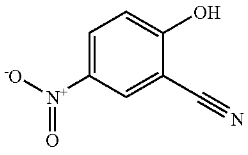 | ESI-MS M/Z:163 [M − H]$^-$ |
| 19 | 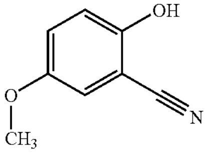 | ESI-MS M/Z:148 [M − H]$^-$ |
| 20 | 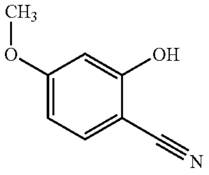 | ESI-MS M/Z:148 [M − H]$^-$ |
| 21 | 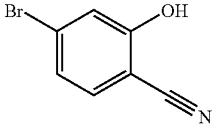 | ESI-MS M/Z:196/198 [M − H]$^-$ |
| 22 | 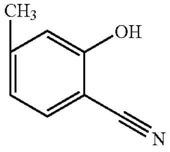 | ESI-MS M/Z:132 [M − H]$^-$ |
| 23 | 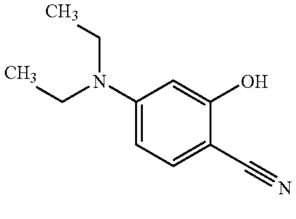 | This compound is used in the next step without further purification. |
| 24 | 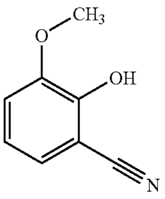 | ESI-MS M/Z:148 [M − H]$^-$ |

-continued

| Ref. Ex. No. | Structure | Physico-chemical Properties |
|---|---|---|
| 25 | 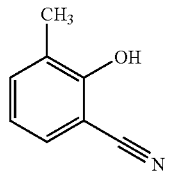 | This compound is used in the next step without further purification. |

Reference Example 26

2-(4-Methoxycarbonyl-2-cyano-phenoxy)-N-(5-chloropyridin-2-yl)acetamide

1)

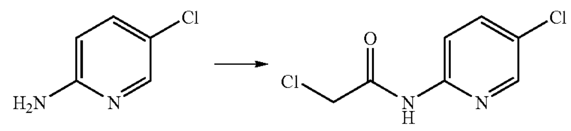

2)

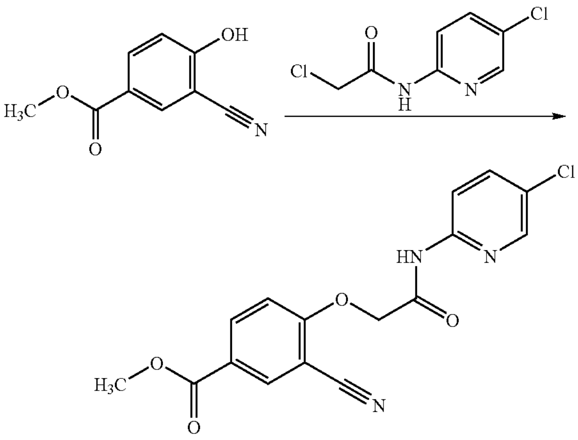

(1) Chloroacetyl chloride (95.5 ml) is dissolved in dichloromethane (500 ml), and thereto is added dropwise a suspension of 2-amino-5-chloropyridine (128.6 g) and triethylamine (169 ml) in dichloromethane (1000 ml) under ice-cooling. The reaction solution is warmed to room temperature and stirred for 0.5 hours. The reaction solution is concentrated under reduced pressure, and thereto is poured ice-water. The reaction mixture is extracted with ethyl acetate. The organic layer is washed with saturated brine, dried over sodium sulfate and treated with activated charcoal. Insoluble materials are removed by filtration and the filtrate is concentrated under reduced pressure. The resulting residue is suspended in diisopropyl ether. The precipitates are collected by filtration, washed with diisopropyl ether and dried to give 2-chloro-N-(5-chloropyridin-2-yl)acetamide (153.4 g).

APCI-MS M/Z:205/207$[M+H]^+$ (2) Methyl 3-cyano-4-hydroxybenzoate (500 mg) obtained in Reference Example 11 is dissolved in acetone (25 ml), and thereto are added 2-chloro-N-(5-chloropyridin-2-yl)acetamide (695 mg) obtained in (1) above, potassium carbonate (546 mg) and sodium iodide (550 mg). The mixture is heated under reflux for 2 hours. After allowing to cool, insoluble materials are removed by filtration and the insolubles are washed with acetone several times. The filtrate and washings are combined, concentrated under reduced pressure, and purified by silica gel column chromatography (eluent: chloroform, then chloroform/ethyl acetate=4/1). The resulting residue is suspended in diethyl ether, and the precipitates are collected by filtration to give the title compound (660 mg).

APCI-MS M/Z:346/348$[M+H]^+$

Reference Example 27

2-[2-Cyano-4-(methoxycarbonyl-methyl)phenoxy]-N-(5-chloropyridin-2-yl)acetamide

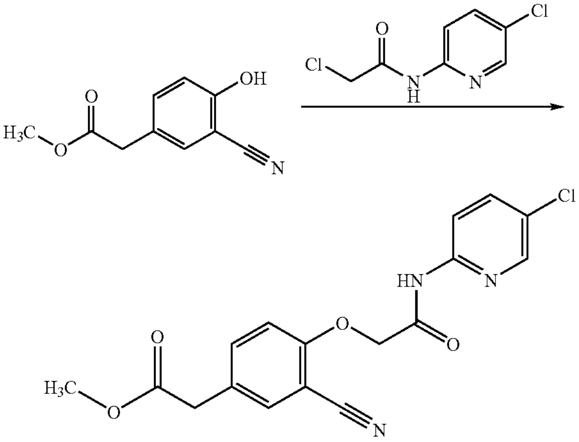

Methyl (3-cyano-4-hydroxyphenyl)acetate (500 mg) obtained in Reference Example 12 is dissolved in acetone (25 ml), and thereto are added 2-chloro-N-(5-chloropyridin-2-yl) acetamide (640 mg) obtained in Reference Example 26(1), cesium carbonate (1.20 g) and sodium iodide (510 mg). The mixture is heated under reflux for 5 hours. After allowing to cool, the insoluble materials are removed by filtration and the insolubles are washed with acetone several times. The filtrate and the washings are combined and concentrated under reduced pressure. To the residue is poured water, and the mixture is extracted with ethyl acetate. The organic layer is washed with saturated brine, dried over sodium sulfate and evaporated to remove the solvent under reduced pressure. The resulting residue is purified by silica gel column chromatography (eluent: n-hexane/ethyl acetate/chloroform=3/1/1) The resulting residue is suspended in diethyl ether-n-hexane, and the precipitates are collected by filtration to give the title compound (570 mg). APCI-MS M/Z:360/362$[M+H]^+$ Reference Example 28-29

The corresponding starting compounds are treated in a similar manner to Reference Example 26 or 27 to give the following compounds.

| Ref. Ex. No. | Structure | Physicochemical Properties |
|---|---|---|
| 28 | 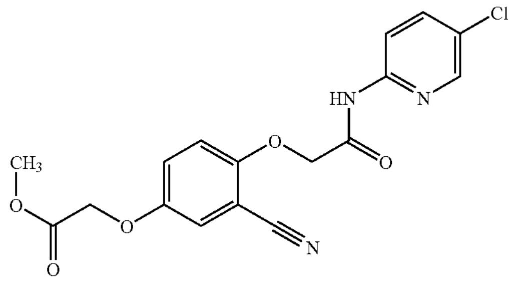 | APCI-MS M/Z:376/378 [M + H]$^+$ |
| 29 | 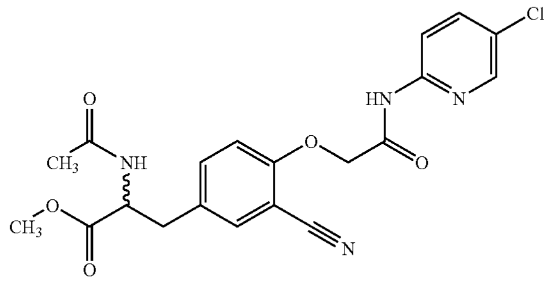 | APCI-MS M/Z:431/433 [M + H]$^+$ |

Reference Example 30 t-Butyl (2-cyanophenoxy)acetate

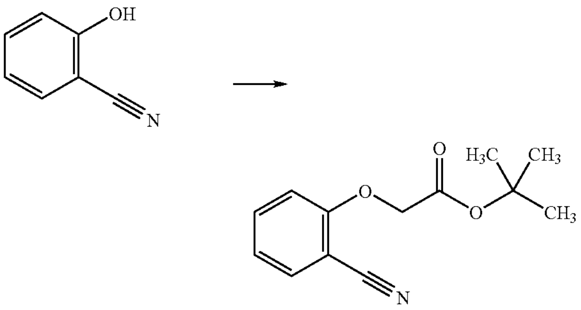

2-Cyanophenol (107.1 g) is dissolved in acetone (1000 ml) and thereto is added t-butyl bromoacetate (200.0 g). Potassium carbonate (141.6 g) is added, and the reaction solution is heated under reflux for 2 hours. After allowing to cool, the insoluble materials are removed by filtration, and the insolubles are washed with acetone several times. The filtrate and washings are combined, concentrated under reduced pressure and treated with diisopropyl ether azeotropically. The resulting residue is crystallized from n-hexane-diisopropyl ether (5/1) (600 ml), followed by stirring under ice-cooling. The precipitates are collected by filtration, washed with cold n-hexane-diisopropyl ether (10/1) (600 ml) several times, and dried to give the title compound (194.5 g).

APCI-MS M/Z:251[M+NH$_4$]$^+$

Reference Examples 31-42

The corresponding starting compounds are treated in a similar manner to Reference Example 30 to give the following compounds.

| Ref. Ex. No. | Structure | Physicochemical Properties |
|---|---|---|
| 31 | 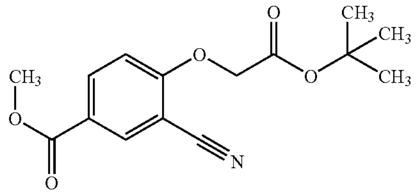 | APCI-MS M/Z:309 [M + NH$_4$]$^+$ |

-continued
| Ref. Ex. No. | Structure | Physicochemical Properties |
|---|---|---|
| 32 | 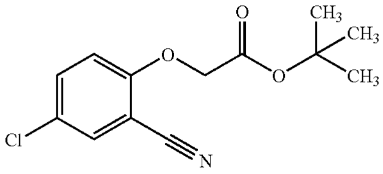 | APCI-MS M/Z:285/287 $[M + NH_4]^+$ |
| 33 | 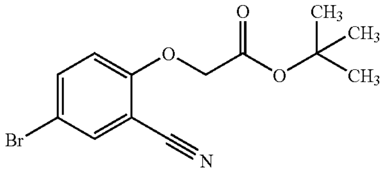 | APCI-MS M/Z:329/331 $[M + NH_4]^+$ |
| 34 | 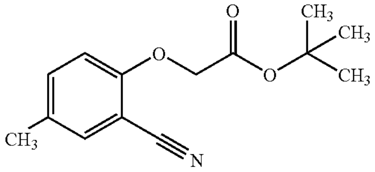 | APCI-MS M/Z:265 $[M + NH_4]^+$ |
| 35 | 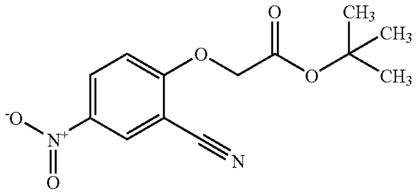 | APCI-MS M/Z:296 $[M + NH_4]^+$ |
| 36 | 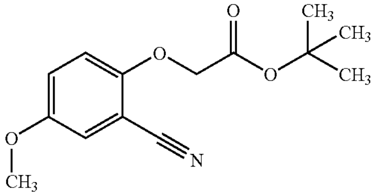 | APCI-MS M/Z:281 $[M + NH_4]^+$ |
| 37 | 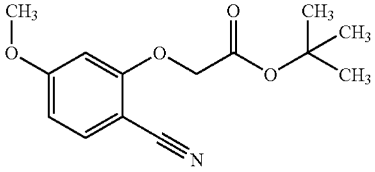 | APCI-MS M/Z:281 $[M + NH_4]^+$ |
| 38 | 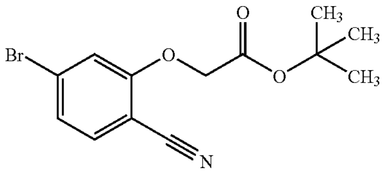 | APCI-MS M/Z:329/331 $[M + NH_4]^+$ |
| 39 | 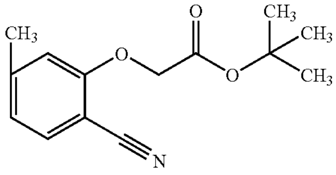 | APCI-MS M/Z:265 $[M + NH_4]^+$ |

-continued

| Ref. Ex. No. | Structure | Physicochemical Properties |
|---|---|---|
| 40 | 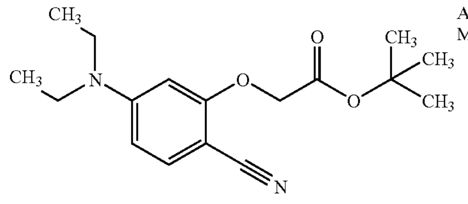 | APCI-MS M/Z:305 $[M+H]^+$ |
| 41 | 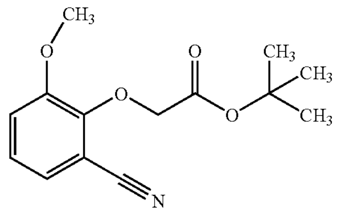 | APCI-MS M/Z:281 $[M+NH_4]^+$ |
| 42 | 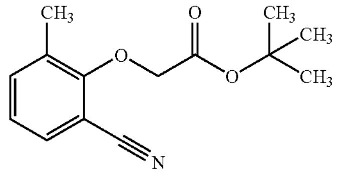 | APCI-MS M/Z:265 $[M+NH_4]^+$ |

Reference Example 43

(2-Cyanophenoxy)acetic acid

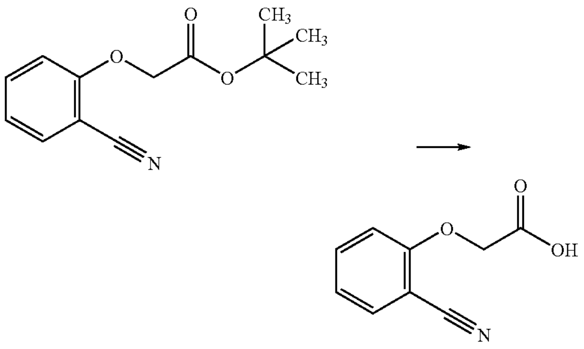

t-Butyl (2-cyanophenoxy)acetate (300.0 g) obtained in Reference Example 30 is dissolved in dichloromethane (400 ml), and thereto is added trifluoroacetic acid (990 ml) and the mixture is stirred at room temperature for 4 hours. The reaction solution is concentrated under reduced pressure, and the resulting residue is suspended in diethyl ether (100 ml). To the suspension is poured diisopropyl ether (500 ml). The precipitates are collected by filtration, washed with diisopropyl ether several times and dried to give the title compound (198.4 g).

ESI-MS M/Z:176$[M-H]^-$

Reference Examples 44-55

The corresponding starting compounds are treated in a similar manner to Reference Example 43 to give the following compounds.

| Ref. Ex. No. | Structure | Physicochemical Properties |
|---|---|---|
| 44 | 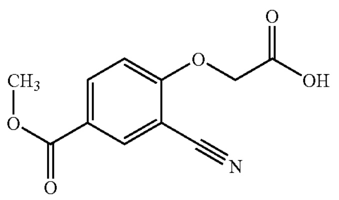 | ESI-MS M/Z:234 $[M-H]^-$ |

-continued
| Ref. Ex. No. | Structure | Physicochemical Properties |
|---|---|---|
| 45 | 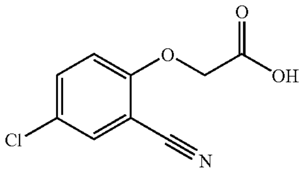 | ESI-MS M/Z:210/212 [M − H]$^-$ |
| 46 | 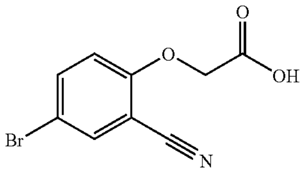 | ESI-MS M/Z:254/256 [M − H]$^-$ |
| 47 | 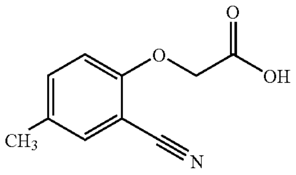 | ESI-MS M/Z:190 [M − H]$^-$ |
| 48 | 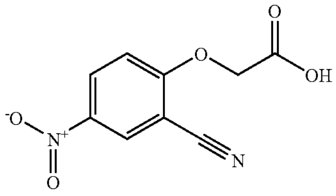 | ESI-MS M/Z:221 [M − H]$^-$ |
| 49 | 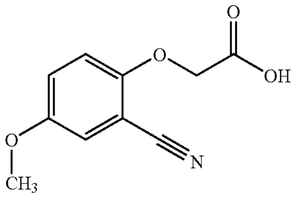 | ESI-MS M/Z:206 [M − H]$^-$ |
| 50 | 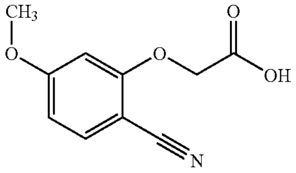 | ESI-MS M/Z:206 [M − H]$^-$ |
| 51 | 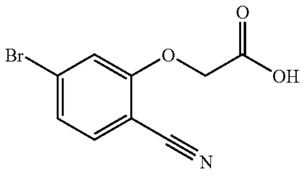 | ESI-MS M/Z:254/256 [M − H]$^-$ |
| 52 | 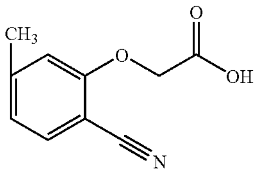 | ESI-MS M/Z:190 [M − H]$^-$ |

-continued

| Ref. Ex. No. | Structure | Physicochemical Properties |
|---|---|---|
| 53 | 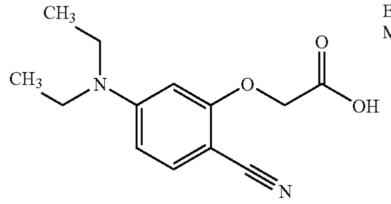 | ESI-MS M/Z:247 [M − H]⁻ |
| 54 | 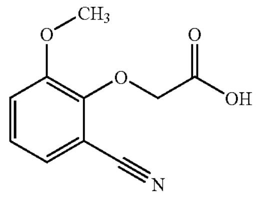 | ESI-MS M/Z:206 [M − H]⁻ |
| 55 | 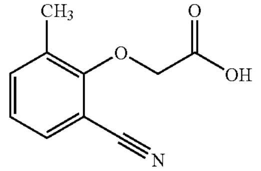 | ESI-MS M/Z:190 [M − H]⁻ |

Reference Example 56

[4-(N-Benzyloxycarbonyl-N-methyl-amino)-2-cyanophenoxy]acetic acid

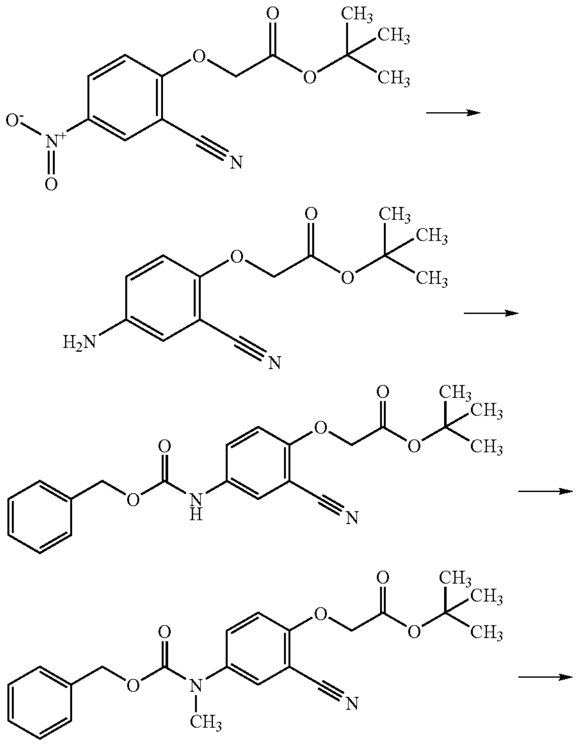

-continued

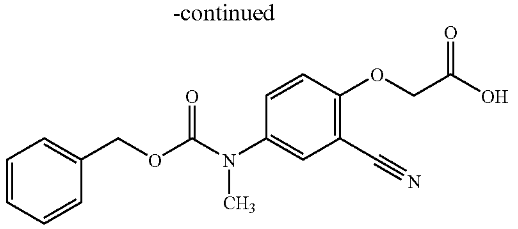

(1) t-Butyl 2-(4-nitro-2-cyanophenoxy)acetate (500 mg) obtained in Reference Example 35 is dissolved in tetrahydrofuran (20 ml), and thereto is added 10% palladium-carbon (100 mg) The mixture is stirred for 2 hours under atmospheric hydrogen pressure. The insoluble materials are removed by filtration, and the filtrate is concentrated under reduced pressure to give t-butyl (4-amino-2-cyanophenoxy) acetate (440 mg).

APCI-MS M/Z:249[M+H]$^+$ (2) t-Butyl (4-amino-2-cyanophenoxy)acetate (430 mg) obtained in (1) above is dissolved in tetrahydrofuran (10 ml), and thereto is added a saturated sodium hydrogen carbonate solution (10 ml). Benzyl chloroformate (355 mg) is further added under ice-cooling. Under ice-cooling, the reaction solution is stirred for 1 hour and extracted with ethyl acetate. The organic layer is washed with saturated brine, dried over sodium sulfate, and evaporated to remove the solvent under reduced pressure. The resulting residue is purified by silica gel column chromatography (eluent: n-hexane/ethyl acetate=9/1, then 3/1) to give t-butyl (4-benzyloxycarbonylamino-2-cyanophenoxy) acetate (540 mg).

APCI-MS M/Z:383[M+H]$^+$ (3) t-Butyl (4-benzyloxycarbonylamino-2-cyanophenoxy) acetate (100 mg) obtained in (2) above is dissolved in N,N-dimethylformamide (3 ml) and thereto is added 60% oleaginous sodium hydride (12.5 mg). After stirring for 20 minutes at room temperature, methyl iodide (24.4 μl) is added dropwise and the mixture is further stirred for one hour. To the reaction solution is poured a saturated aqueous ammonium chloride solution and extracted with ethyl acetate. The organic layer is washed successively with water and saturated brine, dried over sodium sulfate and evaporated to remove the solvent. The resulting residue is purified by silica gel column chromatography (eluent: n-hexane/ethyl acetate=9/1, then 3/1) to give t-butyl [4-(N-benzyloxycarbonyl-N-methylamino)-2-cyanophenoxy]acetate (91 mg). APCI-MS M/Z: 414$[M+NH_4]^+$ (4) t-Butyl [4-(N-benzyloxycarbonyl-N-methylamino)-2-cyanophenoxy]acetate (2.42 g) obtained in (3) above is treated in a similar manner to Reference Example 43 to give the title compound (2.06 g). ESI-MS M/Z:339$[M-H]^-$ Reference Example 57

(2-Cyanophenoxy)-N-(5-chloropyridin-2-yl)acetamide

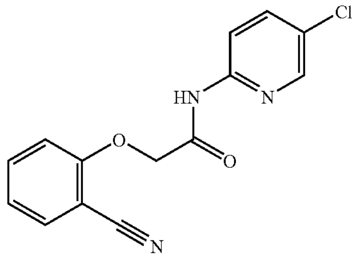

(2-Cyanophenoxy)acetic acid (48.63 g) obtained in Reference Example 43 is dissolved in dichloromethane (1000 ml), thereto are added oxalyl chloride (26.34 ml) and N,N-dimethylformamide (10 drops), and the mixture is stirred at room temperature for 3.5 hours. The reaction solution is cooled on ice-bath, and thereto is added 2-amino-5-chloropyridine (32.08 g), followed by addition of pyridine (60.54 ml). After 5 minutes, the reaction solution is warmed to room temperature and stirred overnight. After adding ice-water, the solution is adjusted to about pH 4 with 10% hydrochloric acid, and extracted with chloroform. The organic layer is washed successively with water, a saturated aqueous sodium hydrogen carbonate solution and saturated brine, dried over sodium sulfate and evaporated to remove the solvent. The resulting residue is suspended in chloroform-ethyl acetate and collected by filtration to give (2-cyanophenoxy)-N-(5-chloropyridin-2-yl)acetamide (51.58 g). The filtrate is concentrated under reduced pressure, and purified by silica gel column chromatography (eluent: chloroform) to give the title compound (11.50 g).

APCI-MS M/Z:288/290$[M+H]^+$

Reference Examples 58-72

The corresponding starting compounds are treated in a similar manner to Reference Example 57 to give the following compounds.

| Ref. Ex. No. | Structure | Physicochemical Properties |
| --- | --- | --- |
| 58 | 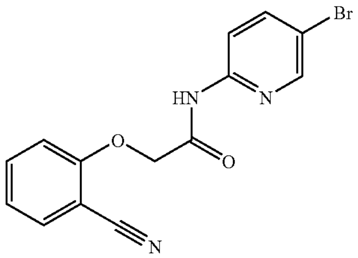 | APCI-MS M/Z:332/334 $[M + H]^+$ |
| 59 | 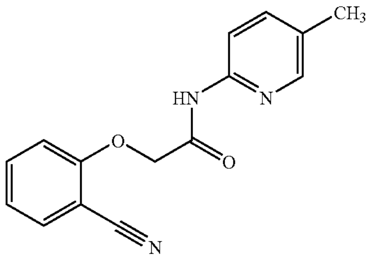 | APCI-MS M/Z:268 $[M + H]^+$ |

-continued
| Ref. Ex. No. | Structure | Physicochemical Properties |
|---|---|---|
| 60 | 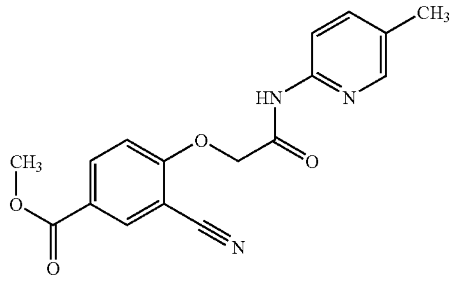 | APCI-MS M/Z:326 [M + H]$^+$ |
| 61 | 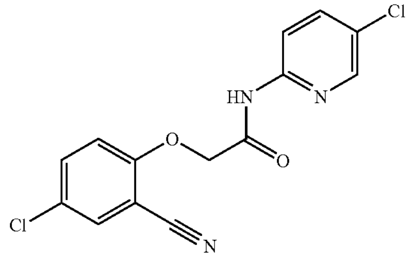 | APCI-MS M/Z:332/334 [M + H]$^+$ |
| 62 | 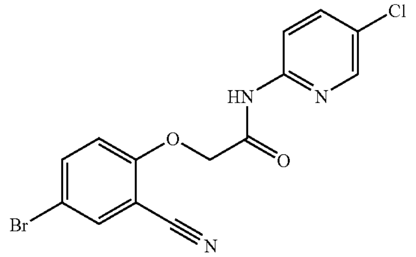 | APCI-MS M/Z:366/368 [M + H]$^+$ |
| 63 | 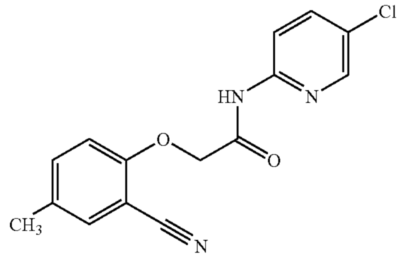 | APCI-MS M/Z:302/304 [M + H]$^+$ |
| 64 | 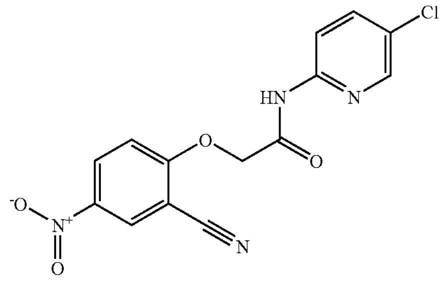 | APCI-MS M/Z:329/331 [M + H]$^+$ |

-continued
| Ref. Ex. No. | Structure | Physicochemical Properties |
| --- | --- | --- |
| 65 | 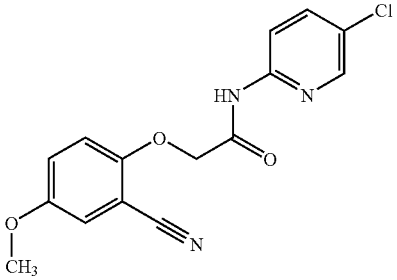 | APCI-MS M/Z:318/320 [M + H]$^+$ |
| 66 | 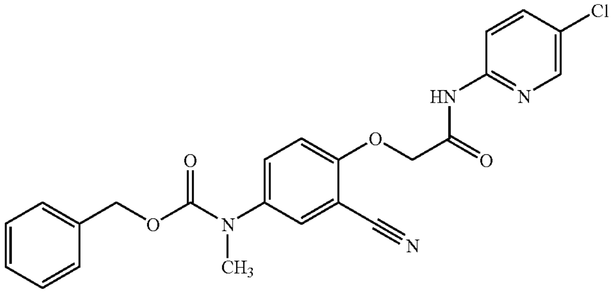 | APCI-MS M/Z:451/453 [M + H]$^+$ |
| 67 | 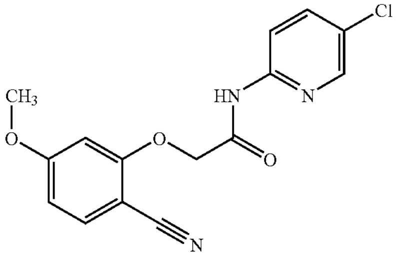 | APCI-MS M/Z:318/320 [M + H]$^+$ |
| 68 | 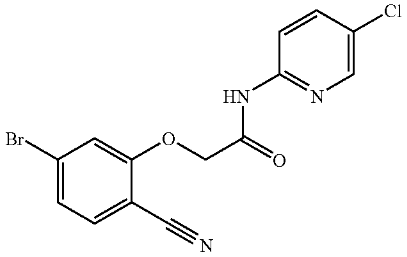 | APCI-MS M/Z:366/368 [M + H]$^+$ |
| 69 | 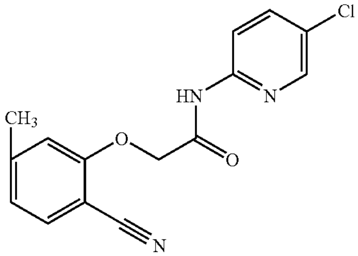 | APCI-MS M/Z:302/304 [M + H]$^+$ |

-continued

| Ref. Ex. No. | Structure | Physicochemical Properties |
|---|---|---|
| 70 | 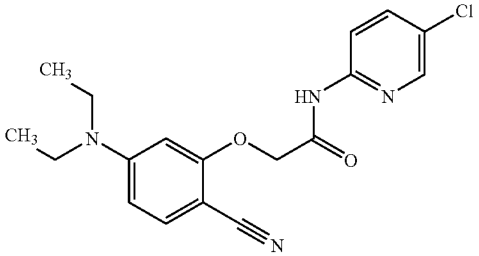 | APCI-MS M/Z:359/361 [M + H]$^+$ |
| 71 | 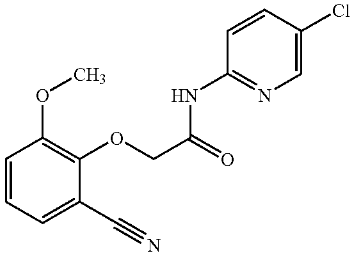 | APCI-MS M/Z:318/320 [M + H]$^+$ |
| 72 | 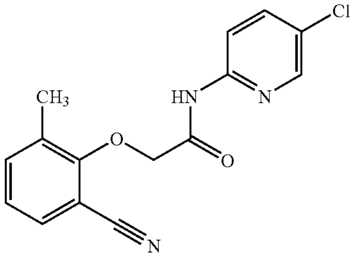 | APCI-MS M/Z:302/304 [M + H]$^+$ |

Reference Example 73

(2-Cyanophenoxy)-N-(4-chlorophenyl)-acetamide

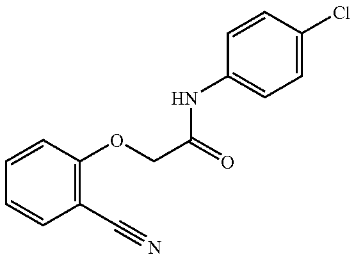

(2-Cyanophenoxy)acetic acid (30.00 g) obtained in Reference Example 43 is dissolved in N,N-dimethylformamide (300 ml), thereto are added successively 4-chloroaniline (25.9 g), 4-dimethylaminopyridine (22.7 g) and 1-ethyl-3-(3-dimethylaminopropyl)carbodiimide hydrochloride (35.6 g), and the mixture is stirred at room temperature for 3 hours. The reaction solution is concentrated under reduced pressure. The resulting residue is diluted with ethyl acetate-tetrahydrofuran, washed successively with water, 5% hydrochloric acid, water and saturated brine, dried over sodium sulfate and evaporated to remove the solvent. The resulting residue is suspended in diisopropyl ether, and the precipitates are collected by filtration to give the title compound (44.00 g). APCI-MS M/Z:287/289[M+H]$^+$ Reference Examples 74-77

The corresponding starting compounds are treated in a similar manner to Reference Example 73 to give the following compounds.

| Ref. Ex. No. | Structure | Physicochemical Properties |
|---|---|---|
| 74 | 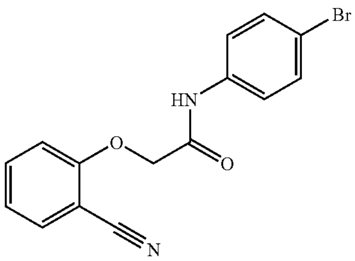 | APCI-MS M/Z:331/333 [M + H]$^+$ |
| 75 | 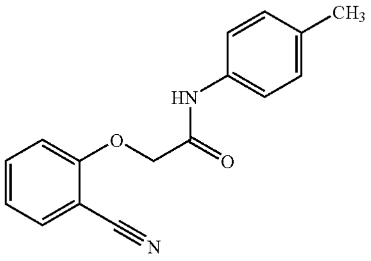 | APCI-MS M/Z:267 [M + H]$^+$ |
| 76 | 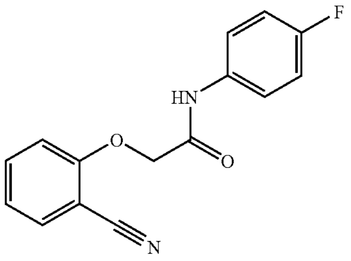 | APCI-MS M/Z:271 [M + H]$^+$ |
| 77 | 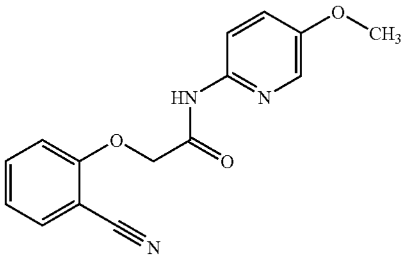 | APCI-MS M/Z:283 [M + H]$^+$ |

Reference Example 78

3-Amino-5-methoxycarbonyl-N-(5-chloropyridin-2-yl)benzofuran-2-carboxamide

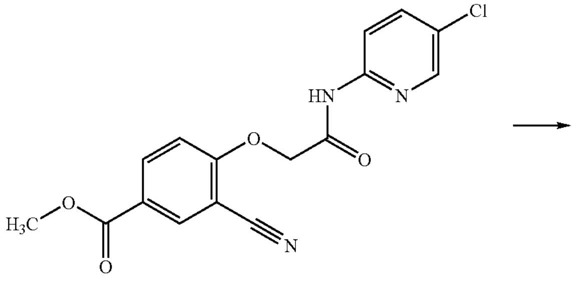

-continued

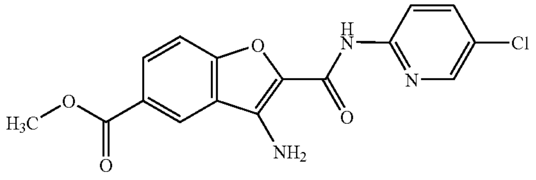

2-(4-Methoxycarbonyl-2-cyanophenoxy)-N-(5-chloropyridin-2-yl)acetamide (1.73 g) obtained in Reference Example 26 is dissolved in N,N-dimethylacetamide (15 ml), thereto is added sodium carbonate (160 mg), and the mixture is stirred at 100° C. for 2 hours. After allowing to cool, to the reaction solution is poured ice-water. The resulting precipitates are collected by filtration, washed successively with water, tetrahydrofuran and diethyl ether and dried to give the title compound (1.20 g).

APCI-MS M/Z:346/348[M+H]$^+$

Reference Example 79

3-Amino-5-methoxycarbonylmethyl-N-(5-chloropyridin-2-yl)benzofuran-2-carboxamide

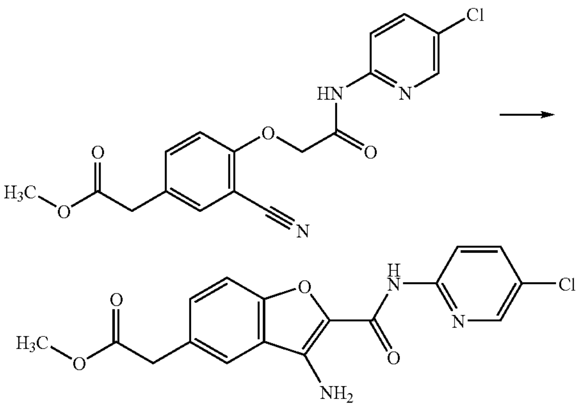

2-[2-Cyano-4-(methoxycarbonylmethyl)phenoxy]-N-(5-chloropyridin-2-yl)acetamide (500 mg) obtained in Reference Example 27 is dissolved in N,N-dimethylacetamide (15 ml), thereto is added sodium carbonate (74 mg), and the mixture is stirred at 100° C. for 16 hours. After allowing to cool, to the reaction solution is poured ice-water and extracted with ethyl acetate. The organic layer is washed successively with water and saturated brine, dried over sodium sulfate and evaporated to remove the solvent. The resulting residue is purified by silica gel column chromatography (eluent: n-hexane/ethyl acetate/chloroform=3/1/1), suspended in diethyl ether-n-hexane, and then the precipitates are collected by filtration to give title compound (180 mg). APCI-MS M/Z:360/362[M+H]$^+$ Reference Example 80

3-Amino-N-(5-chloropyridin-2-yl)-benzofuran-2-carboxamide

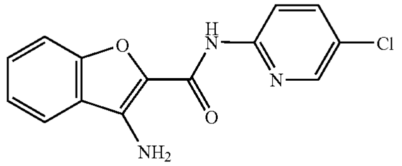

(2-Cyanophenoxy)-N-(5-chloropyridin-2-yl)acetamide (150.00 g) obtained in Reference Example 57 is dissolved in N,N-dimethylacetamide (1500 ml), thereto is added sodium carbonate (60.8 g) and the mixture is stirred at 70° C. for 7 hours. After allowing to cool, the reaction solution is poured to ice-water. The resulting precipitates are collected by filtration and washed with water several times. The precipitates are dissolved in ethyl acetate, washed with water and saturated brine, and dried over sodium sulfate. The organic layer is treated with activated charcoal. The insoluble materials are filtered, and the filtrate is concentrated under reduced pressure. The resulting residue is suspended in diethyl ether-ethyl acetate. The precipitates are collected by filtration, washed with diethyl ether, and dried to give the title compound (119.33 g). APCI-MS M/Z: 288/290[M+H]$^+$ Reference Examples 81-102

The corresponding starting compounds are treated in a similar manner to Reference Example 78, 79 or 80 to give the following compounds.

| Ref. Ex. No. | Structure | Physicochemical Properties |
|---|---|---|
| 81 | 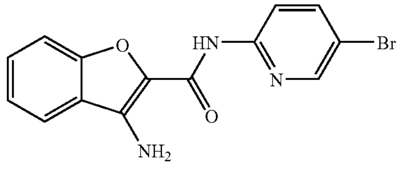 | APCI-MS M/Z: 332/334 [M + H]$^+$ |
| 82 | 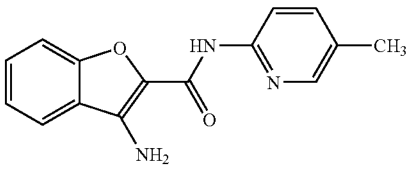 | APCI-MS M/Z: 268 [M + H]$^+$ |
| 83 | 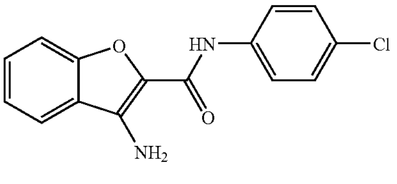 | APCI-MS M/Z: 287/289 [M + H]$^+$ |

-continued
| Ref. Ex. No. | Structure | Physicochemical Properties |
|---|---|---|
| 84 | 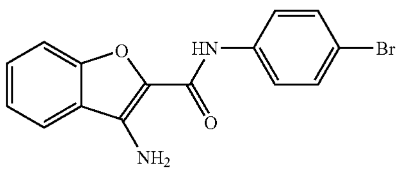 | APCI-MS M/Z: 331/333 [M + H]+ |
| 85 | 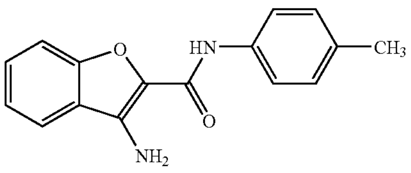 | APCI-MS M/Z: 267 [M + H]+ |
| 86 | 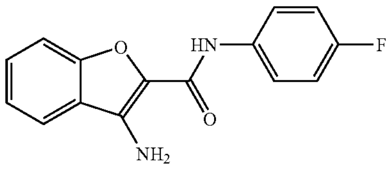 | APCI-MS M/Z: 271 [M + H]+ |
| 87 | 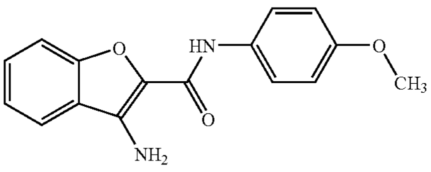 | APCI-MS M/Z: 283 [M + H]+ |
| 88 | 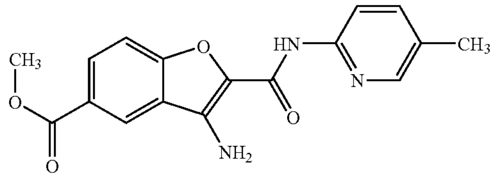 | APCI-MS M/Z: 326 [M + H]+ |
| 89 | 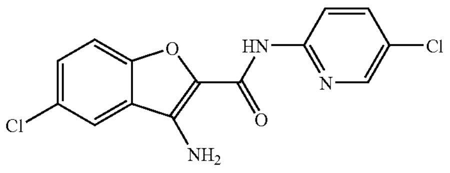 | APCI-MS M/Z: 322/324 [M + H]+ |
| 90 | 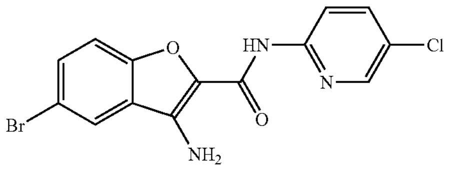 | APCI-MS M/Z: 366/368 [M + H]+ |
| 91 | 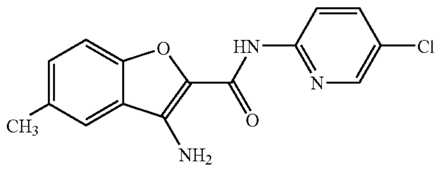 | APCI-MS M/Z: 302/304 [M + H]+ |

-continued
| Ref. Ex. No. | Structure | Physicochemical Properties |
|---|---|---|
| 92 | 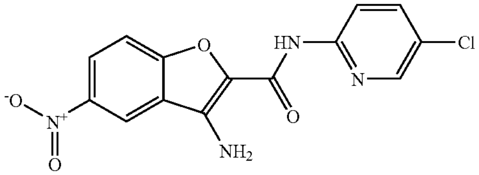 | APCI-MS M/Z: 333/335 [M + H]$^+$ |
| 93 | 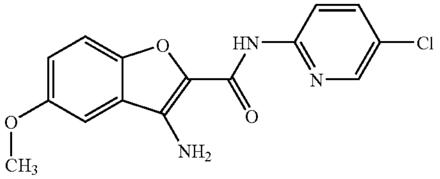 | APCI-MS M/Z: 318/320 [M + H]$^+$ |
| 94 | 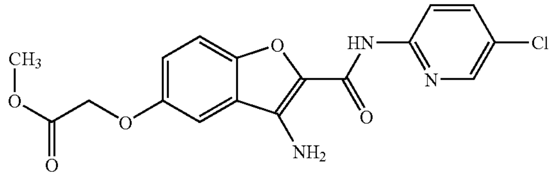 | APCI-MS M/Z: 376/378 [M + H]$^+$ |
| 95 | 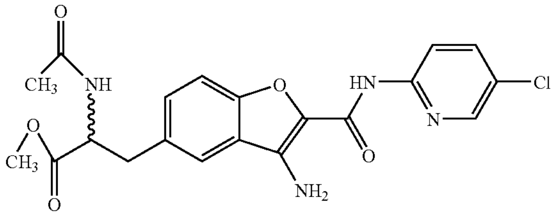 | APCI-MS M/Z: 431/433 [M + H]$^+$ |
| 96 | 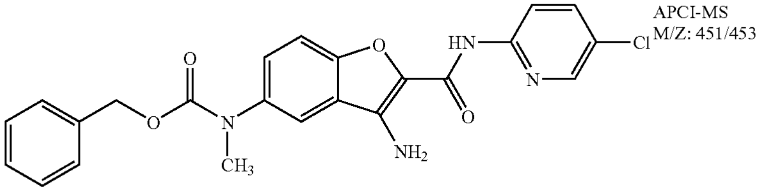 | APCI-MS M/Z: 451/453 [M + H]$^+$ |
| 97 | 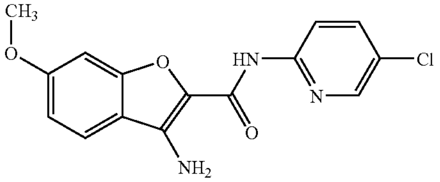 | APCI-MS M/Z: 318/320 [M + H]$^+$ |
| 98 | 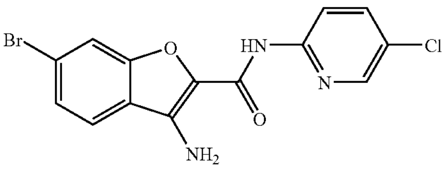 | APCI-MS M/Z: 366/368 [M + H]$^+$ |
| 99 | 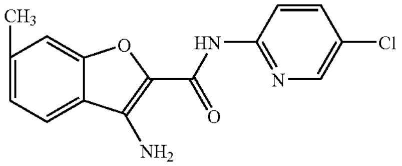 | APCI-MS M/Z: 302/304 [M + H]$^+$ |

-continued

| Ref. Ex. No. | Structure | Physicochemical Properties |
|---|---|---|
| 100 | 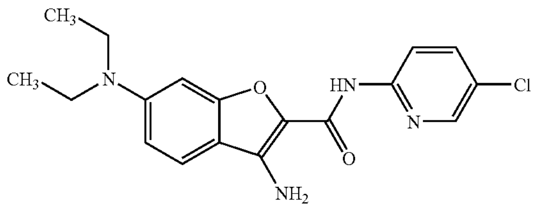 | APCI-MS M/Z: 359/361 $[M+H]^+$ |
| 101 | 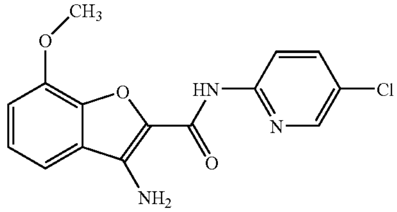 | APCI-MS M/Z: 318/320 $[M+H]^+$ |
| 102 | 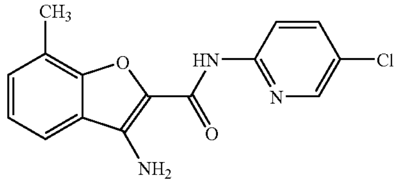 | APCI-MS M/Z: 302/304 $[M+H]^+$ |

Reference Example 103

(2-Cyano-4-hydroxyphenoxy)-N-(5-chloropyridin-2-yl)acetamide

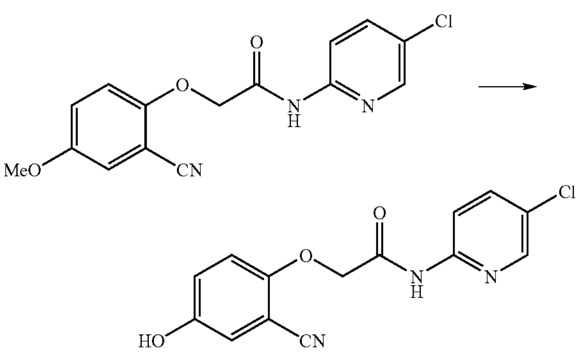

To a suspension of (2-cyano-4-methoxyphenoxy)-N-(5-chloropyridin-2-yl)acetamide (40.0 g) obtained in Reference Example 65 in dichloromethane (2000 ml) is added dropwise boron tribromide (173 g) at −58° C. over 40 minutes. The reaction solution is stirred for 26 hours while keeping the internal temperature between −20° C. and 0° C., and then poured to ice-water. The precipitated solids are collected by filtration, washed with water, and dried under reduced pressure. A portion (24.3 g) of the resulting solids (37.2 g) are purified by silica gel column chromatography (eluent: chloroform/methanol=50/1-10/1) to give the title compound (17.0 g). APCI-MS M/Z:304/306$[M+H]^+$ Reference Example 104

3-Amino-5-hydroxy-N-(5-chloropyridin-2-yl)benzofuran-2-carboxamide

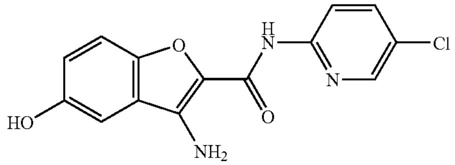

(2-Cyano-4-hydroxyphenoxy)-N-(5-chloropyridin-2-yl)acetamide (321 mg) obtained in Reference Example 103 is treated in a similar manner to Reference Example 79 to give the title compound (274 mg). APCI-MS M/Z:304/306$[M+H]^+$ Reference Example 105

(4-t-Buthoxycarbonylmethoxy-2-cyanophenoxy)-N-(5-chloropyridin-2-yl)acetamide

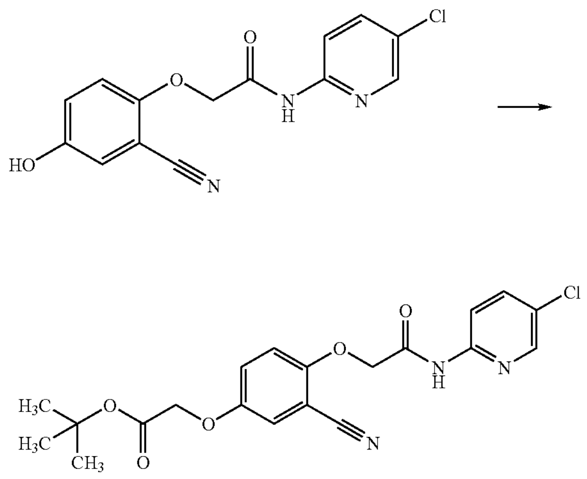

(2-Cyano-4-hydroxyphenoxy)-N-(5-chloropyridin-2-yl) acetamide (5.75 g) obtained in Reference Example 103 is dissolved in acetone (160 ml), and thereto are added cesium carbonate (8.08 g), t-butyl bromoacetate (4.58 g) and sodium iodide (3.64 g). After the reaction solution is heated under reflux for 8 hours, cesium carbonate (1.89 g), t-butyl bromoacetate (840 μl) and sodium iodide (875 mg) are further added, and the mixture is heated under reflux for additional 14 hours. The reaction solution is allowed to cool, poured to an ice-water, adjusted the pH to 1-2 with 10% hydrochloric acid, and then extracted with ethyl acetate. The organic layer is dried over sodium sulfate and evaporated to remove the solvent. The resulting residue is purified by silica gel column chromatography (eluent: hexane/ethyl acetate=3/1, 2/1, and then 1/1) and thereafter by NH-silica gel column chromatography (eluent: hexane/ethyl acetate=2/1, then 1/1) to give the title compound (4.02 g). APCI-MS M/Z:418/420[M+H]$^+$ Reference Example 106

3-Amino-5-t-butoxycarbonylmethoxy-N-(5-chloropyridin-2-yl)benzofuran-2-carboxamide

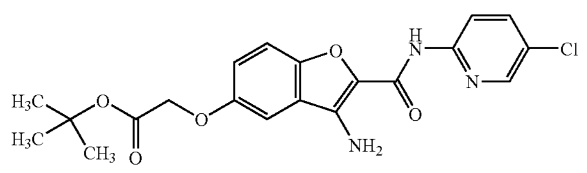

(4-t-Buthoxycarbonylmethoxy-2-cyanophenoxy)-N-(5-chloropyridin-2-yl)acetamide (8.18 g) obtained in Reference Example 105 is treated in a similar manner to Reference Example 79 to give the title compound (5.72 g)

APCI-MS M/Z:418/420[M+H]$^+$ .

Reference Example 107

3-Amino-5-(2-methoxyethoxy)-N-(5-chloropyridin-2-yl)benzofuran-2-carboxamide

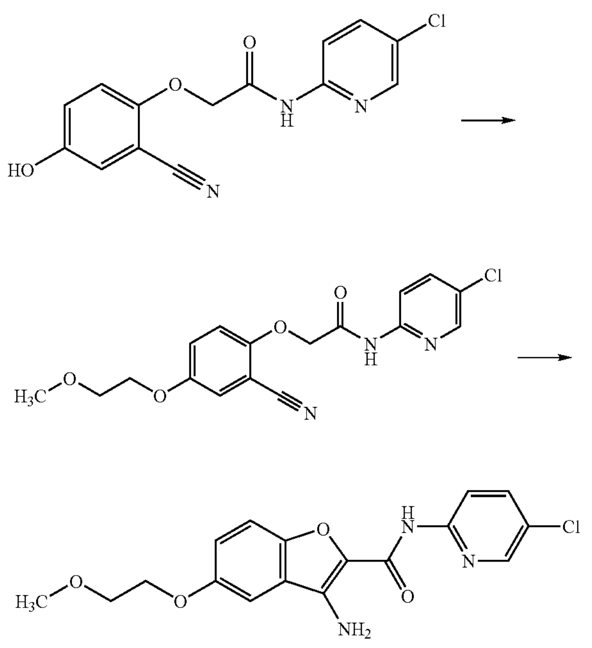

(1) (2-Cyano-4-hydroxyphenoxy)-N-(5-chloropyridin-2-yl)acetamide (100 mg) obtained in Reference Example 103 is dissolved in tetrahydrofuran, and thereto are added 2-methoxyethanol (9.30 ml) and triphenylphosphine (31.0 g) To the mixture is further added dropwise diethyl azodicarboxylate (22.2 ml) under ice-cooling. The reaction solution is warmed to room temperature, stirred for 17 hours and concentrated under reduced pressure. To the resulting residue is poured diisopropyl ether, and the insoluble materials are removed by filtration. The filtrate is concentrated under reduced pressure. The resulting residue is purified by silica gel column chromatography (eluent: chloroform/ethyl acetate=10/1) to give, as a crude material, [4-(2-methoxyethoxy)-2-cyanophenoxy]-N-(5-chloropyridin-2-yl)acetamide (71.48 g), which is used in the next step without further purification.

APCI-MS M/Z:362/364[M+H]$^+$ (2) The -crude material (71.48 g) containing [4-(2-methoxyethoxy)-2-cyanophenoxy]-N-(5-chloropyridin-2-yl)acetamide obtained in (1) above is treated in a similar manner to Reference Example 78 to give the title compound (24.40 g). APCI-MS M/Z:362/364[M+H]$^+$ Reference Examples 108-112

(2-Cyano-4-hydroxyphenoxy)-N-(5-chloropyridin-2-yl) acetamide obtained in Reference Example 103 and a corresponding alcohol are treated in a similar manner to Reference Example 101 to give the following compounds.

| Ref. Ex. No. | Structure | Physicochemical Properties |
|---|---|---|
| 108 | 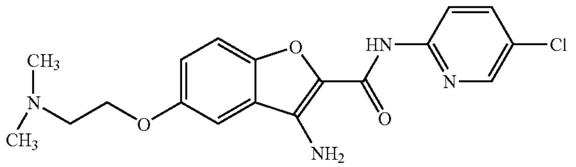 | APCI-MS M/Z: 375/377 [M + H]+ |
| 109 | 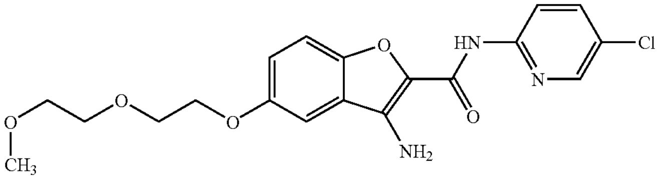 | APCI-MS M/Z: 406/408 [M + H]+ |
| 110 | 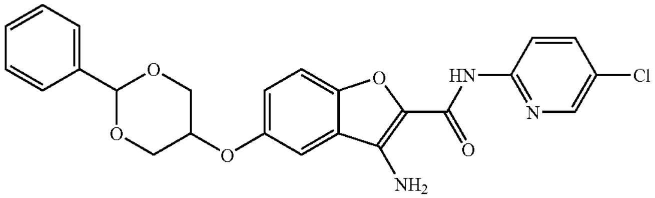 | APCI-MS M/Z: 466/468 [M + H]+ |
| 111 | 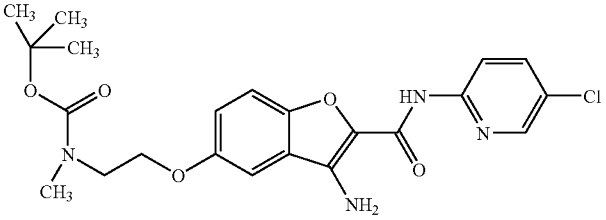 | APCI-MS M/Z: 461/463 [M + H]+ |
| 112 | 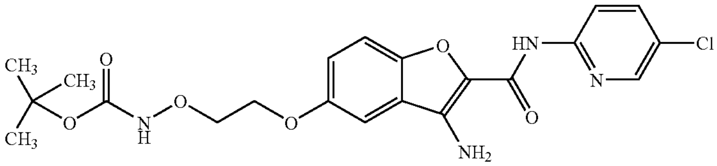 | APCI-MS M/Z: 463/465 [M + H]+ |

Reference Example 113

(2,4-Dicyanophenoxy)-N-(5-chloropyridin-2-yl)acetamide

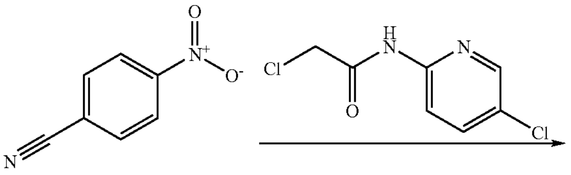

-continued

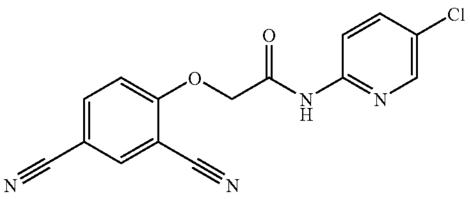

4-Nitrobenzonitrile (3.02 g) and potassium cyanide (2.02 g) are dissolved in dimethyl sulfoxide (100 ml), and the solution is stirred at 100° C. for an hour. The reaction solution is allowed to cool to room temperature, and thereto are added potassium carbonate (1.49 g), 2-chloro-N-(5-chloropyridin-2-yl)acetamide (10.42 g) obtained in Reference Example 26(1) and sodium iodide (8.76 g), and the mixture is stirred at 60° C. for 4.5 hours. The reaction solution is poured to water, and the precipitated solids are collected by filtration, washed with water and air-dried. The resulting solids are dissolved in ethyl acetate, and the solution is dried over sodium sulfate and evaporated to remove the solvent under reduced pressure. The resulting residue is purified by silica gel column chromatography (eluent: hexane/ethyl acetate=5/1 to 1/1), and the resulting residue is then suspended in ethyl acetate-diisopropyl ether. The precipitates are collected by filtration and dried to give the title compound (2.81 g).

APCI-MS M/Z:313/315[M+H]$^+$

Reference Example 114

3-Amino-5-cyano-N-(5-chloropyridin-2-yl)benzofuran-2-carboxamide

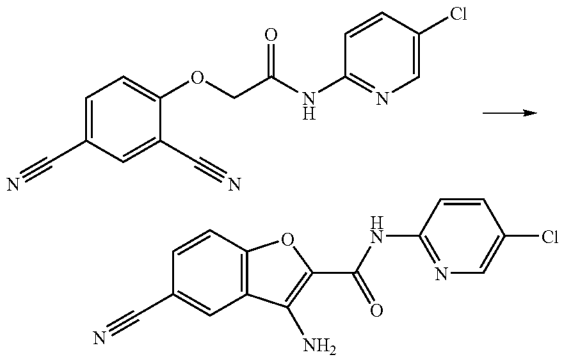

(2,4-Dicyanophenoxy)-N-(5-chloropyridin-2-yl)acetamide (1.02 g) obtained in Reference Example 113 is treated in a similar manner to Reference Example 79 to give the title compound (0.96 g). APCI-MS M/Z:313/315[M+H]$^+$ Reference Example 115

(3-Chloro-2-cyanophenoxy)-N-(5-chloropyridin-2-yl)acetamide

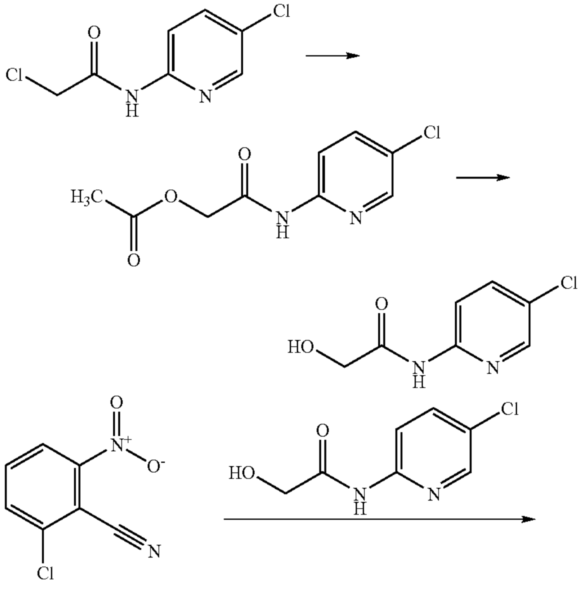

-continued

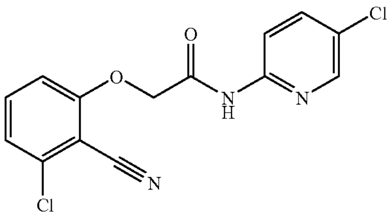

(1) 2-Chloro-N-(5-chloropyridin-2-yl)acetamide (30.68 g) obtained in Reference Example 26(1) is dissolved in N,N-dimethylformamide (500 ml), thereto is added sodium acetate (24.55 g), and the mixture is stirred at 60° C. for 5 hours. The reaction solution is diluted with ethyl acetate, washed successively with water and saturated brine. The solution is dried over magnesium sulfate, treated with activated charcoal, and the filtrate is concentrated under reduced pressure. The resulting residue is suspended in n-hexane and crystals are collected by filtration, washed with n-hexane, and dried to give N-(5-chloropyridin-2-yl)-2-acetoxyacetamide (30.58 g). APCI-MS M/Z:229/231[M+H]$^+$ (2) 2-Acetoxy-N-(5-chloropyridin-2-yl)acetamide (30.36 g) obtained in (l) above is suspended in methanol (1200 ml), and thereto is added potassium carbonate (22.0 g) under ice-cooling. The reaction solution is warmed to room temperature, stirred for 0.5 hours, and concentrated under reduced pressure. Ethyl acetate (1500 ml) and ice-water (1000 ml) are poured to the resulting residue, and the mixture is extracted with ethyl acetate. The organic layer is washed with saturated brine, dried over sodium sulfate, and evaporated to remove the solvent under reduced pressure. The resulting residue is suspended in a small amount of ethyl acetate, and thereto is added diisopropyl ether. The precipitated crystals are collected by filtration, washed with diisopropyl ether and dried to give 2-hydroxy-N-(5-chloropyridin-2-yl)acetamide (22.85 g).

APCI-MS M/Z:187/189[M+H]$^+$ (3) 2-Chloro-6-nitrobenzonitrile (187 mg) and 2-hydroxy-N-(5-chloropyridin-2-yl)acetamide (183 mg) obtained in (2) above are dissolved in N,N-dimethylformamide (2 ml). To the solution is added 60% oleaginous sodium hydride (80 mg) under ice-cooling. Under the same cooling conditions, the mixture is stirred for 6 hours, and thereto is poured a saturated aqueous ammonium chloride solution followed by extraction with ethyl acetate. The organic layer is washed with water and saturated brine, dried over sodium sulfate and evaporated to remove the solvent under reduced pressure. The resulting residue is suspended in n-hexane-diisopropyl ether, filtered, and dried to give the title compound (286 mg). APCI-MS M/Z:322/324[M+H]$^+$ Reference Example 116

3-Amino-4-chloro-N-(5-chloropyridin-2-yl)benzofuran-2-carboxamide

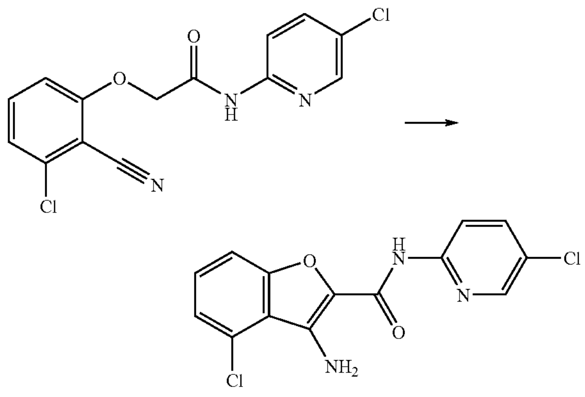

(3-Chloro-2-cyanophenoxy)-N-(5-chloropyridin-2-yl)acetamide (274 mg) obtained in Reference Example 115 is dissolved in N,N-dimethylacetamide (10 ml), thereto is added cesium carbonate (333 mg) and the mixture is stirred at 100° C. for 8 hours. The reaction solution is allowed to cool, and thereto is added ice-water. The precipitates are collected by filtration and washed with water. The resulting precipitates are dissolved in hot ethyl acetate, washed with saturated brine, and dried over sodium sulfate. To the organic layer are added activated charcoal and NH-silica gel (5 g), and the mixture is filtered to remove the insoluble materials. The filtrate is concentrated under reduced pressure. The resulting residue is suspended in ethyl acetate-diethyl ether and filtered to give the title compound (112 mg). APCI-MS M/Z:322/324 $[M+H]^+$ Reference Example 117

3-Amino-4-methoxy-N-(5-chloropyridin-2-yl)benzofuran-2-carboxamide

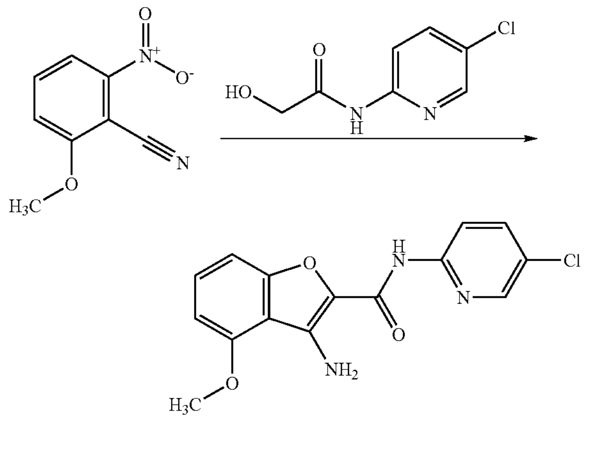

2-Methoxy-6-nitrobenzonitrile (589 mg) and 2-hydroxy-N-(5-chloropyridin-2-yl)acetamide (560 mg) obtained in Reference Example 115(2) are dissolved in N,N-dimethylacetamide (10 ml), and thereto is added potassium carbonate (810 mg). After stirring at 60° C. overnight, potassium carbonate (810 mg) is further added to the reaction solution and the mixture is stirred at 100° C. for 4 hours. The reaction solution is allowed to cool, and thereto is poured ice-water followed by extraction with ethyl acetate. The organic layer is washed with water and saturated brine, dried over sodium sulfate, and treated with activated charcoal. The insoluble materials are removed by filtration and washed with chloroform-methanol. The filtrate and washings are combined and concentrated under reduced pressure. The resulting residue is suspended in diisopropyl ether and filtered to give the title compound (104 mg). APCI-MS M/Z:317/319$[M+H]^+$ Reference Example 118

Methyl 2-formyl-3-hydroxybenzoate and methyl 4-formyl-3-hydroxybenzoate

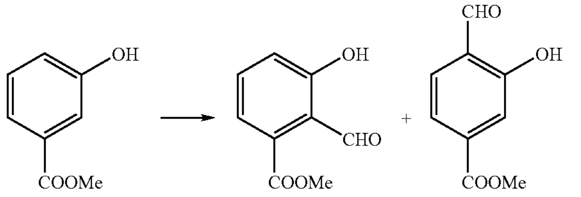

Methyl 3-hydroxybenzoate (75.5 g) is dissolved in trifluoroacetic acid (2 L), thereto is added hexamethylene-tetramine tetramine (141.4 g) at room temperature, and the mixture is heated under reflux for 3 hours. The reaction solution is concentrated under reduced pressure and water is added to the resulting residue. The mixture is adjusted to pH 8 with potassium carbonate and sodium hydrogen carbonate, diluted with water and extracted with ethyl acetate. The organic layer is washed with saturated brine, dried over sodium sulfate, and evaporated to remove the solvent under reduced pressure. The resulting residue is purified by silica gel column chromatography (eluent: hexane/ethyl acetate=8/1, 5/1, and then 2/1) to give methyl 2-formyl-3-hydroxybenzoate (54.6 g) (ESI-MS m/z: 179$[M-H]^-$) and methyl 4-formyl-3-hydroxybenzoate (4.4 g) (ESI-MS m/z: 179$[M-H]^-$).

Reference Example 119

Methyl 4-cyano-3-hydroxybenzoate

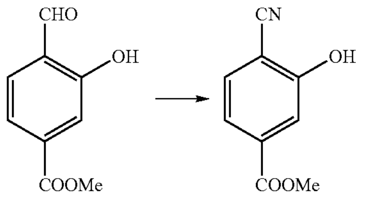

Methyl 4-formyl-3-hydroxybenzoate (1.96 g) obtained in Reference Example 118 is dissolved in formic acid (50 ml), thereto are added hydroxylammonium chloride (0.85 g) and sodium formate (0.85 g) and the mixture is heated under reflux for 14 hours. The reaction solution is concentrated under reduced pressure, diluted with water and extracted with ethyl acetate. The organic layer is washed with saturated brine, dried over sodium sulfate and evaporated to remove the solvent under reduced pressure. The resulting residue is suspended in chloroform/diisopropyl ether, and the precipitates are collected by filtration to give the title compound (0.66 g). Furthermore, the filtrate is concentrated under reduced pressure and the resulting residue is purified by silica gel column chromatography (eluent: hexane/ethyl acetate=3/2) to give the title compound (1.08 g). ESI-MS M/Z:176[M−H]$^-$ Reference Example 120

2-(2-Cyano-5-methoxycarbonyl-phenoxy)-N-(5-chloropyridin-2-yl)acetamide

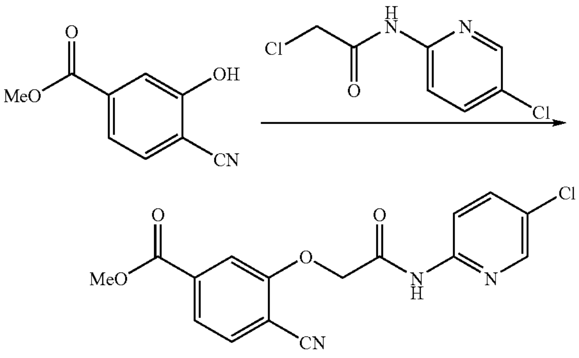

Methyl 4-cyano-3-hydroxybenzoate (655 mg) obtained in Reference Example 119 is dissolved in acetone (20 ml), and thereto are added 2-chloro-N-(5-chloropyridin-2-yl)acetamide (897 mg) obtained in Reference Example 26(1), potassium carbonate (773 mg) and sodium iodide (657 mg), followed by heating under reflux for 40 minutes. The reaction solution is concentrated under reduced pressure, thereto is added water and the mixture is extracted with ethyl acetate-tetrahydrofuran. The organic layer is washed with saturated brine, dried over sodium sulfate, and evaporated to remove the solvent under reduced pressure. The resulting residue is suspended in chloroform-diisopropyl ether and the precipitates are collected by filtration to give the title compound (1.16 g).

APCI-MS M/Z:346/348[M+H]$^+$

Reference Example 121

3-Amino-6-methoxycarbonyl-N-(5-chloropyridin-2-yl)benzofuran-2-carboxamide

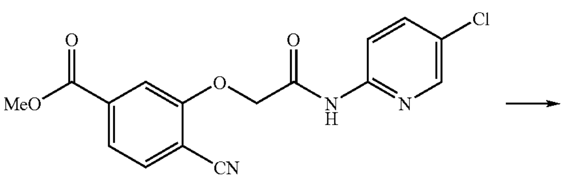

-continued

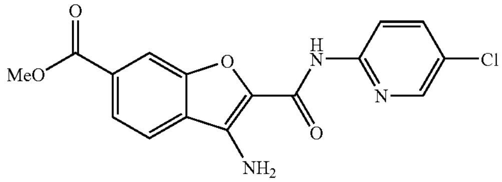

2-(2-Cyano-5-methoxycarbonylphenoxy)-N-(5-chloropyridin-2-yl)acetamide (1.03 g) obtained in Reference Example 120 is dissolved in N,N-dimethylacetamide (10 ml), thereto is added sodium carbonate (97 mg) and the mixture is stirred at 100° C. for 4 hours. The reaction solution is poured to water (50 ml). The precipitates are collected by filtration, washed with water and ethanol and dried to give the title compound (839 mg). APCI-MS M/Z:346/348[M+H]$^+$ Reference Example 122

Methyl 2-cyano-3-hydroxybenzoate

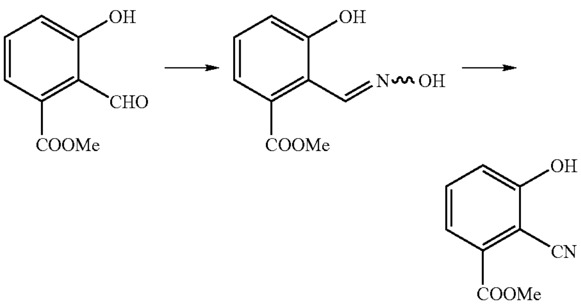

(1) Methyl 2-formyl-3-hydroxybenzoate (9.23 g) obtained in Reference Example 118 is suspended in methanol (150 ml), and thereto are added an aqueous solution (15 ml) of hydroxylammonium chloride (3.56 g) and an aqueous solution (15 ml) of sodium acetate (4.36 g) under ice-cooling. The mixture is warmed to room temperature, stirred for 2 hours, and evaporated to remove methanol. The resulting residue is diluted with water and extracted with chloroform. The organic layer is dried over sodium sulfate and evaporated to remove the solvent under reduced pressure to give methyl 2-hydroxyiminomethyl-3-hydroxybenzoate (9.89 g). APCI-MS M/Z:196[M+H]$^+$ (2) Methyl 2-hydroxyiminomethyl-3-hydroxybenzoate (10.57 g) obtained in (1) above is suspended in chloroform (100 ml), and thereto is added triethylamine (19.35 g) under ice-cooling. At the same temperature, trifluoroacetic anhydride (25.40 g) is added dropwise to the resulting solution over 30 minutes. The reaction solution is stirred at room temperature for 3 days, and thereto is added an aqueous saturated sodium hydrogen carbonate solution followed by extraction with chloroform. The organic layer is dried over magnesium sulfate and evaporated to remove the solvent under reduced pressure. The resulting residue is dissolved in methanol (150 ml), thereto is added potassium carbonate (15.6 g), and the mixture is stirred at room temperature for 50 minutes. The reaction solution is diluted with water, acidified with conc. hydrochloric acid, and then extracted with chloroform. The organic layer is dried over magnesium sulfate and then evaporated to remove the solvent, and the resulting residue is suspended in ethyl acetate-diisopropyl ether. The precipitates are collected by filtration to give the title compound (8.71 g).

ESI-MS M/Z:176[M−H]$^-$

Reference Example 123

2-(2-Cyano-3-methoxycarbonyl-phenoxy)-N-(5-chloropyridin-2-yl)acetamide

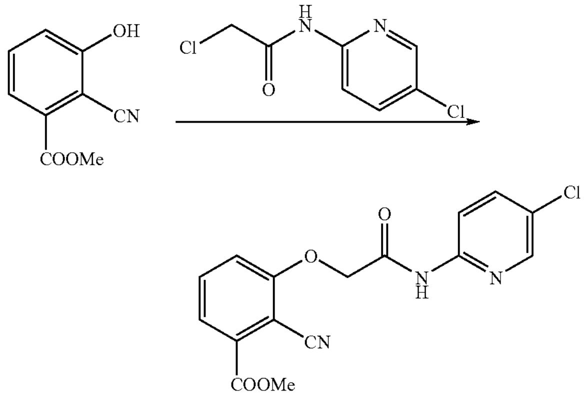

Methyl 2-cyano-3-hydroxybenzoate (1.70 g) obtained in Reference Example 122 is treated in a similar manner to Reference Example 120 to give the title compound (2.69 g).

APCI-MS M/Z:346/348[M+H]$^+$

Reference Example 124

3-Amino-4-methoxycarbonyl-N-(5-chloropyridin-2-yl)benzofuran-2-carboxamide

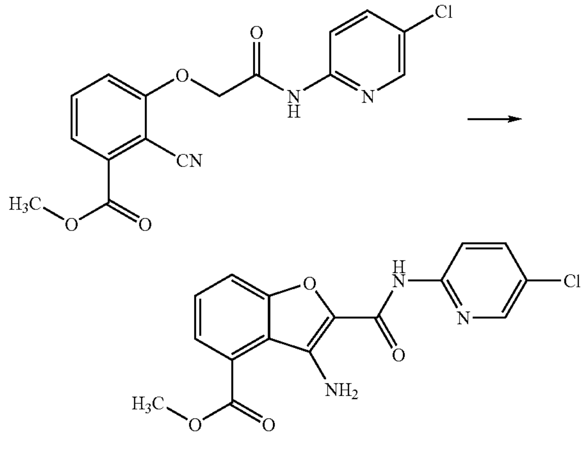

2-(2-Cyano-3-methoxycarbonylphenoxy)-N-(5-chloropyridin-2-yl)acetamide (1.51 g) obtained in Reference Example 123 is treated in a similar manner to Reference Example 121 to give the title compound (335 mg).

APCI-MS M/Z:346/348[M+H]$^+$

Reference Example 125

3-Amino-5-carboxy-N-(5-chloropyridin-2-yl)benzofuran-2-carboxamide

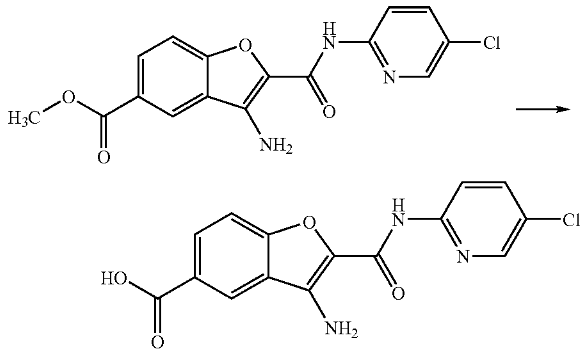

3-Amino-5-methoxycarbonyl-N-(5-chloropyridin-2-yl) benzofuran-2-carboxamide (2.01 g) obtained in Reference Example 78 is suspended in tetrahydrofuran (20 ml)-methanol, thereto is added 4 N aqueous sodium hydroxide solution (5 ml) under ice-cooling, and the reaction solution is stirred at room temperature for 13 hours. The reaction solution is concentrated under reduced pressure. The resulting residue is diluted with water, and the mixture is adjusted to around pH 3. by pouring 10% hydrochloric acid under ice-cooling. The precipitates are collected by filtration, washed successively with water and ethanol, and dried to give the title compound (1.87 g). ESI-MS M/Z:330[M−H]$^-$ Reference Examples 126-127

The ester obtained in Reference Example 121 or 124 is treated in a similar manner to Reference Example 125 to give the following compounds.

| Ref. Ex. No. | Structure | Physico-chemical Properties |
|---|---|---|
| 126 | 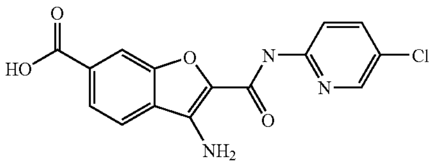 | ESI-MS M/Z: 330/332 [M − H]$^-$ |
| 127 | 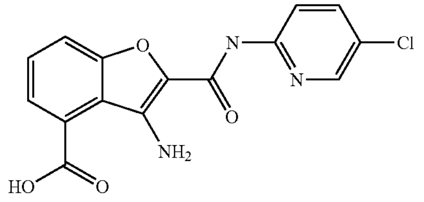 | ESI-MS M/Z: 330/332 [M − H]$^-$ |

Reference Example 128

3-Amino-5-dimethylaminocarbonyl-N-(5-chloropyridin-2-yl)benzofuran-2-carboxamide

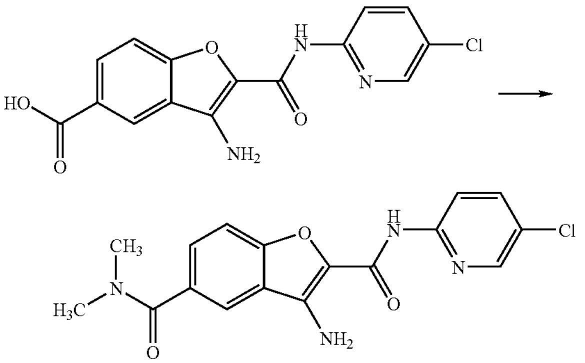

3-Amino-5-carboxy-N-(5-chloropyridin-2-yl)-benzofuran-2-carboxamide (1.51 g) obtained in Reference Example 125 is suspended in pyridine (15 ml), thereto are added successively dimethylamine hydrochloride (0.77 g), 1-hydroxybenzotriazole (1.37 g) and 1-ethyl-3-(3-dimethylaminopropyl)carbodiimide hydrochloride (1.79 g) under ice-cooling, and the mixture is stirred at room temperature for 14 hours. The reaction solution is diluted with water (100 ml) and thereto is added a saturated aqueous sodium hydrogen carbonate solution to adjust to pH 8-9. The precipitates are collected by filtration, washed successively with water and ethanol, and dried to give the title compound (1.50 g). APCI-MS M/Z:359/361[M+H]$^+$ Reference Examples 129-130

The carboxylic acid obtained in Reference Example 126 or 127 is treated in a similar manner to Reference Example 128 to give the following compounds.

| Ref. Ex. No. | Structure | Physico-chemical Properties |
|---|---|---|
| 129 | 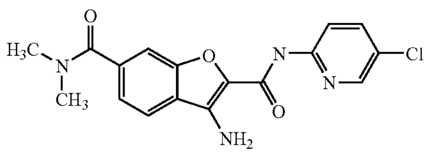 | APCI-MS M/Z: 359/361 [M + H]$^+$ |
| 130 | 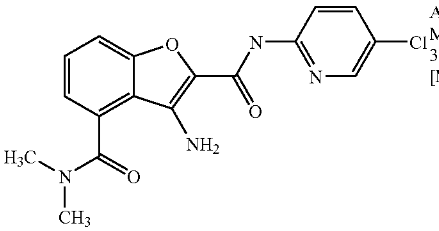 | APCI-MS M/Z: 359/361 [M + H]$^+$ |

Reference Example 131 t-Butyl [2-cyano-4-(methoxy-carbonylmethyl)phenoxy]acetate

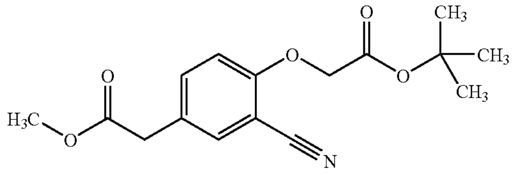

Methyl (3-cyano-4-hydroxyphenyl)acetate (9.56 g) obtained in Reference Example 12 and t-butyl bromoacetate (11.7 g) are treated in a similar manner to Reference Example 30 to give the title compound (15.18 g).

APCI-MS M/Z:323[M+NH$_4$]$^+$

Reference Example 132

[2-Cyano-4-(methoxycarbonylmethyl)-phenoxy]acetic acid

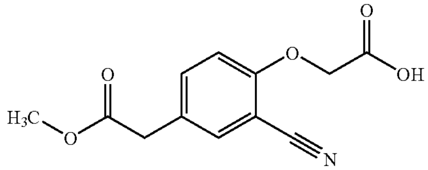

t-Butyl [2-cyano-4-(methoxycarbonylmethyl)phenoxy]-acetate (15.15 g) obtained in Reference Example 131 is treated in a similar manner to Reference Example 43 to give the title compound (11.78 g). ESI-MS M/Z:248[M−H]$^-$ Reference Example 133

2-[2-Cyano-4-(methoxycarbonyl-methyl)phenoxy]-N-(5-methylpyridin-2-yl)acetamide

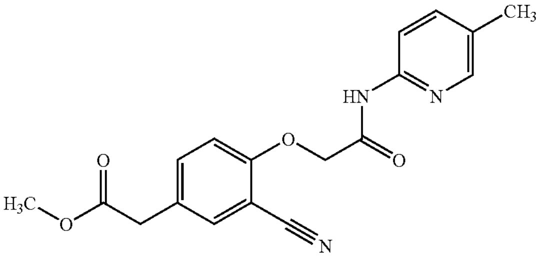

[2-Cyano-4-(methoxycarbonylmethyl)phenoxy]acetic acid (5.00 g) obtained in Reference Example 132 and 2-amino-5-methylpyridine (2.60 g) are treated in a similar manner to Reference Example 57 to give the title compound (5.17 g).

APCI-MS M/Z:340[M+H]$^+$

Reference Example 134

3-Amino-5-methoxycarbonylmethyl-N-(5-methylpyridin-2-yl)benzofuran-2-carboxamide

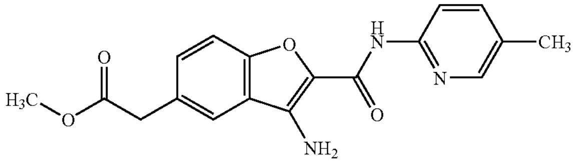

2-[2-Cyano-4-(methoxycarbonylmethyl)phenoxy]-N-(5-methylpyridin-2-yl)acetamide (4.10 g) obtained in Reference Example 133 is suspended in t-butanol (80 ml). To the mixture is added potassium t-butoxide (136 mg), and the reaction solution is heated under reflux for one hour. To the reaction solution is poured ice-water, and the precipitates are collected by filtration, washed with water, and dried to give the title compound (3.77 g).

APCI-MS M/Z:340[M+H]$^+$

INDUSTRIAL APPLICABILITY

The present compound [1] or a pharmaceutically acceptable salt thereof is less toxic and safe, and has an excellent inhibitory effect on FXa, and therefore is useful as a medicament for prevention and treatment of diseases caused by thrombi and emboli.

The invention claimed is:

1. A carbamoyl-type benzofuran derivative of the formula [1]:

[1]

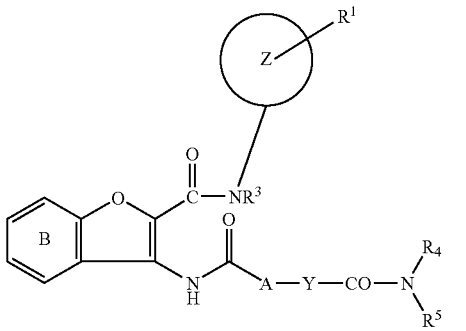

wherein Ring Z is a group of the formula:

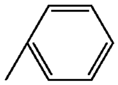 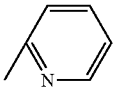 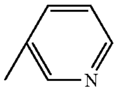 or 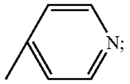;

A is a single bond or a group of the formula: —NH—;

Y is a lower alkylene group, a cycloalkanediyl group, a phenyl group or a saturated heterocyclic group;

$R^4$ and $R^5$ are the same or different and each is a hydrogen atom, an optionally substituted lower alkyl group or an optionally substituted saturated heterocyclic group, or $R^4$ and $R^5$ combine together at the ends to form an optionally substituted nitrogen-containing saturated heterocyclic group along with the adjacent nitrogen atom;

$R^1$ is a hydrogen atom, a halogen atom, a lower alkyl group, a lower alkoxy group, a cyano group, or an amino group optionally substituted by 1 to 2 lower alkyl groups;

Ring B of the formula:

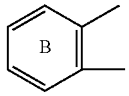

is an optionally substituted benzene ring; and $R^3$ is a hydrogen atom or a lower alkyl group, or a pharmaceutically acceptable salt thereof.

2. The compound according to claim 1, wherein Ring Z is a group of the formula:

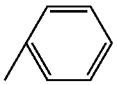 or 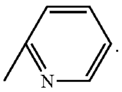.

3. The compound according to claim 2, wherein the "optionally substituted lower alkyl group" for $R^4$ or $R^5$ is an unsubstituted lower alkyl group, a lower alkyl group substituted by an amino group optionally substituted by 1 to 2 lower alkyl groups, a lower alkyl group substituted by a hydroxyl group, a lower alkyl group substituted by a lower alkoxy group or a lower alkyl group substituted by a pyridyl group;

the "optionally substituted saturated heterocyclic group" for $R^4$ or $R^5$ is tetrahydropyranyl;

the "optionally substituted nitrogen-containing saturated heterocyclic group" formed from $R^4$, $R^5$ and the adjacent nitrogen atom, when $R^4$ and $R^5$ combine together at the ends, is a pyrrolidinyl group, a morpholinyl group, a pyrrolidinyl group substituted by a hydroxy-lower alkyl group, a pyrrolidinyl group substituted by a hydroxyl group, a thiomorpholinyl group, a piperidyl group, a piperidyl group substituted by a hydroxyl group, a piperazinyl group substituted by a hydroxy-lower alkyl group, a piperidyl group substituted by a hydroxy-lower alkyl group, a piperazinyl group substituted by a lower alkyl group, a pyrrolidinyl group substituted by a lower alkoxycarbonylamino group, a piperidyl group substituted by an amino group optionally substituted by 1 to 2 lower alkyl groups, an oxopyrrolidinyl group, an oxomorpholinyl group, an oxothiomorpholinyl group, an oxopiperidyl group, an oxopiperazinyl group, or a piperidyl group substituted by a lower alkoxycarbonyl group; and the "saturated heterocyclic group" for Y is a piperidyl group.

4. The compound according to claim 3, wherein Ring B is a benzene ring optionally substituted by one or two groups selected independently from a halogen atom, an optionally substituted lower alkyl group, a hydroxy group, an optionally substituted lower alkoxy group, an oxy group substituted by an optionally substituted saturated heterocyclic group, a substituted carbonyl group, an optionally substituted amino group, a nitro group, a cyano group, a 4,5-dihydroxazolyl group and a group of the formula:

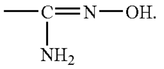

5. The compound according to claim 4, wherein the "optionally substituted lower alkyl group" as a substituent for Ring B is a lower alkyl group optionally substituted by a group selected from the following:

(1) a lower alkoxycarbonyl group,
(2) a carboxyl group,
(3) a carbamoyl group optionally substituted by 1 to 2 groups selected from (a) a lower alkyl group, (b) a lower alkoxy-lower alkyl group, (c) a hydroxy-lower alkyl group, (d) an aminoalkyl group optionally substituted by 1 to 2 lower alkyl groups, and (e) a lower alkoxy group,
(4) a carbonyl group substituted by a morpholinyl group,
(5) a piperidylcarbonyl group substituted by a hydroxy-lower alkyl group,
(6) a pyrrolidinylcarbonyl group substituted by a hydroxy-lower alkyl group,
(7) a carbonyl group substituted by a hydroxyl group-substituted piperidyl group,
(8) a hydroxyl group, and
(9) a pyrrolidinylcarbonyl group;

the "optionally substituted lower alkoxy group" as a substituent for Ring B is a lower alkoxy group optionally substituted by a group selected from the following:

(1) a carboxyl group,
(2) a lower alkoxycarbonyl group,
(3) a lower alkoxy group,
(4) a hydroxyl group,
(5) an aminooxy group optionally substituted by 1 to 2 lower alkoxycarbonyl groups,
(6) a lower alkoxy group substituted by a lower alkoxy group,
(7) a carbonyl group substituted by a group selected from morpholinyl group, a piperidyl group or a pyrrolidinyl group,
(8) a carbonyl group substituted by a hydroxypiperidyl group,
(9) a piperidylcarbonyl group substituted by a hydroxy-lower alkyl group,
(10) a pyrrolidinylcarbonyl group substituted by a hydroxy-lower alkyl group,
(11) a carbonyl group substituted by a lower alkyl-piperazinyl group,
(12) an amino group optionally substituted by 1 to 2 groups selected from (a) a lower alkyl group, (b) a lower alkoxy-carbonyl group, and (c) a lower alkanoyl group,
(13) a carbamoyl group optionally substituted by 1 to 2 groups selected from (a) a lower alkyl group, (b) a lower alkoxy-lower alkyl group, (c) a hydroxy-lower alkyl group, and (d) a lower alkyl group substituted by an amino group optionally substituted by 1 to 2 lower alkyl groups; and
(14) a group of the formula:

$—O—NH—C(=NH)NH_2$;

the "oxy group substituted by an optionally substituted saturated heterocyclic group" as a substituent for Ring B is an oxy group substituted by a saturated heterocyclic group optionally substituted by an aromatic hydrocarbon group;

the "substituted carbonyl group" as a substituent for Ring B is a carbonyl group substituted by a group selected from the following:

(1) a lower alkoxy group,
(2) a hydroxyl group,
(3) an amino group optionally substituted by 1 to 2 groups selected from (a) a lower alkyl group, (b) a lower alkoxy group, (c) a lower alkoxy-lower alkyl group, (d) a hydroxy-lower alkyl group, (e) a lower alkyl group substituted by an amino group optionally substituted by 1 to 2 lower alkyl groups, (f) a lower alkyl group substituted by an aromatic hydrocarbon group, and (g) a lower alkyl group substituted by a pyridyl group,
(4) a morpholinyl group, a pyrrolidinyl group, a piperidyl group or a thiomorpholinyl group,
(5) a hydroxypiperidyl group,
(6) a piperidyl group substituted by a hydroxy-lower alkyl group,
(7) a pyrrolidinyl group substituted by a hydroxy-lower alkyl group, and
(8) a lower alkyl-piperazinyl group;

the "optionally substituted amino group" as a substituent for Ring B is an amino group optionally substituted by 1 to 2 groups selected from the following:

(1) a lower alkyl group,
(2) a lower alkoxy-lower alkyl group,
(3) a hydroxy-lower alkyl group,
(4) a lower alkanoyl group,
(5) a lower alkoxy-lower alkanoyl group,
(6) a hydroxy-lower alkanoyl group,
(7) a lower alkanoyl group substituted by a lower alkanoyloxy group,
(8) a lower alkanoyl group substituted by an amino group optionally substituted by 1 to 2 groups selected from (a) a lower alkyl group and (b) a lower alkanoyl group,
(9) a lower alkoxycarbonyl group,
(10) a lower alkoxycarbonyl group substituted by an aromatic hydrocarbon group,
(11) a carbamoyl group substituted by 1 to 2 lower alkyl groups,
(12) a lower alkylsulfonyl group, and
(13) a lower alkylsulfonyl group substituted by a morpholinyl group.

6. The compound according to claim 5, wherein Ring B is an unsubstituted benzene ring.

7. The compound according to claim 5, wherein Ring Z is a group of the formula:

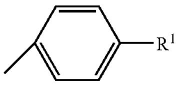 or 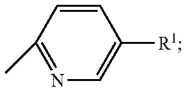

the formula:

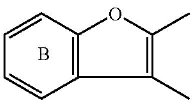 is 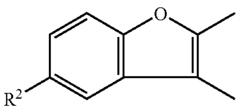 or

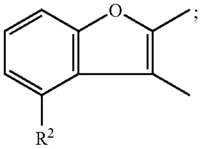

$R^1$ is a halogen atom or a lower alkyl group;

$R^2$ is a group selected from the following:

A) a hydrogen atom, a cyano group, an amino group optionally substituted by 1 to 2 lower alkyl groups, a hydroxy group;

B) a lower alkyl group optionally substituted by a group selected from the following:

(1) a lower alkoxycarbonyl group, (2) a carboxyl group, (3) a carbamoyl group optionally substituted by 1 to 2 groups selected from (a) a lower alkyl group, (b) a lower alkoxy-lower alkyl group, (c) a lower alkyl group substituted by a hydroxyl group, (d) a lower alkyl group substituted by an amino group optionally substituted by 1 to 2 lower alkyl groups, and (e) a lower alkoxy group, (4) a carbonyl group substituted by a morpholinyl group, (5) a piperidylcarbonyl group substituted by a hydroxy-lower alkyl group, (6) a pyrrolidinylcarbonyl group substituted by a hydroxy-lower alkyl group, (7) a carbonyl group substituted by a hydroxyl group-substituted piperidyl group, (8) a hydroxyl group; and (9) a pyrrolidinylcarbonyl group;

C) a lower alkoxy group optionally substituted by a group selected from the following:

(1) a carboxyl group, (2) a lower alkoxycarbonyl group, (3) a lower alkoxy group, (4) a hydroxyl group, (5) an aminooxy group optionally substituted by 1 to 2 lower alkoxycarbonyl groups, (6) a lower alkoxy group substituted by a lower alkoxy group, (7) a carbonyl group substituted by a group selected from a morpholinyl group, a piperidyl group or a pyrrolidinyl group, (8) a carbonyl group substituted by a hydroxypiperidyl group, (9) a piperidylcarbonyl group substituted by a hydroxy-lower alkyl group,

(10) a pyrrolidinylcarbonyl group substituted by a hydroxy-lower alkyl group,

(11) a carbonyl group substituted by a lower alkyl-piperazinyl group,

(12) an amino group optionally substituted by 1 to 2 groups selected from (a) a lower alkyl group, (b) a lower alkoxy-carbonyl group, and(c) a lower alkanoyl group,

(13) a carbamoyl group optionally substituted by 1 to 2 groups selected from (a) a lower alkyl group, (b) a lower alkoxy-lower alkyl group, (c) a lower alkyl group substituted by a hydroxyl group, and (d) a lower alkyl group substituted by an amino group optionally substituted by 1 to 2 lower alkyl groups, and

(14) a group of the formula:

—O—NH—C(=NH)$NH_2$; or

D) a carbonyl group substituted by a group selected from the following:

(1) a lower alkoxy group, (2) a hydroxyl group, (3) an amino group optionally substituted by 1 to 2 groups selected from (a) a lower alkyl group, (b) a lower alkoxy group, (c) a lower alkoxy-lower alkyl group, (d) a hydroxy-lower alkyl group, (e) a lower alkyl group substituted by an amino group optionally substituted by 1 to 2 lower alkyl groups, (f) a lower alkyl group substituted by an aromatic hydrocarbon group, and (g) a lower alkyl group substituted by a pyridyl group, (4) a morpholinyl group, a pyrrolidinyl group, a piperidyl group or a thiomorpholinyl group, (5) a hydroxypiperidyl group, (6) a piperidyl group substituted by a hydroxy-lower alkyl group, (7) a pyrrolidinyl group substituted by a hydroxy-lower alkyl group, and (8) a lower alkyl-piperazinyl group;

A is a single bond; and $R^3$ is a hydrogen atom.

8. The compound according to claim 7, wherein $R^2$ is a group selected from the following:

(1) a hydrogen atom, (2) a cyano group, (3) an amino group optionally substituted by 1 to 2 lower alkyl groups, (4) a hydroxyl group, (5) a lower alkoxy group, (6) a lower alkoxy group substituted by a lower alkoxy group, (7) a lower alkoxy group substituted by a hydroxyl group, (8) a lower alkoxy group substituted by an amino group optionally substituted by 1 to 2 lower alkyl groups, (9) a lower alkoxycarbonyl group,

(10) a carboxyl group,

(11) a carbonyl group substituted by an amino group optionally substituted by 1 to 2 groups selected from (a) lower alkyl group, (b) a hydroxy-lower alkyl group, (c) a lower alkoxy-lower alkyl group, and (d) a lower alkyl group substituted by an amino group optionally substituted by 1 to 2 lower alkyl groups,

(12) a morpholinylcarbonyl group, a pyrrolidinylcarbonyl group, a piperidylcarbonyl group or a thiomorpholinyl-carbonyl group,

(13) a piperidylcarbonyl group substituted by a hydroxy-lower alkyl group, or a pyrrolidinylcarbonyl group substituted by a hydroxy-lower alkyl group,

(14) a lower alkyl group,

(15) a lower alkyl group substituted by a lower alkoxycarbonyl group,

(16) a carboxy-lower alkyl group,

(17) a lower alkyl group substituted by a carbamoyl group optionally substituted by 1 to 2 groups selected from (a) a lower alkyl group, (b) a hydroxy-lower alkyl group, (c) a lower alkoxy-lower alkyl group, and (d) a lower alkyl group substituted by an amino group optionally substituted by 1 to 2 lower alkyl groups,

(18) a lower alkyl group substituted by a morpholinylcarbonyl group,

(19) a lower alkyl group substituted by a piperidylcarbonyl group substituted by a hydroxy-lower alkyl group, or a lower alkyl group substituted by a pyrrolidinylcarbonyl group substituted by a hydroxy-lower alkyl group,

(20) a hydroxy-lower alkyl group, and

(21) a lower alkyl group substituted by a pyrrolidinylcarbonyl group.

9. The compound according to claim 7, wherein $R^2$ is a group selected from the following:

(1) a hydrogen atom, (2) a carbonyl group substituted by an amino group optionally substituted by 1 to 2 groups selected from (a) a lower alkyl group and (b) a lower alkoxy-lower alkyl group, (3) a lower alkoxycarbonyl group, (4) a morpholinylcarbonyl group, a pyrrolidinylcarbonyl group, a piperidylcarbonyl group or a thiomorpholinyl-carbonyl group, (5) a lower alkyl group substituted by a carbamoyl group substituted by 1 to 2 lower alkyl groups, (6) a carboxy-lower alkyl group, (7) a lower alkyl group substituted by a morpholinylcarbonyl group, (8) a hydroxy-lower alkyl group, (9) a lower alkyl group substituted by a pyrrolidinylcarbonyl group, and

(10) a lower alkyl group substituted by a carbamoyl group optionally substituted by 1 to 2 groups selected from (a) a lower alkyl group substituted by an amino group optionally substituted by 1 to 2 lower alkyl groups and (b) lower alkyl group.

10. The compound according to claim 7, wherein $R^2$ is a group selected from the following:

(1) a hydrogen atom, (2) a hydroxy-lower alkyl group, (3) a carboxy-lower alkyl group, (4) a lower alkoxy group substituted by a lower alkoxy group;

(5) a carbonyl group substituted by a group selected from (a) an amino group optionally substituted by 1 to 2 lower alkyl groups, and (b) a morpholinyl group;

(6) a carbamoyl group substituted by 1 to 2 groups selected from (a) a lower alkoxy-lower alkyl group and (b) a lower alkyl group;

(7) a lower alkyl group substituted by a carbamoyl group substituted by 1 to 2 groups selected from (a) a lower alkoxy-lower alkyl group and (b) a lower alkyl group;

(8) a carbamoyl group substituted by 1 to 2 groups selected from (a) a lower alkyl group substituted by an amino group optionally substituted by 1 to 2 alkyl groups and (b) a lower alkyl group, (9) a lower alkyl group substituted by a carbamoyl group substituted by 1 to 2 groups selected from (a) an amino-lower alkyl group optionally substituted 1 to 2 alkyl groups and (b) a lower alkyl group,

(10) a lower alkyl group substituted by a pyrrolidinylcarbonyl group; and

(11) a carbamoyl-lower alkyl group optionally substituted by 1 to 2 groups selected from (a) a lower alkyl group substituted by an amino group optionally substituted by 1 to 2 lower alkyl groups and (b) a lower alkyl group.

11. A compound of the formula:

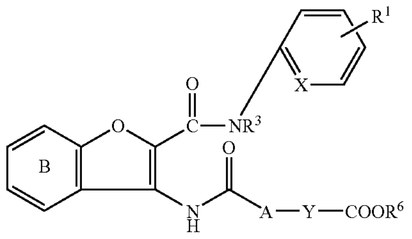

wherein X is a group of the formula: —N= or —CH=;

A is a single bond or a group of the formula: —NH—;

Y is a lower alkylene group, a cycloalkanediyl group, a phenyl group or a saturated heterocyclic group;

$R^6$ is a protecting group for carboxyl group;

$R^1$ is a hydrogen atom, a halogen atom, a lower alkyl group, a lower alkoxy group, a cyano group, or an amino group optionally substituted by 1 to 2 lower alkyl groups;

Ring B of the formula:

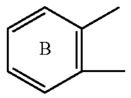

is an optionally substituted benzene ring; and $R^3$ is a hydrogen atom or a lower alkyl group.

12. A compound of the formula:

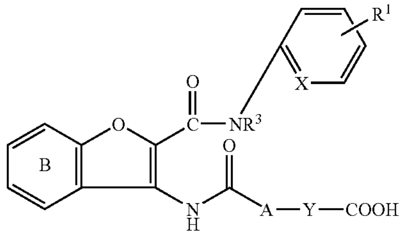

wherein X is a group of the formula: —N= or —CH=;

A is a single bond or a group of the formula: —NH—;

Y is a lower alkylene group, a cycloalkanediyl group, a phenyl group or a saturated heterocyclic group;

$R^1$ is a hydrogen atom, a halogen atom, a lower alkyl group, a lower alkoxy group, a cyano group, or an amino group optionally substituted by 1 to 2 lower alkyl groups;

Ring B of the formula:

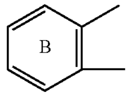

is an optionally substituted benzene ring; and $R^3$ is a hydrogen atom or a lower alkyl group.

13. The compound according to claim 11 or 12, wherein the formula:

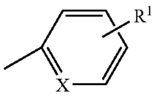

is

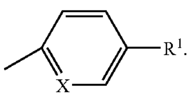

14. The compound according to claim 5, wherein Ring Z is a group of the formula:

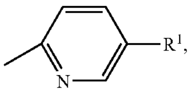

$R^1$ is a halogen atom;

$R^3$ is a hydrogen atom;

the formula:

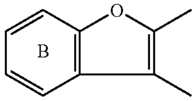 is 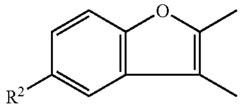 or

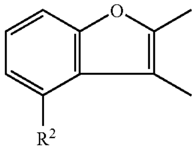 ;

$R^2$ is a carbonyl group substituted by a group selected from the following:

(1) a lower alkoxy group, (2) a hydroxyl group, (3) an amino group optionally substituted by 1 to 2 groups elected from (a) a lower alkyl group, (b) a lower alkoxy group, (c) a lower alkoxy-lower alkyl group, (d) a hydroxy-lower alkyl group, (e) a lower alkyl group substituted by an amino group optionally substituted by 1 to 2 lower alkyl groups, (f) a lower alkyl group substituted by an aromatic hydrocarbon group, and (g) a lower alkyl group substituted by a pyridyl group, (4) a morpholinyl group, a pyrrolidinyl group, a piperidyl group or a thiomorpholinyl group, (5) a hydroxypiperidyl group, (6) a piperidyl group substituted by a hydroxy-lower alkyl group, (7) a pyrrolidinyl group substituted by a hydroxy-lower alkyl group, and (8) a lower alkyl-piperazinyl group;

A is a single bond;

Y is a cyclohexanediyl group; and $R^4$ and $R^5$ are independently a lower alkyl group, or $R^4$, $R^5$ and the adjacent nitrogen atom, when $R^4$ and $R^5$ combine together at the ends, form a pyrrolidinyl group, a morpholinyl group, a pyrrolidinyl group substituted by a hydroxy-lower alkyl group, a pyrrolidinyl group substituted by a hydroxyl group, a thiomorpholinyl group, a piperidyl group, a piperidyl group substituted by a hydroxyl group, a piperazinyl group substituted by a hydroxy-lower alkyl group, a piperidyl group substituted by a hydroxy-lower alkyl group, a piperazinyl group substituted by a lower alkyl group, a pyrrolidinyl group substituted by a lower alkoxycarbonylamino group, a piperidyl group substituted by an amino group optionally substituted by 1 to 2 lower alkyl groups, an oxopyrrolidinyl group, an oxomorpholinyl group, an oxothiomorpholinyl group, an oxopiperidyl group, an oxopiperazinyl group, or a piperidyl group substituted by a lower alkoxycarbonyl group.

15. The compound according to claim 14, wherein $R^2$ is a carbonyl group substituted by a group selected from the following:

(1) an amino group optionally substituted by 1 to 2 groups selected from (a) a lower alkyl group, (b) a lower alkoxy group, (c) a lower alkoxy-lower alkyl group, (d) a hydroxy-lower alkyl group, (e) a lower alkyl group substituted by an amino group optionally substituted by 1 to 2 lower alkyl group, (f) a lower alkyl group substituted by an aromatic hydrocarbon group, and (g) a lower alkyl group substituted by a pyridyl group, and (2) a morpholin-4-yl group, a pyrrolidin-1-yl group, a piperidin-1-yl group a piperazin-1-yl group or a thiomorpholin-4-yl group;

$R^4$ and $R^5$ are independently a lower alkyl group, or $R^4$, $R^5$ and the adjacent nitrogen atom, when $R^4$ and $R^5$ combine together at the ends, form a pyrrolidin-4-yl group.

16. The compound according to claim 15, wherein the formula:

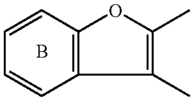 is 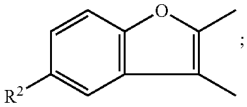 ;

$R^2$ is a carbonyl group substituted by a group selected from the following:

(1) an amino group optionally substituted by 1 to 2 groups selected from (a) a lower alkyl group and (b) a lower alkoxy-lower alkyl group, and (2) a morpholin-4-yl group.

17. Methyl 2-{[(5 -chloropyridin-2-yl)amino]carbonyl}-3-[({trans-4-[(dimethylamino)carbonyl] cyclohexyl}carbonyl)amino]benzofuran-5-carboxylate;

Methyl [2- {[(5-chloropyridin-2-yl)amino]carbonyl}-3-({[trans-4-(pyrrolidin- 1-ylcarbonyl)cyclohexyl] carbonyl}amino)benzofuran-5-yl]acetate;

$N^2$-(5-Chloropyridin-2-yl)-$N^5$,$N^5$-dimethyl-3 -({[trans-4-(morpholin-4-ylcarbonyl)cyclohexyl] carbonyl}amino)-benzofuran-2,5-dicarboxamide;

N-(5-Chloropyridin-2-yl)-3-[(5-morpholin-4-yl -5-oxo-pentanoyl)amino]benzofuran-2-carboxamide;

2- {[(5-Chloropyridin-2-yl)amino]carbonyl}-3-[({trans-4-[(dimethylamino)carbonyl]cyclohexyl}carbonyl) amino]-benzofuran-5-carboxylic acid;

$N^2$-(5-Chloropyridin-2-yl)-3-[({trans-4-[(dimethylamino)carbonyl]cyclohexyl}carbonyl)amino]-$N^5$,$N^5$-dimethylbenzofuran-2,5-dicarboxamide;

trans-N'-[2-{[(5-Chloropyridin-2-yl)amino]carbonyl}-5-morpholin-4-ylcarbonyl)benzofuran-3-yl]-N,N-dimethylcyclohexane- 1,4-dicarboxamide, or a pharmaceutically acceptable-salt thereof.

18. A pharmaceutical composition, which comprises as an active ingredient a compound according to claim 1, or a pharmaceutically acceptable salt thereof.

19. A method for treatment of thrombosis, which comprises administering an effective amount of a compound according to claim 1, or a pharmaceutically acceptable salt thereof, to a patient in need thereof.

* * * * *